(12) United States Patent
Ripka et al.

US008481534B2

(10) Patent No.: US 8,481,534 B2
(45) Date of Patent: *Jul. 9, 2013

(54) 5- AND 6-MEMBERED HETEROCYCLIC COMPOUNDS

(75) Inventors: Amy Ripka, Reading, MA (US); Gideon Shapiro, Gainesville, FL (US); Richard Chesworth, Boston, MA (US)

(73) Assignee: EnVivo Pharmaceuticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/001,359

(22) PCT Filed: Jun. 25, 2009

(86) PCT No.: PCT/US2009/048617
§ 371 (c)(1),
(2), (4) Date: Apr. 4, 2011

(87) PCT Pub. No.: WO2009/158473
PCT Pub. Date: Dec. 30, 2009

(65) Prior Publication Data
US 2011/0183976 A1    Jul. 28, 2011

Related U.S. Application Data

(60) Provisional application No. 61/075,594, filed on Jun. 25, 2008, provisional application No. 61/109,162, filed on Oct. 28, 2008, provisional application No. 61/138,866, filed on Dec. 18, 2008, provisional application No. 61/176,413, filed on May 7, 2009.

(51) Int. Cl.
| | |
|---|---|
| *A61K 31/5377* | (2006.01) |
| *A61K 31/53* | (2006.01) |
| *A61K 31/50* | (2006.01) |
| *A61K 31/496* | (2006.01) |
| *A61K 31/497* | (2006.01) |
| *A61K 31/517* | (2006.01) |
| *A61K 31/505* | (2006.01) |
| *A61K 31/4427* | (2006.01) |
| *A61K 31/44* | (2006.01) |
| *C07D 413/02* | (2006.01) |
| *C07D 413/14* | (2006.01) |
| *C07D 401/02* | (2006.01) |
| *C07D 241/36* | (2006.01) |
| *C07D 471/00* | (2006.01) |
| *C07D 215/00* | (2006.01) |
| *C07D 405/02* | (2006.01) |

(52) U.S. Cl.
USPC ... 514/235.2; 514/241; 514/249; 514/252.04; 514/266.21; 514/300; 514/314; 544/128; 544/284; 544/353; 546/122; 546/174; 546/175; 546/284.4

(58) Field of Classification Search
USPC ............ 514/235.2, 241, 249, 252.04, 266.21, 514/300, 314; 544/128, 284, 353; 546/122, 546/174, 175, 284.4
See application file for complete search history.

(56) References Cited

U.S. PATENT DOCUMENTS

| | | |
|---|---|---|
| 8,071,595 B2 | 12/2011 | Ripka et al. |
| 2003/0032579 A1 | 2/2003 | Lebel et al. |
| 2010/0292238 A1 | 11/2010 | Ripka et al. |
| 2011/0053905 A1 | 3/2011 | Guo et al. |
| 2012/0040979 A1 | 2/2012 | Falco et al. |
| 2012/0046320 A1 | 2/2012 | KC et al. |
| 2012/0053202 A1 | 3/2012 | De Peretti et al. |

FOREIGN PATENT DOCUMENTS

| | | |
|---|---|---|
| EP | 1541149 | 6/2005 |
| WO | WO-2006072828 A2 | 7/2006 |
| WO | WO-2007077490 A2 | 7/2007 |
| WO | WO-2007129183 A2 | 11/2007 |
| WO | WO 2008/033455 | 3/2008 |
| WO | WO-2009158393 A1 | 12/2009 |
| WO | WO-2009158473 A1 | 12/2009 |

OTHER PUBLICATIONS

U.S. Appl. No. 13/290,527, filed Nov. 7, 2011, Ripka et al.
Davis, J.M et al. "Dose response and dose equivalence of antipsychotics." Journal of Clinical Psychopharmacology, Apr. 2004, 24 (2),192-208.
Fernandez et al "Treatment of psychosis in Parkinson's disease: Safety considerations." Drug Safety, 2003, 26 (9), 643-659.
Fujishige et al. "Cloning and characterization of a novel human phosphodiesterase that hydrolyzes both cAMP and cGMP (PDE10A)" J. Biol. Chem. Jun. 1999,274, 18438-18445.
Handa et al. "Crystal structure of the GAF-B domain from human phosphodiesterase 10A complexed with its ligand, cAMP" J Biol. Chem. Jul. 2008, pp. 19657-19664.
Kostowski et. al "Papaverine drug induced stereotypy and catalepsy and biogenic aminesin the brain of the rat" Pharmacol. Biochem. Behav. Jul. 1976, 5, 15-17.
Lazorthes et al. "Advances in Drug Delivery Systems and Applications in Neurosurgery." Advances and Technical Standards in Neurosurgery, vol. 18, 1991. 143-192.
Loughney et al. "Isolation and characterization of PDE10A, a novel human 3',5'-cyclicnucleotide phosphodiesterase" Gene, Jun. 1999, vol. 234, No. 1. pp. 109-117.

(Continued)

*Primary Examiner* — Samantha Shterengarts
(74) *Attorney, Agent, or Firm* — Wilmer Cutler Pickering Hale and Dorr LLP

(57) ABSTRACT

5- and 6-membered heterocyclic compounds which are inhibitors of phosphodiesterase 10 are described as are processes, pharmaceutical compositions, pharmaceutical preparations and pharmaceutical use of the compounds in the treatment of mammals, including human(s) for central nervous system (CNS) disorders and other disorders which may affect CNS function. Also described is the treatment of neurological, neurodegenerative and psychiatric disorders including but not limited to those comprising cognitive deficits or schizophrenic symptoms.

12 Claims, No Drawings

OTHER PUBLICATIONS

Meyer et al "The Clinical Antipsychotic Trials of Intervention Effectiveness (CATIE) Schizophrenia Trial: clinical comparison of subgroups with and without the metabolic syndrome." Schizophrenia Research, 2005, 80 (1), 9-43.

Minto, J. et al., Pharmacokinetics and Pharmacodynamics of Nandrolone Esters in Oil Vehicle: Effects of Ester, Injection Site and Injection Volume, Pharmcol. Exp. Ther. vol. 291, No. 1. Apr. 1997. pp. 93-102.

Navidpour et al., Design and synthesis of new water-soluble tetrazolide derivatives of celecoxib and refecoxib as selective cyclooxygenase-2 (COX-2) inhibitors, 2006, Bioorganic & Medicinal Chemistry Letters, 16, 4483-4487.

Ommaya et al. "Implantable Devices for Chronic Access and Drug Delivery to the Central Nervous System", Cancer Drug Delivery, vol. 1, No. 2, 1984. pp. 169-179.

Patani et al., Bioisosterism: A Rational Approach in Drug Design, 1996, Chem. Rev., vol. 96, No. 8. pp. 3147-3176.

Soderling and Beavo "Regulation of cAMP and cGMP signaling: New phosphodiesterases and new functions," Curr. Opin. Cell Biol., Apr. 2000, vol. 12, No. 2. pp. 174-179.

Soderling et al. "Isolation and characterization of a dual-substrate phosphodiesterase gene family: PDE10A" Proc. Natl Sci. Jun. 8, 1999, vol. 96, No. 12. pp. 7071-7076.

5- AND 6-MEMBERED HETEROCYCLIC COMPOUNDS

This application is the U.S. national stage under 35 USC §371 of International Application Number PCT/US2009/048617, filed on Jun. 25, 2009, which claims priority to U.S. Patent Application No. 61/075,594, filed on Jun. 25, 2008; U.S. Patent Application No. 61/109,162, filed Oct. 28, 2008; U.S. Application No. 61/138,866, filed Dec. 18, 2008; and U.S. Application No. 61/176,413, filed May 7, 2009, the entire contents of which applications are hereby incorporated by reference.

The disclosure relates to 5- and 6-membered heterocyclic compounds which are inhibitors of phosphodiesterase 10. The disclosure further relates to processes, pharmaceutical compositions, pharmaceutical preparations and pharmaceutical use of the compounds in the treatment of mammals, including human(s) for central nervous system (CNS) disorders and other disorders which may affect CNS function. The disclosure also relates to methods for treating neurological, neurodegenerative and psychiatric disorders including but not limited to those comprising cognitive deficits or schizophrenic symptoms.

BACKGROUND

Cyclic phosphodiesterases are intracellular enzymes which, through the hydrolysis of cyclic nucleotides cAMP and cGMP, regulate the levels of these mono phosphate nucleotides which serve as second messengers in the signaling cascade of G-protein coupled receptors. In neurons, PDEs also play a role in the regulation of downstream cGMP and cAMP dependent kinases which phosphorylate proteins involved in the regulation of synaptic transmission and homeostasis. To date, eleven different PDE families have been identified which are encoded by 21 genes. The PDEs contain a variable N-terminal regulatory domain and a highly conserved C-terminal catalytic domain and differ in their substrate specificity, expression and localization in cellular and tissue compartments, including the CNS.

The discovery of a new PDE family, PDE10, was reported simultaneously by three groups in 1999 (Soderling et al. "Isolation and characterization of a dual-substrate phosphodiesterase gene family: PDE10A" *Proc. Natl. Sci.* 1999, 96, 7071-7076; Loughney et al. "Isolation and characterization of PDE10A, a novel human 3',5'-cyclic nucleotide phosphodiesterase" *Gene* 1999, 234, 109-117; Fujishige et al. "Cloning and characterization of a novel human phosphodiesterase that hydrolyzes both cAMP and cGMP (PDE10A)" *J. Biol. Chem.* 1999, 274, 18438-18445). The human PDE10 sequence is highly homologous to both the rat and mouse variants with 95% amino acid identity overall, and 98% identity conserved in the catalytic region.

PDE10 is primarily expressed in the brain (caudate nucleus and putamen) and is highly localized in the medium spiny neurons of the striatum, which is one of the principal inputs to the basal ganglia. This localization of PDE10 has led to speculation that it may influence the dopaminergic and glutamatergic pathways both which play roles in the pathology of various psychotic and neurodegenerative disorders.

PDE10 hydrolyzes both cAMP ($K_m$=0.05 uM) and cGMP ($K_m$=3 uM) (Soderling et al. "Isolation and Characterization of a dual-substrate phosphodiesterase gene family: PDE10." *Proc. Natl. Sci. USA* 1999, 96(12), 7071-7076). In addition, PDE10 has a five-fold greater $V_{max}$ for cGMP than for cAMP and these in vitro kinetic data have lead to the speculation that PDE10 may act as a cAMP-inhibited cGMP phosphodiesterase in vivo (Soderling and Beavo "Regulation of cAMP and cGMP signaling: New phosphodiesterases and new functions," *Curr. Opin. Cell Biol.*, 2000, 12, 174-179).

PDE10 is also one of five phosphodiesterase members to contain a tandem GAF domain at their N-terminus. It is differentiated by the fact that the other GAF containing PDEs (PDE2, 5, 6, and 11) bind cGMP while recent data points to the tight binding of cAMP to the GAF domain of PDE10 (Handa et al. "Crystal structure of the GAF-B domain from human phosphodiesterase 10A complexed with its ligand, cAMP" *J. Biol. Chem.* 2008, May 13th, ePub).

PDE10 inhibitors have been disclosed for the treatment of a variety of neurological and psychiatric disorders including Parkinson's disease, schizophrenia, Huntington's disease, delusional disorders, drug-induced psychoses, obsessive compulsive and panic disorders (US Patent Application 2003/0032579). Studies in rats (Kostowski et. al "Papaverine drug induced stereotypy and catalepsy and biogenic amines in the brain of the rat" *Pharmacol. Biochem. Behav.* 1976, 5, 15-17) have showed that papaverine, a selective PDE10 inhibitor, reduces apomorphine induced stereotypes and rat brain dopamine levels and increases haloperidol induced catalepsy. This experiment lends support to the use of a PDE10 inhibitor as an antipsychotic since similar trends are seen with known, marketed antipsychotics.

Antipsychotic medications are the mainstay of current treatment for schizophrenia. Conventional or classic antipsychotics, typified by haloperidol, were introduced in the mid-1950s and have a proven track record over the last half century in the treatment of schizophrenia. While these drugs are effective against the positive, psychotic symptoms of schizophrenia, they show little benefit in alleviating negative symptoms or the cognitive impairment associated with the disease. In addition, drugs such as haloperidol have extreme side effects such as extrapyramidal symptoms (EPS) due to their specific dopamine D2 receptor interaction. An even more severe condition characterized by significant, prolonged, abnormal motor movements known as tardive dyskinesia also may emerge with prolonged classic antipsychotic treatment.

The 1990s saw the development of several new drugs for schizophrenia, referred to as atypical antipsychotics, typified by risperidone and olanzapine and most effectively, clozapine. These atypical antipsychotics are generally characterized by effectiveness against both the positive and negative symptoms associated with schizophrenia, but have little effectiveness against cognitive deficiencies and persisting cognitive impairment remain a serious public health concern (Davis, J. M et al. "Dose response and dose equivalence of antipsychotics." *Journal of Clinical Psychopharmacology,* 2004, 24 (2), 192-208; Friedman, J. H. et al "Treatment of psychosis in Parkinson's disease: Safety considerations." *Drug Safety,* 2003, 26 (9), 643-659). In addition, the atypical antipsychotic agents, while effective in treating the positive and, to some degree, negative symptoms of schizophrenia, have significant side effects. For example, clozapine which is one of the most clinically effective antipsychotic drugs shows agranulocytosis in approximately 1.5% of patients with fatalities due to this side effect being observed. Other atypical antipsychotic drugs have significant side effects including metabolic side effects (type 2 diabetes, significant weight gain, and dyslipidemia), sexual dysfunction, sedation, and potential cardiovascular side effects that compromise their clinically effectiveness. In the large, recently published NIH sponsored CATIE study, (Lieberman et al "The Clinical Antipsychotic Trials Of Intervention Effectiveness (CATIE) Schizophrenia Trial: clinical comparison of subgroups with and without the metabolic syndrome." *Schizophrenia Research,* 2005, 80 (1), 9-43) 74% of patients discontinued use of their antipsychotic medication within 18 months due to a number of factors including poor tolerability or incomplete efficacy. Therefore, a substantial clinical need still exists for more effective and better tolerated antipsychotic mediations possibly through the use of PDE10 inhibitors.

BRIEF SUMMARY

Described herein are 5- and 6-membered heterocyclic compounds of Formulas (I), (II) or (III) which are inhibitors of at least one phosphodiesterase 10 (e.g., PDE-10A):

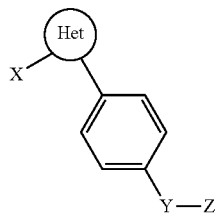
(I)

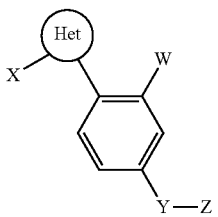
(II)

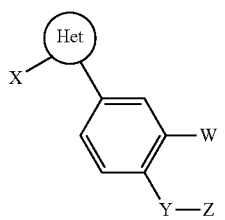
(III)

Wherein:
HET is a heterocyclic ring selected from Formulas A1-A2, A6-A8, A10-A32 and A38 below A1
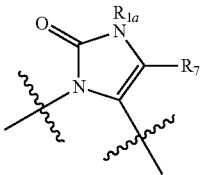

A2
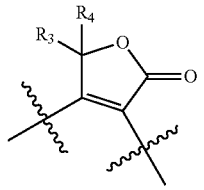

-continued

A6
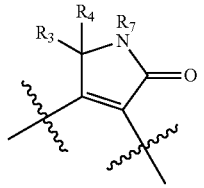

A7
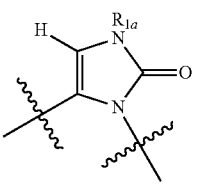

A8
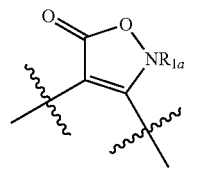

A10
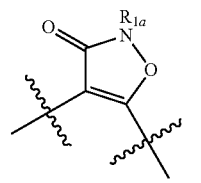

A11

A12

A13
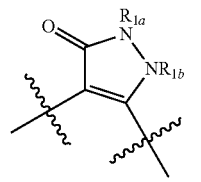

A14
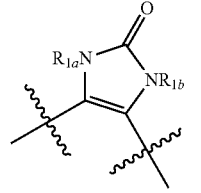

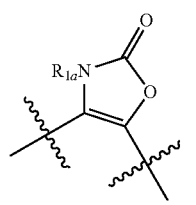 A15
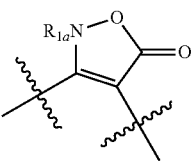 A16
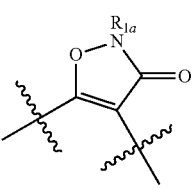 A17
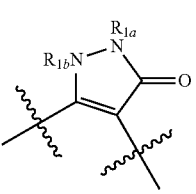 A18
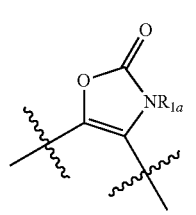 A19
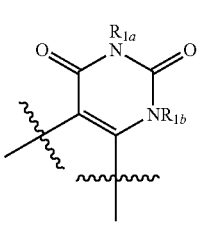 A20
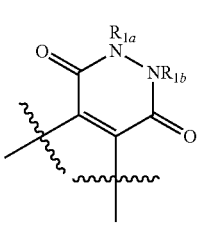 A21
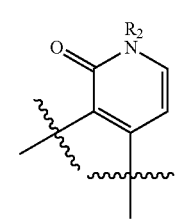 A22
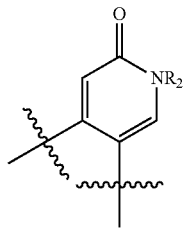 A23
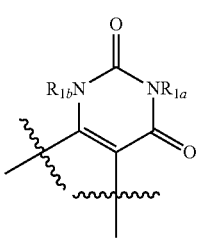 A24
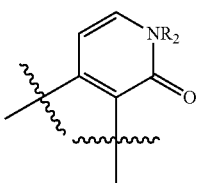 A25
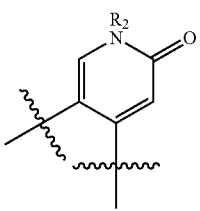 A26
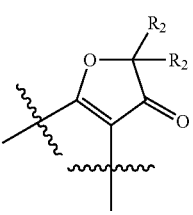 A29
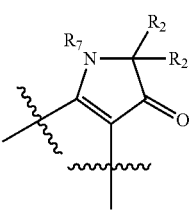 A30
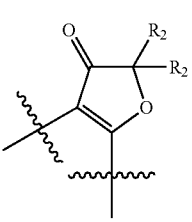 A31

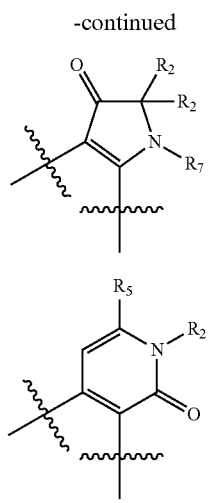

and the left most radical is connected to the X group;
W is selected from halogen, cyano, nitro, alkoxy, amino, alkylamino, dialkylamino, carboxy, amido, alkylamido, and dialkylamido;
X is selected from $C_3$-$C_8$ alkyl, optionally substituted cycloalkyl, optionally substituted cycloalkylalkyl, optionally substituted heterocycloalkyl, optionally substituted heterocycloalkylalkyl, optionally substituted aryl, optionally substituted arylalkyl, optionally substituted heteroaryl and optionally substituted heteroarylalkyl;
Y is a bond or a divalent linker group selected from —$CH_2$—, —O—, —$SO_2$—, —$CH_2O$—, —$OCH_2$— and —$CH_2CH_2$— with the rightmost radical of the Y group connected to the Z substituent;
Z is optionally substituted heteroaryl;
$R_{1a}$ is selected from hydrogen, optionally substituted alkyl, optionally substituted cycloalkyl, optionally substituted cycloalkylalkyl and optionally substituted alkoxyalkyl with the proviso that when $R_{1a}$ is not hydrogen, $R_{1b}$ is hydrogen or that when $R_{1b}$ is absent, $R_{1a}$ must be hydrogen;
$R_{1b}$ is selected from hydrogen, optionally substituted alkyl, optionally substituted cycloalkyl, optionally substituted cycloalkylalkyl and optionally substituted alkoxyalkyl with the proviso that when $R_{1b}$ is not hydrogen, $R_{1a}$ is hydrogen;
Each $R_2$ is independently selected from hydrogen, optionally substituted alkyl, optionally substituted cycloalkyl, optionally substituted cycloalkylalkyl and optionally substituted alkoxyalkyl with the proviso that when two $R_2$ are present, at least one $R_2$ is hydrogen;
$R_3$ and $R_4$ are independently selected from hydrogen, $C_1$-$C_4$ alkyl, $CF_3$ and optionally substituted cycloalkyl with the proviso that at least one $R_3$ or $R_4$ group must be hydrogen;
$R_5$ is selected from alkyl, optionally substituted cycloalkyl, optionally substituted cycloalkylalkyl and optionally substituted alkoxyalkyl;
$R_7$ is selected from hydrogen, optionally substituted alkyl, optionally substituted cycloalkyl, optionally substituted cycloalkylalkyl and optionally substituted alkoxyalkyl; and
n is independently selected from 1 and 2.

In some embodiments, alkyl groups are fully saturated whether present on their own or as part of another group (e.g., alkylamino).

In certain embodiments, substituent groups are not further substituted.

In various embodiments, any group that is defined as being optionally substituted is independently singly or multiply substituted.

In various embodiments, any group that is defined as being optionally substituted not substituted.

In one embodiment, a compound of Formula (I) is selected.

In another embodiment, a compound of Formula (II) is selected.

In another embodiment, a compound of Formula (III) is selected.

In one embodiment, alkyl groups are fully saturated whether present on their own or on another group.

In a further embodiment, HET is selected from Formulas A7, A8, A14, A15, A19, A25, A29, A30, A31, A32, and A38.

In a further embodiment, HET is selected from Formulas A7, A8, A25, A29, A30, A31, A32, and A38.

In another embodiment, HET is selected from Formulas A7, A8, A25, A29, A30 and A38.

In another embodiment, HET is selected from Formulas A7, A8, A11 A18, A25, A29, and A30.

In one embodiment, HET is selected from Formulas A1, A2, A7, A8, A14, A15 and A19.

In another embodiment, HET is selected from Formulas A6, A9 A10, A20 and A24.

In an additional embodiment, HET is selected from Formulas A1, A2, A7 and A8.

In another embodiment, HET is selected from Formulas A22, A23, A25 and A26.

In another embodiment, HET is selected from Formulas A29, A30, A31 and A32.

In another embodiment, HET is selected from Formulas A7, A8, A29 and A30.

In a further embodiment, HET is selected from Formulas A7, A8, A29 and A31.

In another embodiment, HET is selected from Formulas A29, A31 and A38.

In another embodiment, HET is selected from Formulas A25, A29 and A38.

In another embodiment, HET is selected from Formulas A25, A29 and A30.

In another embodiment, HET is selected from Formulas A25 and A38.

In another embodiment, HET is selected from Formulas A7 and A8.

In another embodiment, HET is selected from Formulas A25 and A26.

In another embodiment, HET is selected from Formulas A29 and A30.

In another embodiment, HET is selected from Formulas A29 and A31.

In a further embodiment, HET is selected from Formulas A31 and A32.

In another embodiment, HET is Formula A1.
In another embodiment, HET is Formula A2.
In another embodiment, HET is Formula A6.
In another embodiment, HET is Formula A7.
In another embodiment, HET is Formula A8.
In another embodiment, HET is Formula A10.
In another embodiment, HET is Formula A11.
In another embodiment, HET is Formula A12.
In another embodiment, HET is Formula A13.
In another embodiment, HET is Formula A14.
In another embodiment, HET is Formula A15.
In another embodiment, HET is Formula A16.
In another embodiment, HET is Formula A17.
In another embodiment, HET is Formula A18.
In another embodiment, HET is Formula A19.
In another embodiment, HET is Formula A20.
In another embodiment, HET is Formula A21.
In another embodiment, HET is Formula A22.

In another embodiment, HET is Formula A23.
In another embodiment, HET is Formula A24.
In another embodiment, HET is Formula A25.
In another embodiment, HET is Formula A26.
In another embodiment, HET is Formula A29.
In another embodiment, HET is Formula A30.
In another embodiment, HET is Formula A31.
In another embodiment, HET is Formula A32.
In another embodiment, HET is Formula A38.
In one embodiment, W is selected from nitro, carboxy, amido, alkylamido, and dialkylamido.
In another embodiment, W is selected from amino, alkylamino and dialkylamino.
In a further embodiment, W is selected from halogen, cyano and alkoxy.
In another embodiment, W is selected from halogen and cyano.
In another embodiment, W is halogen.
In another embodiment, W is cyano.
In another embodiment, W is alkoxy.
In one embodiment, X is selected from $C_3$-$C_8$ alkyl, cycloalkyl and cycloalkylalkyl.
In a further embodiment X is selected from cycloalkyl and cycloalkylalkyl. Examples include, but are not limited to, cyclohexyl and cyclohexylmethyl.
In another embodiment X is $C_3$-$C_8$ alkyl. Examples include, but are not limited to, isopropyl, t-butyl and isopentyl.
In an additional embodiment, X is heterocycloalkyl.
In a further embodiment X is heterocycloalkyl having only 6 ring atoms. Examples include, but are not limited to, morpholinyl, piperidinyl, piperazinyl N-Me-piperazinyl and pyranyl.
In another embodiment X is heterocycloalkyl having only 5 ring atoms. Examples include, but are not limited to, tetrahydrofuranyl and pyrrolidinyl.
In another embodiment, X is a heterocycloalkyl group selected from Formulas B1-B16 depicted below:

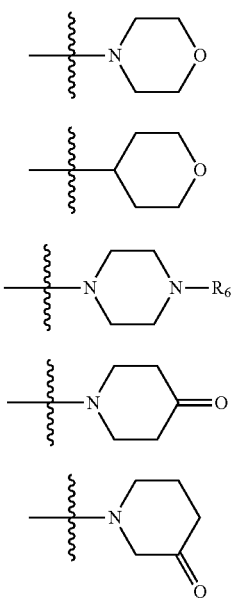

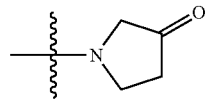

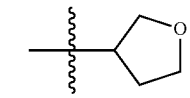

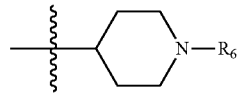

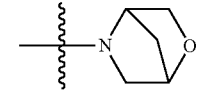

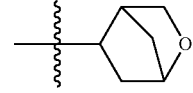

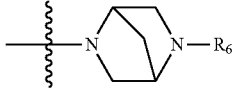

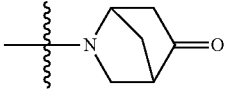

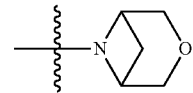

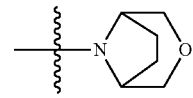

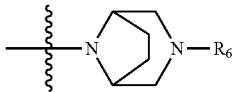

wherein $R_6$ is selected from hydrogen and $C_1$-$C_6$ alkyl, $C_3$-$C_6$ cycloalkyl and $C_3$-$C_6$ cycloalkylalkyl, all of which can be optionally substituted.
In another embodiment X is selected from morpholinyl, pyranyl and tetrahydrofuranyl.
In another embodiment X is selected from morpholinyl (having formula B1) and 4-pyranyl (having Formula B2).
In another embodiment X is heteroaryl.
In another embodiment, X is selected from a monocyclic aromatic ring having 5 ring atoms selected from C, O, S and N provided the total number of ring heteroatoms is less than or equal to four and where no more than one of the total number of heteroatoms is oxygen or sulfur, and a monocyclic aromatic ring having 6 atoms selected from C and N provided that not more than 3 ring atoms are N, and where said ring may be optionally and independently substituted with up to two groups selected from $C_1$-$C_4$ alkyl, cycloalkyl, cycloalkyloxy, $C_1$-$C_4$ alkoxy, $CF_3$, carboxyl, alkoxyalkyl, $C_1$-$C_4$ cycloalkylalkoxy, amino, alkylamino, dialkylamino, amido, alkylamido, dialkylamido, thioalkyl, halogen, cyano, and nitro. Examples include but are not limited to 1H-pyrrolyl, furanyl, thiophenyl, imidazolyl, pyrazolyl, isothiazolyl, isoxazolyl, oxazolyl, thiazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, 1,2,3,4-oxatriazolyl, 1,2,3,5-oxatriazolyl, 1,2,3,4-thiatriazolyl, 1,2,3,5-thiatriazolyl, 1,2,3-triazinyl, 1,2,4-triazinyl, 1,3,5-triazinyl, pyridinyl, pyrazinyl, pyridazinyl and pyrimidinyl.

In a further embodiment, X is a monocyclic aromatic ring having 6 ring atoms selected from C and N provided that not more than 3 ring atoms are N, and where said ring may be optionally and independently substituted with up to two groups selected from $C_1$-$C_4$ alkyl, cycloalkyl, cycloalkyloxy, $C_1$-$C_4$ alkoxy, $CF_3$, carboxyl, alkoxyalkyl, $C_1$-$C_4$ cycloalkylalkoxy, amino, alkylamino, dialkylamino, amido, alkylamido, dialkylamido, thioalkyl, halogen, cyano, and nitro. Examples include but are not limited to 1,2,3-triazinyl, 1,2,4-triazinyl, 1,3,5-triazinyl, pyridinyl, pyrazinyl, pyridazinyl and pyrimidinyl.

In a further embodiment, X is a monocyclic aromatic ring having 5 ring atoms selected from C, O, S, and N, provided the total number of ring heteroatoms is less than or equal to four and where no more than one of the total number of heteroatoms is oxygen or sulfur and where said ring may be optionally and independently substituted with up to two groups selected from $C_1$-$C_4$ alkyl, cycloalkyl, cycloalkyloxy, $C_1$-$C_4$ alkoxy, $CF_3$, carboxyl, alkoxyalkyl, $C_1$-$C_4$ cycloalkylalkoxy, amino, alkylamino, dialkylamino, amido, alkylamido, dialkylamido, thioalkyl, halogen, cyano, and nitro. Examples include but are not limited to 1H-pyrrolyl, furanyl, thiophenyl, imidazolyl, pyrazolyl, isothiazolyl, isoxazolyl, oxazolyl, thiazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, 1,2,3,4-oxatriazolyl, 1,2,3,5-oxatriazolyl, 1,2,3,4-thiatriazolyl, 1,2,3,5-thiatriazolyl.

In a further embodiment, X is selected from 2-pyridinyl, 3-pyridinyl and 4-pyridinyl optionally substituted with one group selected from $C_1$-$C_4$ alkyl, cyclopropyl, cyclopropyloxy, cyclopropylmethyl, $C_1$-$C_4$ alkoxy, $CF_3$, amino, alkylamino, dialkylamino, thioalkyl, halogen or cyano.

In a further embodiment, X is 3-pyridinyl optionally substituted with one group selected from $C_1$-$C_4$ alkyl, cyclopropyl, cyclopropyloxy, cyclopropylmethyl, $C_1$-$C_4$ alkoxy, $CF_3$, amino, alkylamino, dialkylamino, thioalkyl, halogen or cyano.

In another embodiment, X is 4-pyridinyl optionally substituted with one group selected from $C_1$-$C_4$ alkyl, cyclopropyl, cyclopropyloxy, cyclopropylmethyl, $C_1$-$C_4$ alkoxy, $CF_3$, amino, alkylamino, dialkylamino, thioalkyl, halogen or cyano.

In a further embodiment, X is selected from 3-pyridinyl and 4-pyridinyl.
In a further embodiment, X is 3-pyridinyl.
In another embodiment, X is 2-methoxy-5-pyridinyl.
In a further embodiment, X is 4-pyridinyl.
In another embodiment, X is 2-methoxy-4-pyridinyl.
In another embodiment X is a heterobicyclic ring system.
In another embodiment X is a heterobicyclic ring system where one ring is aromatic.
In a further embodiment, X is a heterobicyclic ring system where both rings are aromatic.
In another embodiment, X is a heterobicyclic ring system containing exactly 9 ring atoms.
In another embodiment, X is a heterobicyclic ring system containing exactly 10 ring atoms.
In another embodiment X is selected from benzo[d]oxazoyl, benzo[c][1,2,5]oxadiazyl, benzo[c][1,2,5]thiadiazolyl, benzo[d]isoxazolyl, 1H-benzo[d]imidazoyl, benzo[d]thiazoyl, benzo[c]isothiazolyl, benzo[d]isothiazolyl, benzo[c]isoxazolyl, imidazo[1,2-a]pyridinyl and imidazo[1,5-a]pyridinyl
In another embodiment X is selected from benzo[c][1,2,5]oxadiazyl and benzo[c][1,2,5]thiadiazolyl.
In a further embodiment, X is selected from benzo[d]oxazoyl, 1H-benzo[d]imidazoyl and benzo[d]thiazoyl.
In a further embodiment, X is benzo[d]oxazoyl.
In a further embodiment, X is 1H-benzo[d]imidazoyl.
In a further embodiment, X is benzo[d]thiazoyl.
In another embodiment X is benzo[c][1,2,5]oxadiazoyl.
In a further embodiment X is benzo[c][1,2,5]thiadiazolyl
In a further embodiment, X is benzo[d]isoxazolyl.
In another embodiment, X is benzo[d]isothiazolyl.
In another embodiment, X is benzo[c]isothiazolyl.
In another embodiment, X is benzo[c]isoxazolyl.
In another embodiment, X is imidazo[1,2-a]pyridinyl.
In another embodiment, X is imidazo[1,5-a]pyridinyl.
In an additional embodiment, X is aryl.
In another embodiment, X is selected from phenyl and pyridinyl.
In a further embodiment, X is phenyl.
In another embodiment, X is phenyl optionally substituted with one or more substituents selected from F, Cl, CN, $NO_2$, $CF_3$, $OCF_3$, $OCHF_2$, $CH_2CF_3$ and OMe.
In another embodiment, X is restricted phenyl.
In a further embodiment, X is selected from a 3,4-disubstituted phenyl, 3-substituted phenyl and 4-substituted phenyl.
In another embodiment, X is selected from 3,4-disubstituted phenyl and 4-substituted phenyl.
In another embodiment, X is 3-chloro-4-methoxyphenyl
In another embodiment, X is 3-cyano-4-methoxyphenyl
In a further embodiment, X is 3-chloro-4-difluoromethoxyphenyl
In a further embodiment, X is 3-cyano-4-difluoromethoxyphenyl
In an additional embodiment, X is 4-substituted phenyl.
In a further embodiment, X is 4-methoxyphenyl.
In another embodiment, X is 4-nitrophenyl.
In another embodiment, X is 4-chlorophenyl.
In another embodiment, X is 4-cyanophenyl.
In another embodiment, X is 4-trifluoroethylphenyl.
In a further embodiment, X is 4-trifluoromethoxyphenyl.
In a further embodiment, X is 3-substituted phenyl.
In another embodiment, X is 3-nitrophenyl.
In another embodiment, X is 3-trifluoromethoxyphenyl.
In a further embodiment, X is 3-methoxyphenyl.
In another embodiment, X is 3-chlorophenyl.
In another embodiment, X is 3-cyanophenyl.
In another embodiment, X is 3-trifluoroethylphenyl.
In a further embodiment, X is 3-trifluoromethoxyphenyl.
In one embodiment, Y is —$CH_2O$— or —$OCH_2$— with the rightmost radical connected to the Z substituent.
In another embodiment, Y is —$CH_2CH_2$— with the rightmost radical connected to the Z substituent.
In an additional embodiment, Y is —$CH_2O$— with the rightmost radical connected to the Z substituent.
In a further embodiment, Y is —$OCH_2$— with the rightmost radical connected to the Z substituent.

In one embodiment, Z is selected from heteroaryl having only 6 ring atoms and a heterobicyclic ring system.

In another embodiment, Z is a heterobicyclic ring system.

In another embodiment, Z is a heterobicyclic ring system where one ring is aromatic.

In a further embodiment, Z is a heterobicyclic ring system where both rings are aromatic.

In another embodiment, Z is a heterobicyclic ring system containing exactly 9 ring atoms.

In another embodiment, Z is a heterobicyclic ring system containing exactly 10 ring atoms.

In an additional embodiment, Z is selected from benzimidazolyl, quinolinyl, tetrahydroquinolyl, imidazo[1,2-a]pyridin-2-yl, tetrahydroisoquinolyl, 5-methylpyridin-2-yl, 3,5-dimethylpyridin-2-yl, 6-fluoroquinolyl and isoquinolinyl, all of which may be optionally substituted with up to 3 substituents independently selected from alkyl, alkoxy, cycloalkyl, cycloalkyloxy, cycloalkylalkyl, cycloalkylalkoxy, halogen, alkylsulfonyl and cyano and nitro.

In an additional embodiment, Z is selected from benzimidazolyl, quinolinyl, tetrahydroquinolyl, tetrahydroisoquinolyl and isoquinolinyl, all of which may be optionally substituted with up to 3 substituents independently selected from alkyl, alkoxy, cycloalkyl, cycloalkyloxy, cycloalkylalkyl, cycloalkylalkoxy, halogen, alkylsulfonyl and cyano and nitro.

In an additional embodiment, Z is selected from quinolinyl, imidazo[1,2-a]pyridin-2-yl, 5-methylpyridin-2-yl, 3,5-dimethylpyridin-2-yl and 6-fluoroquinolin-2-yl, all of which may be optionally substituted with up to 3 substituents independently selected from alkyl, alkoxy, cycloalkyl, cycloalkyloxy, cycloalkylalkyl, cycloalkylalkoxy, halogen, alkylsulfonyl and cyano and nitro.

In an additional embodiment, Z is selected from quinolinyl and isoquinolinyl substituted with up to 3 substituents independently selected from alkyl, alkoxy, cycloalkyl, cycloalkyloxy, cycloalkylalkyl, cycloalkylalkoxy, halogen, alkylsulfonyl, cyano and nitro.

In a further embodiment, Z is selected from 2-quinolinyl and 2-benzimidazolyl substituted with up to 3 substituents independently selected from alkyl, alkoxy, cycloalkyl, cycloalkyloxy, cycloalkylalkyl, cycloalkylalkoxy, halogen, alkylsulfonyl and cyano and nitro.

In a further embodiment, Z is 2-quinolinyl substituted with up to 3 substituents independently selected from alkyl, alkoxy, cycloalkyl, cycloalkyloxy, cycloalkylalkyl, cycloalkylalkoxy, halogen, alkylsulfonyl and cyano and nitro.

In a further embodiment, Z is 6-fluoroquinolin-2-yl substituted with up to 3 substituents independently selected from alkyl, alkoxy, cycloalkyl, cycloalkyloxy, cycloalkylalkyl, cycloalkylalkoxy, halogen, alkylsulfonyl and cyano and nitro.

In a further embodiment, Z is 3,5-dimethylpyridin-2-yl substituted with up to 3 substituents independently selected from alkyl, alkoxy, cycloalkyl, cycloalkyloxy, cycloalkylalkyl, cycloalkylalkoxy, halogen, alkylsulfonyl and cyano and nitro.

In a further embodiment, Z is 5-methylpyridin-2-yl substituted with up to 3 substituents independently selected from alkyl, alkoxy, cycloalkyl, cycloalkyloxy, cycloalkylalkyl, cycloalkylalkoxy, halogen, alkylsulfonyl and cyano and nitro.

In an additional embodiment, Z is selected from 2-quinolinyl and 2-benzimidazolyl.

In an additional embodiment, Z is selected from 2-quinolinyl and 5-methylpyridin-2-yl.

In an additional embodiment, Z is selected from 2-quinolinyl and 3,5-dimethylpyridin-2-yl.

In an additional embodiment, Z is selected from 2-quinolinyl and 6-fluoroquinolin-2-yl.

In an additional embodiment, Z is 2-quinolinyl.

In another embodiment, Z is heteroaryl consisting of 6 ring atoms selected from C and N provided the total number of ring nitrogens is less than or equal to two; said ring is optionally substituted with up to 2 substituents independently selected from alkyl, alkoxy, cycloalkyl, cycloalkyloxy, cycloalkylalkyl, cycloalkylalkoxy, halogen, alkylsulfonyl and cyano and nitro.

In another embodiment, Z is heteroaryl consisting of 6 ring atoms selected from C and N provided the total number of ring nitrogens is less than or equal to two.

In a further embodiment, Z is pyridinyl optionally substituted with up to 2 substituents independently selected from alkyl, alkoxy, cycloalkyl, cycloalkyloxy, cycloalkylalkyl, cycloalkylalkoxy, halogen, alkylsulfonyl, cyano and nitro.

In a further embodiment, Z is 2-pyridinyl optionally substituted with up to 2 substituents independently selected from alkyl, alkoxy, cycloalkyl, cycloalkyloxy, cycloalkylalkyl, cycloalkylalkoxy, halogen, alkylsulfonyl and cyano and nitro.

In a further embodiment, any Z is substituent may be unsubstituted.

In one embodiment, $R_{1a}$ is selected from cycloalkyl and alkyl with the proviso that $R_{1b}$ is hydrogen.

In another embodiment, $R_{1a}$ is selected from hydrogen and alkyl with the proviso that $R_{1b}$ is hydrogen when $R_{1a}$ is alkyl.

In an additional embodiment, $R_{1a}$ is cycloalkyl with the proviso that $R_{1b}$ is hydrogen.

In another embodiment, $R_{1a}$ is alkyl with the proviso that $R_{1b}$ is hydrogen In another embodiment, $R_{1a}$ is fully saturated $C_1$-$C_4$ alkyl with the proviso that $R_{1b}$ is hydrogen In another embodiment, $R_{1a}$ is hydrogen.

In one embodiment, $R_{1b}$ is selected from cycloalkyl and alkyl with the proviso that $R_{1a}$ is hydrogen.

In one embodiment, $R_{1b}$ is selected from hydrogen and alkyl with the proviso that $R_{1a}$ is hydrogen when $R_{1b}$ is alkyl.

In one embodiment, $R_{1b}$ is selected from hydrogen and fully saturated $C_1$-$C_4$ alkyl with the proviso that $R_{1a}$ is hydrogen when $R_{1b}$ is alkyl.

In another embodiment, $R_{1b}$ is cycloalkyl with the proviso that $R_{1a}$ is hydrogen.

In a further embodiment, $R_{1b}$ is alkyl with the proviso that $R_{1a}$ is hydrogen.

In another embodiment, $R_{1b}$ is hydrogen.

In one embodiment, each $R_2$ is independently selected from hydrogen, alkyl, cycloalkyl and cycloalkylalkyl with the proviso that at least one $R_2$ is hydrogen;

In another embodiment, each $R_2$ is independently selected from hydrogen, alkyl and cycloalkyl with the proviso that at least one $R_2$ is hydrogen;

In another embodiment, each $R_2$ is independently selected from hydrogen and alkyl with the proviso that at least one $R_2$ is hydrogen.

In another embodiment, each $R_2$ is independently selected from hydrogen and fully saturated $C_1$-$C_4$ alkyl with the proviso that at least one $R_2$ is hydrogen.

In an additional embodiment, each $R_2$ is hydrogen.

In one embodiment, $R_3$ and $R_4$ are independently selected from hydrogen and cycloalkyl with the proviso that at least one $R_3$ or $R_4$ group must be hydrogen;

In a further embodiment, $R_3$ and $R_4$ are independently selected from hydrogen and $C_1$-$C_4$ alkyl with the proviso that at least one $R_3$ or $R_4$ group must be hydrogen;

In a further embodiment, $R_3$ and $R_4$ are hydrogen.

In one embodiment, $R_5$ is selected from cycloalkylalkyl and alkoxyalkyl.

In an additional embodiment, $R_5$ is selected from cycloalkyl and alkyl.

In another embodiment, $R_5$ is cycloalkyl.

In another embodiment, R$_5$ is alkyl.
In one embodiment n is 1.
In another embodiment n is 2.
In one embodiment, R$_7$ is selected from hydrogen, alkyl, cycloalkyl, cycloalkylalkyl and alkoxyalkyl.
In another embodiment, R$_7$ is selected from alkyl, cycloalkyl, cycloalkylalkyl and alkoxyalkyl.
In another embodiment, R$_7$ is selected from hydrogen, alkyl, cycloalkyl and cycloalkylalkyl.
In another embodiment, R$_7$ is selected from alkyl, cycloalkyl and cycloalkylalkyl.
In another embodiment, R$_7$ is selected from cycloalkyl and cycloalkylalkyl.
In another embodiment, R$_7$ is selected from alkyl and cycloalkyl.
In another embodiment, R$_7$ is alkyl.
In another embodiment, R$_7$ is cycloalkyl.
In another embodiment, R$_7$ is cycloalkylalkyl.
In a further embodiment, R$_7$ is hydrogen.

Compounds of the disclosure may contain asymmetric centers and exist as different enantiomers or diastereomers or a combination of these therein. All enantiomeric, diastereomeric forms of Formulas (I), (II) and (III) are embodied herein.

Compounds in the disclosure may be in the form of pharmaceutically acceptable salts. The phrase "pharmaceutically acceptable" refers to salts prepared from pharmaceutically acceptable non-toxic bases and acids, including inorganic and organic bases and inorganic and organic acids. Salts derived from inorganic bases include lithium, sodium, potassium, magnesium, calcium and zinc. Salts derived from organic bases include ammonia, primary, secondary and tertiary amines, and amino acids. Salts derived from inorganic acids include sulfuric, hydrochloric, phosphoric, hydrobromic. Salts derived from organic acids include C$_{1-6}$ alkyl carboxylic acids, di-carboxylic acids and tricarboxylic acids such as acetic acid, proprionic acid, fumaric acid, maleic acid, succinic acid, tartaric acid, adipic acid and citric acid, and alkylsulfonic acids such as methanesulphonic, and aryl sulfonic acids such as para-tolouene sulfonic acid and benzene sulfonic acid.

Compounds in the disclosure may be in the form of a solvate. This occurs when a compound of Formulas (I) or (II) or (III) has an energetically favorable interaction with a solvent, crystallizes in a manner that it incorporates solvent molecules into the crystal lattice or a complex is formed with solvent molecules in the solid or liquid state. Examples of solvents forming solvates are water (hydrates), MeOH, EtOH, iPrOH, and acetone.

Compounds in the disclosure may exist in different crystal forms known as polymorphs. Polymorphism is the ability of a substance to exist in two or more crystalline phases that have different arrangements and/or conformations of the molecule in the crystal lattice.

Compounds in the disclosure may exist as isotopically labeled compounds of Formulas (I) or (II) or (III) where one or more atoms are replaced by atoms having the same atomic number but a different atomic mass from the atomic mass which is predominantly seen in nature. Examples of isotopes include, but are not limited to hydrogen isotopes (deuterium, tritium), carbon isotopes ($^{11}$C, $^{13}$C, $^{14}$C) and nitrogen isotopes ($^{13}$N, $^{15}$N). For example, substitution with heavier isotopes such as deuterium ($^2$H) may offer certain therapeutic advantages resulting from greater metabolic stability which could be preferable and lead to longer in vivo half-life or dose reduction in a mammal or human.

Prodrugs of compounds embodied by Formulas (I) or (II) or (III) are also within the scope of this disclosure. Particular derivatives of compounds of Formulas (I) or (II) or (III) which may have little to negligible pharmacological activity themselves, can, when administered to a mammal or human, be converted into compounds of Formulas (I) or (II) or (III) having the desired biological activity.

Compounds in the disclosure and their pharmaceutically acceptable salts, prodrugs, as well as metabolites of the compounds, may also be used to treat certain eating disorders, obesity, compulsive gambling, sexual disorders, narcolepsy, sleep disorders, diabetes, metabolic syndrome, neurodegenerative disorders and CNS disorders/conditions as well as in smoking cessation treatment.

In one embodiment the treatment of CNS disorders and conditions by the compounds of the disclosure can include Huntington's disease, schizophrenia and schizo-affective conditions, delusional disorders, drug-induced psychoses, panic and obsessive compulsive disorders, post-traumatic stress disorders, age-related cognitive decline, attention deficit/hyperactivity disorder, bipolar disorders, personality disorders of the paranoid type, personality disorders of the schizoid type, psychosis induced by alcohol, amphetamines, phencyclidine, opioids hallucinogens or other drug-induced psychosis, dyskinesia or choreiform conditions including dyskinesia induced by dopamine agonists, dopaminergic therapies, psychosis associated with Parkinson's disease, psychotic symptoms associated with other neurodegenerative disorders including Alzheimer's disease, dystonic conditions such as idiopathic dystonia, drug-induced dystonia, torsion dystonia, and tardive dyskinesia, mood disorders including major depressive episodes, post-stroke depression, minor depressive disorder, premenstrual dysphoric disorder, dementia including but not limited to multi-infarct dementia, AIDS-related dementia, and neurodegenerative dementia, In another embodiment, compounds of the disclosure may be used for the treatment of eating disorders, obesity, compulsive gambling, sexual disorders, narcolepsy, sleep disorders as well as in smoking cessation treatment.

In a further embodiment, compounds of the disclosure may be used for the treatment of obesity, schizophrenia, schizo-affective conditions, Huntington's disease, dystonic conditions and tardive dyskinesia.

In another embodiment, compounds of the disclosure may be used for the treatment of schizophrenia, schizo-affective conditions, Huntington's disease and obesity.

In a further embodiment, compounds of the disclosure may be used for the treatment of schizophrenia and schizo-affective conditions.

In an additional embodiment, compounds of the disclosure may be used for the treatment of Huntington's disease.

In another embodiment, compounds of the disclosure may be used for the treatment of obesity and metabolic syndrome.

Compounds of the disclosure may also be used in mammals and humans in conjunction with conventional antipsychotic medications including but not limited to Clozapine, Olanzapine, Risperidone, Ziprasidone, Haloperidol, Aripiprazole, Sertindole and Quetiapine. The combination of a compound of Formula (I) or (II) or (III) with a subtherapeutic dose of an aforementioned conventional antipsychotic medication may afford certain treatment advantages including improved side effect profiles and lower dosing requirements.

DEFINITIONS

Alkyl is a linear or branched saturated or unsaturated aliphatic C$_1$-C$_8$ hydrocarbon which can be optionally substituted with up to 3 fluorine atoms. Unsaturation in the form of a double or triple carbon-carbon bond may be internal or terminally located and in the case of a double bond both cis and trans isomers are included. Examples of alkyl groups include but are not limited to methyl, trifluoromethyl, ethyl, trifluoroethyl, isobutyl, neopentyl, cis- and trans-2-butenyl, isobutenyl, propargyl. $C_1$-$C_4$ alkyl is the subset of alkyl limited to a total of up to 4 carbon atoms.

In each case in which a size range for the number of atoms in a ring or chain is disclosed, all subsets are disclosed. Thus, $C_x$-$C_y$ includes all subsets, e.g., $C_1$-$C_4$ includes $C_1$-$C_2$, $C_2$-$C_4$, $C_1$-$C_3$ etc.

Acyl is an alkyl-C(O)— group wherein alkyl is as defined above. Examples of acyl groups include acetyl and proprionyl.

Alkoxy is an alkyl-O— group wherein alkyl is as defined above. $C_1$-$C_4$ alkoxy is the subset of alkyl-O— where the subset of alkyl is limited to a total of up to 4 carbon atoms. Examples of alkoxy groups include methoxy, trifluoromethoxy, ethoxy, trifluoroethoxy, and propoxy Alkoxyalkyl is an alkyl-O—($C_1$-$C_4$ alkyl)-group wherein alkyl is as defined above. Examples of alkoxyalkyl groups include methoxymethyl and ethoxymethyl.

Alkoxyalkyloxy is an alkoxy-alkyl-O— group wherein alkoxy and alkyl are as defined above. Examples of alkoxyalkyloxy groups include methoxymethyloxy ($CH_3OCH_2O$—) and methoxyethyloxy ($CH_3OCH_2CH_2O$—) groups.

Alkylthio is alkyl-S— group wherein alkyl is as defined above.

Alkylsulfonyl is alkyl-$SO_2$— wherein alkyl is as defined above.

Alkylamino is alkyl-NH— wherein alkyl is as defined above. Dialkylamino is $(alkyl)_2$-N— wherein alkyl is as defined above.

Amido is $H_2NC(O)$—

Alkylamido is alkyl-NHC(O)— wherein alkyl is as defined above.

Dialkylamido is $(alkyl)_2$-NC(O)— wherein alkyl is as defined above.

Aromatic is heteroaryl or aryl wherein heteroaryl and aryl are as defined below.

Aryl is a phenyl or napthyl group. Aryl groups may be optionally and independently substituted with up to three groups selected from halogen, $CF_3$, CN, $NO_2$, OH, alkyl, cycloalkyl, cycloalkylalkyl, alkoxy, alkoxyalkyl, aryloxy, alkoxyalkyloxy, heterocycloalkyl, heterocycloalkylalkyl, heterocycloalkyloxy, heteroaryl, heteroaryloxy, —$OCH_2CH_2OCH_3$, —$OC(O)R_a$, —$OC(O)OR_a$, —$OC(O)NHR_a$, —$OC(O)N(R_a)$, —$SR_a$, —$S(O)R_a$, —$NH_2$, —$NHR_a$, —$N(R_a)(R_b)$, —$NHC(O)R_a$, —$N(R_a)C(O)R_b$, —$NHC(O)OR_a$, —$N(R_a)C(O)OR_b$, —$N(R_a)C(O)NH(R_b)$, —$N(R_a)C(O)NH(R_b)_2$, —$C(O)NH_2$, —$C(O)NHR_a$, —$C(O)N(R_a)(R_b)$, —$CO_2H$, —$CO_2R_a$, —$COR_a$ wherein $R_a$ and $R_b$ are independently chosen from alkyl, alkoxyalkyl, —$CH_2CH_2OH$, —$CH_2CH_2OMe$, cycloalkyl, cycloalkylalkyl, aryl, arylalkyl, heteroaryl, heteroarylalkyl, heterocycloalkyl, and heterocycloalkylalkyl, each of which is optionally and independently substituted with up to three groups selected from only halogen, Me, Et, $^iPr$, $^tBu$, unsubstituted cyclopropyl, unsubstituted cyclobutyl, CN, $NO_2$, $NH_2$, $CF_3$, NHMe, $NMe_2$, OMe, $OCF_3$, each of which are attached via carbon-carbon or carbon-nitrogen or carbon-oxygen single bonds; or $R_a$ and $R_b$ taken together with the atom(s) to which they are attached form a 5-6 membered ring.

Arylalkyl is an aryl-alkyl-group wherein aryl and alkyl are as defined above.

Aryloxy is an aryl-O— group wherein aryl is as defined above.

Arylalkoxy is an aryl-($C_1$-$C_4$ alkyl)-O— group wherein aryl is as defined above.

Carboxy is a $CO_2H$ or $CO_2R_c$ group wherein $R_c$ is independently chosen from, alkyl, $C_1$-$C_4$ alkyl, cycloalkyl, arylalkyl, cycloalkylalkyl, $CF_3$, and alkoxyalkyl, wherein alkyl is as defined above.

Cycloalkyl is a $C_3$-$C_7$ cyclic non-aromatic hydrocarbon which may contain a single double bond and is optionally and independently substituted with up to three groups selected from alkyl, alkoxy, hydroxyl and oxo. Examples of cycloalkyl groups include cyclopropyl, cyclobutyl, cyclopentyl, cyclohexyl, cyclopentenyl and cyclohexanonyl.

Cycloalkyloxy is a cycloalkyl-O— group wherein cycloalkyl is as defined above. Examples include cyclopropyloxy, cyclobutyloxy and cyclopentyloxy. $C_3$-$C_6$ cycloalkyloxy is the subset of cycloalkyl-O— where cycloalkyl contains 3-6 carbon atoms.

Cycloalkylalkyl is a cycloalkyl-($C_1$-$C_4$ alkyl)-group. Examples include cyclopropylmethyl, cyclopropylethyl, cyclohexylmethyl and cyclohexylethyl.

Cycloalkylalkoxy is a cycloalkyl-($C_1$-$C_4$ alkyl)-O— group wherein cycloalkyl and alkyl are as defined above. Examples of cycloalkylalkoxy groups include cyclopropylmethoxy, cyclopentylmethoxy and cyclohexylmethoxy.

Halogen is F, Cl, Br or I.

Heteroaryl is a tetrazole, 1,2,3,4-oxatriazole, 1,2,3,5-oxatriazole, a mono or bicyclic aromatic ring system, or a heterobicyclic ring system with one aromatic ring having 5 to 10 ring atoms independently selected from C, N, O and S, provided that not more than 3 ring atoms in any single ring are other than C. Examples of heteroaryl groups include but are not limited to thiophenyl, furanyl, thiazolyl, isothiazolyl, oxazolyl, isoxazolyl, 1,2,4-oxadiazolyl, 1,3,4-oxadiazolyl, pyrrazolyl, imidazolyl, 1,2,3-triazolyl, 1,3,4-triazolyl, pyrimidinyl, pyrazinyl, indolyl, quinolyl, tetrahydroquinolyl, isoquinolyl, tetrahydroisoquinolyl, indazolyl, benzthiadiazololyl, benzoxadiazolyl and benzimidazolyl. Heteroaryl groups may be optionally and independently substituted with up to 3 substituents independently selected from halogen, $CF_3$, CN, $NO_2$, OH, alkyl, cycloalkyl, cycloalkylalkyl, alkoxy, alkoxyalkyl, aryloxy, alkoxyalkyloxy, heterocycloalkyl, heterocycloalkylalkyl, heterocycloalkyloxy, heteroaryl, heteroaryloxy, —$OCH_2CH_2OCH_3$, —$OC(O)R_a$, —$OC(O)OR_a$, —$OC(O)NHR_a$, —$OC(O)N(R_a)$, —$SR_a$, —$S(O)R_a$, —$NH_2$, —$NHR_a$, —$N(R_a)(R_b)$, —$NHC(O)R_a$, —$N(R_a)C(O)R_b$, —$NHC(O)OR_a$, —$N(R_a)C(O)OR_b$, —$N(R_a)C(O)NH(R_b)$, —$N(R_a)C(O)NH(R_b)_2$, —$C(O)NH_2$, —$C(O)NHR_a$, —$C(O)N(R_a)(R_b)$, —$CO_2H$, —$CO_2R_a$, —$COR_a$ wherein $R_a$ and $R_b$ are independently chosen from alkyl, alkoxyalkyl, —$CH_2CH_2OH$, —$CH_2CH_2OMe$, cycloalkyl, cycloalkylalkyl, aryl, arylalkyl, heteroaryl, heteroarylalkyl, heterocycloalkyl, and heterocycloalkylalkyl, each of which is optionally and independently substituted with up to three groups selected from only halogen, Me, Et, $^iPr$, $^tBu$, unsubstituted cyclopropyl, unsubstituted cyclobutyl, CN, $NO_2$, $NH_2$, $CF_3$, NHMe, $NMe_2$, OMe, $OCF_3$, each of which are attached via carbon-carbon or carbon-nitrogen or carbon-oxygen single bonds; or $R_a$ and $R_b$ taken together with the atom(s) to which they are attached form a 5-6 membered ring.

Heteroarylalkyl is a heteroaryl-($C_1$-$C_4$ alkyl)-group wherein heteroaryl and alkyl are as defined above. Examples of heteroarylalkyl groups include 4-pyridinylmethyl and 4-pyridinylethyl.

Heteroaryloxy is a heteroaryl-O group wherein heteroaryl is as defined above.

Heteroarylalkoxy is a heteroaryl-($C_1$-$C_4$ alkyl)-O— group wherein heteroaryl and alkoxy are as defined above. Examples of heteroarylalkyl groups include 4-pyridinylmethoxy and 4-pyridinylethoxy.

Heterobicyclic ring system is a ring system having 8-10 atoms independently selected from C, N, O and S, provided that not more than 3 ring atoms in any single ring are other than carbon and provided that at least one of the rings is aromatic; said bicyclic ring may be optionally and independently substituted with up to 3 substituents independently selected from alkyl, alkoxy, cycloalkyl, $C_3$-$C_6$ cycloalkyloxy, cycloalkylalkyl, halogen, nitro, alkylsulfonyl and cyano. Examples of 8-10 membered heterobicyclic ring systems include but are not limited to 1,5-naphthyridyl, 1,2,3,4-tetrahydro-1,5-naphthyridyl 1,6-naphthyridyl, 1,2,3,4-tetrahydro-1,6-naphthyridyl 1,7-naphthyridyl, 1,2,3,4-tetrahydro-1,7-naphthyridinyl 1,8-naphthyridyl, 1,2,3,4-tetrahydro-1,8-naphthyridyl, 2,6-naphthyridyl, 2,7-naphthyridyl, cinnolyl, isoquinolyl, tetrahydroisoquinolinyl, phthalazyl, quinazolyl, 1,2,3,4-tetrahydroquinazolinyl, quinolyl, tetrahydroquinolinyl, quinoxalyl, tetrahydroquinoxalinyl, benzo[d][1,2,3]triazyl, benzo[e][1,2,4]triazyl, pyrido[2,3-b]pyrazyl, pyrido[2,3-c]pyridazyl, pyrido[2,3-d]pyrimidyl, pyrido[3,2-b]pyrazyl, pyrido[3,2-c]pyridazyl, pyrido[3,2-d]pyrimidyl, pyrido[3,4-b]pyrazyl, pyrido[3,4-c]pyridazyl, pyrido[3,4-d]pyrimidyl, pyrido[4,3-b]pyrazyl, pyrido[4,3-c]pyridazyl, pyrido[4,3-d]pyrimidyl, quinazolyl, 1H-benzo[d][1,2,3]triazoyl, 1H-benzo[d]imidazoyl, 1H-indazoyl, 1H-indoyl, 2H-benzo[d][1,2,3]triazoyl, 2H-pyrazolo[3,4-b]pyridinyl, 2H-pyrazolo[4,3-b]pyridinyl, [1,2,3]triazolo[1,5-a]pyridinyl, [1,2,4]triazolo[1,5-a]pyridinyl, [1,2,4]triazolo[4,3-a]pyridinyl, benzo[b]thienyl, benzo[c][1,2,5]oxadiazyl, benzo[c][1,2,5]thiadiazolyl, benzo[d]isothiazoyl, benzo[d]isoxazoyl, benzo[d]oxazoyl, benzo[d]thiazoyl, benzofuryl, imidazo[1,2-a]pyrazyl, imidazo[1,2-a]pyridinyl, imidazo[1,2-a]pyrimidyl, imidazo[1,2-b]pyridazyl, imidazo[1,2-c]pyrimidyl, imidazo[1,5-a]pyrazyl, imidazo[1,5-a]pyridinyl, imidazo[1,5-a]pyrimidyl, imidazo[1,5-b]pyridazyl, imidazo[1,5-c]pyrimidyl, indolizyl, pyrazolo[1,5-a]pyrazyl, pyrazolo[1,5-a]pyridinyl, pyrazolo[1,5-a]pyrimidyl, pyrazolo[1,5-b]pyridazine, pyrazolo[1,5-c]pyrimidine, pyrrolo[1,2-a]pyrazine, pyrrolo[1,2-a]pyrimidyl, pyrrolo[1,2-b]pyridazyl, pyrrolo[1,2-c]pyrimidyl, 1H-imidazo[4,5-b]pyridinyl, 1H-imidazo[4,5-c]pyridinyl, 1H-pyrazolo[3,4-b]pyridinyl, 1H-pyrazolo[3,4-c]pyridinyl, 1H-pyrazolo[4,3-b]pyridinyl, 1H-pyrazolo[4,3-c]pyridinyl, 1H-pyrrolo[2,3-b]pyridinyl, 1H-pyrrolo[2,3-c]pyridinyl, 1H-pyrrolo[3,2-b]pyridinyl, 1H-pyrrolo[3,2-c]pyridinyl, 2H-indazoyl, 3H-imidazo[4,5-b]pyridinyl, 3H-imidazo[4,5-c]pyridinyl, benzo[c]isothiazyl, benzo[c]isoxazyl, furo[2,3-b]pyridinyl, furo[2,3-c]pyridinyl, furo[3,2-b]pyridinyl, furo[3,2-c]pyridiyl, isothiazolo[4,5-b]pyridinyl, isothiazolo[4,5-c]pyridinyl, isothiazolo[5,4-b]pyridinyl, isothiazolo[5,4-c]pyridinyl, isoxazolo[4,5-b]pyridinyl, isoxazolo[4,5-c]pyridinyl, isoxazolo[5,4-b]pyridinyl, isoxazolo[5,4-c]pyridinyl, oxazolo[4,5-b]pyridinyl, oxazolo[4,5-c]pyridinyl, oxazolo[5,4-b]pyridinyl, oxazolo[5,4-c]pyridinyl, thiazolo[4,5-b]pyridiyl, thiazolo[4,5-c]pyridinyl, thiazolo[5,4-b]pyridinyl, thiazolo[5,4-c]pyridinyl, thieno[2,3-b]pyridinyl, thieno[2,3-c]pyridinyl, thieno[3,2-b]pyridinyl and thieno[3,2-c]pyridinyl.

Heterocycloalkyl is a non-aromatic, monocyclic or bicyclic saturated or partially unsaturated ring system comprising 5-10 ring atoms selected from C, N, O and S, provided that not more than 2 ring atoms in any single ring are other than C. In the case where the heterocycloalkyl group contains a nitrogen atom the nitrogen may be substituted with an alkyl, acyl, —C(O)O-alkyl, —C(O)NH(alkyl) or a —C(O)N(alkyl)$_2$ group. Heterocycloalkyl groups may be optionally and independently substituted with hydroxy, alkyl, cycloalkyl, cycloalkylalkyl and alkoxy groups and may contain up to two oxo groups. Heterocycloalkyl groups may be linked to the rest of the molecule via either carbon or nitrogen ring atoms. Examples of heterocycloalkyl groups include tetrahydrofuranyl, tetrahydrothienyl, tetrahydro-2H-pyran, tetrahydro-2H-thiopyranyl, pyrrolidinyl, pyrrolidonyl, succinimidyl, piperidinyl, piperazinyl, N-methylpiperazinyl, morpholinyl, morpholin-3-one, thiomorpholinyl, thiomorpholin-3-one, 2,5-diazabicyclo[2.2.2]octanyl, 2,5-diazabicyclo[2.2.1]heptanyl, octahydro-1H-pyrido[1,2-a]pyrazine, 3-thia-6-azabicyclo[3.1.1]heptane and 3-oxa-6-azabicyclo[3.1.1]heptanyl Heterocycloalkylalkyl is a heterocycloalkyl-($C_1$-$C_4$ alkyl)-group wherein heterocycloalkyl is as defined above.

Heterocycloalkyloxy is a heterocycloalkyl-O— group wherein heterocycloalkyl is as defined above.

Heterocycloalkylalkoxy is a heterocycloalkyl-($C_1$-$C_4$ alkyl)-O— group wherein heterocycloalkyl is as defined above.

Oxo is a —C(O)— group.

Phenyl is a benzene ring which may be optionally and independently substituted with up to three groups selected from halogen, $CF_3$, CN, $NO_2$, OH, alkyl, cycloalkyl, cycloalkylalkyl, alkoxy, alkoxyalkyl, aryloxy, alkoxyalkyloxy, heterocycloalkyl, heterocycloalkylalkyl, heterocycloalkyloxy, heteroaryl, heteroaryloxy, —$OCH_2CH_2OCH_3$, —$OC(O)R_a$, —$OC(O)OR_a$, —$OC(O)NHR_a$, —$OC(O)N(R_a)$, —$SR_a$, —$S(O)R_a$, —$NH_2$, —$NHR_a$, —$N(R_a)(R_b)$, —$NHC(O)R_a$, —$N(R_a)C(O)R_b$, —$NHC(O)OR_a$, —$N(R_a)C(O)OR_b$, —$N(R_a)C(O)NH(R_b)$, —$N(R_a)C(O)NH(R_b)_2$, —$C(O)NH_2$, —$C(O)NHR_a$, —$C(O)N(R_a)(R_b)$, —$CO_2H$, —$CO_2R_a$, —$COR_a$ wherein $R_a$ and $R_b$ are independently chosen from alkyl, alkoxyalkyl, —$CH_2CH_2OH$, —$CH_2CH_2OMe$, cycloalkyl, cycloalkylalkyl, aryl, arylalkyl, heteroaryl, heteroarylalkyl, heterocycloalkyl, and heterocycloalkylalkyl, each of which is optionally and independently substituted with up to three groups selected from only halogen, Me, Et, $^iPr$, $^tBu$, unsubstituted cyclopropyl, unsubstituted cyclobutyl, CN, $NO_2$, $NH_2$, $CF_3$, NHMe, NMe$_2$, OMe, OCF$_3$, each of which are attached via carbon-carbon or carbon-nitrogen or carbon-oxygen single bonds; or $R_a$ and $R_b$ taken together with the atom(s) to which they are attached form a 5-6 membered ring.

Restricted phenyl is a benzene ring which may be optionally and independently substituted with up to three groups selected from halogen, $CF_3$, CN, alkoxy, alkoxyalkyl, aryloxy, alkoxyalkyloxy, heterocycloalkyl, heterocycloalkyloxy, heteroaryl, heteroaryloxy, —$OCH_2CH_2OCH_3$, —$OC(O)R_a$, —$OC(O)OR_a$, —$OC(O)N(R_a)$, —$N(R_a)(R_b)$, —$NHC(O)R_a$, —$N(R_a)C(O)R_b$, —$NHC(O)OR_a$, —$N(R_a)C(O)OR_b$, —$C(O)N(R_a)(R_b)$, —$COR_a$ wherein $R_a$ and $R_b$ are independently chosen from alkyl, alkoxyalkyl, —$CH_2CH_2OH$, —$CH_2CH_2OMe$, cycloalkyl, cycloalkylalkyl, aryl, arylalkyl, heteroaryl, heteroarylalkyl, heterocycloalkyl, and heterocycloalkylalkyl, each of which is optionally and independently substituted with up to three groups selected from only halogen, Me, Et, $^iPr$, $^tBu$, unsubstituted cyclopropyl, unsubstituted cyclobutyl, CN, $NO_2$, $NH_2$, $CF_3$, NHMe, NMe$_2$, OMe, OCF$_3$, each of which are attached via carbon-carbon or carbon-nitrogen or carbon-oxygen single bonds; or $R_a$ and $R_b$ taken together with the atom(s) to which they are attached form a 5-6 membered ring.

Abbreviations used in the following examples and preparations include:

Ac Acyl (Me-C(O)—)
AcN Acetonitrile
BINAP 2,2'-bis(diphenylphosphino)-1,1'-binaphthyl
Bn Benzyl
Celite® Diatomaceous earth
DBU 1,8-Diazabicyclo[5.4.0]undec-7-ene
DCC N,N', Dicyclohexylcarbodiimide
DCM Dichloromethane
DIEA Di-isopropylethyl amine
DIPEA Di-isopropylethyl amine
DMAP 4-Dimethylaminopyridine
DMF Dimethylformamide
DMP Dess Martin Periodinane
DMSO Dimethyl sulfoxide
Dppf 1,4-Bis(diphenylphosphino) ferrocene
EDC 1-(3-Dimethylaminopropyl)-3-ethylcarbodiimide Hydrochloride
$Et_3N$ Triethylamine
g gram(s)
h Hour(s)
hr Hour(s)
HATU 2-(7-Aza-1H-benzotriazole-1-yl)-1,1,3,3-tetramethyluronium hexafluorophosphate
HMDS Hexamethyldisilazide
HOBt 1-Hydroxybenzotriazole
HPLC High Pressure Liquid Chromatography
HRMS High resolution mass spectrometry
i.v. Intravenous
KHMDS Potassium Hexamethydisilazide
LDA Lithium Di-isopropylamide
m Multiplet
m- meta
mCPBA meta-chloroperbenzoic acid
MEM Methoxyethoxymethyl
MeOH Methyl Alcohol or Methanol
min Minute(s)
mmol millimoles
mmole millimoles
Ms Mesylate
MS Mass Spectrometry
MW Molecular Weight
NBS N-Bromosuccinamide
NCS N-Chlorosuccinamide
NIS N-Iodosuccinamide
NMR Nuclear Magnetic Resonance
NMM N-Methyl Morpholine
NMP N-Methyl-2-pyrrolidone
o ortho
o/n overnight
p para
PCC Pyridinium Chlorochromate
PEPPSI 1,3-Bis(2,6-diisopropylphenyl)imidazolidene)(3-chloropyridinyl) palladium(II)dichloride
$PhNTf_2$ 1,1,1-trifluoro-N-phenyl-N-(trifluoromethylsulfonyl)methanesulfonamide
POPd Dihydrogen dichlorobis(di-tert-butylphosphinito-kp) palladate (2-)
p.s.i. Pounds per square inch
PPA Polyphosphoric acid
PPAA 1-Propanephosphonic Acid Cyclic Anhydride
PTSA p-Toluenesulfonic acid
PyBOP® Benzotriazol-1-yl-oxytripyrrolidinophosphonium hexafluorophosphate
RT (or rt) room temperature (about 20-25° C.)
s Singlet
sat. Saturated
t Triplet
TBAF Tetra-butyl ammonium fluoride
TEA Triethylamine
TFA Trifluoroacetic Acid
THF Tetrahydrofuran
TLC Thin layer chromatography
TMS Trimethylsilyl
Tf Triflate
Tof-MS Time of Flight Mass Spectrometry
Ts Tosylate
v/v volume/volume
wt/v weight/volume

DETAILED DESCRIPTION OF THE DISCLOSURE

The 5- and 6-membered heterocyclic compounds of Formula (I), (II) or (III) may be prepared from multi-step organic synthesis routes from commercially available starting materials by one skilled in the art of organic synthesis using established organic synthesis procedures.

Compounds of the disclosure of Formula (I), (II) or (III) in which X=phenyl, heteroaryl or heterocycloalkyl are as described previously and thus having general Formula XIII may be prepared generally as depicted in Scheme 1.

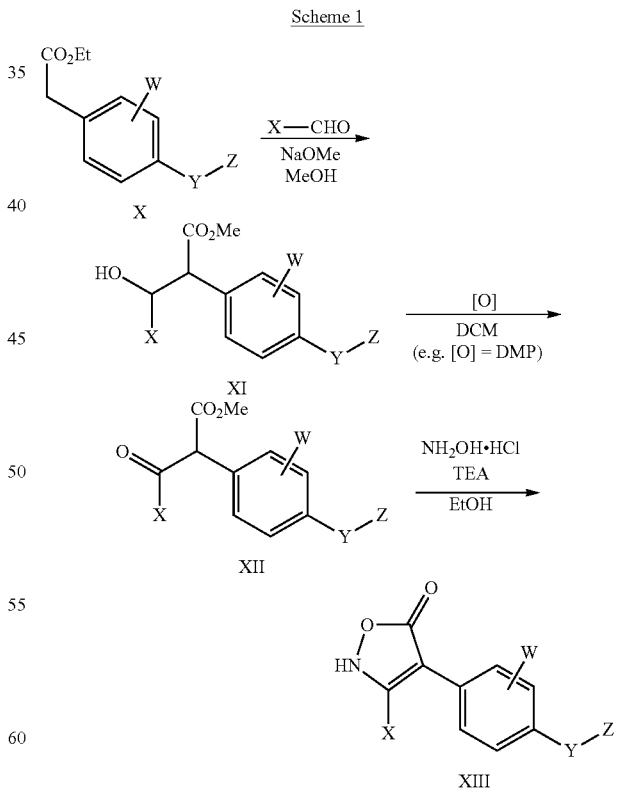

Compounds of the disclosure of Formula (I), (II) or (III) in which X=phenyl, heteroaryl or heterocycloalkyl are as described previously and thus having general Formula XXIII may be prepared generally as depicted in Scheme 2

Scheme 2

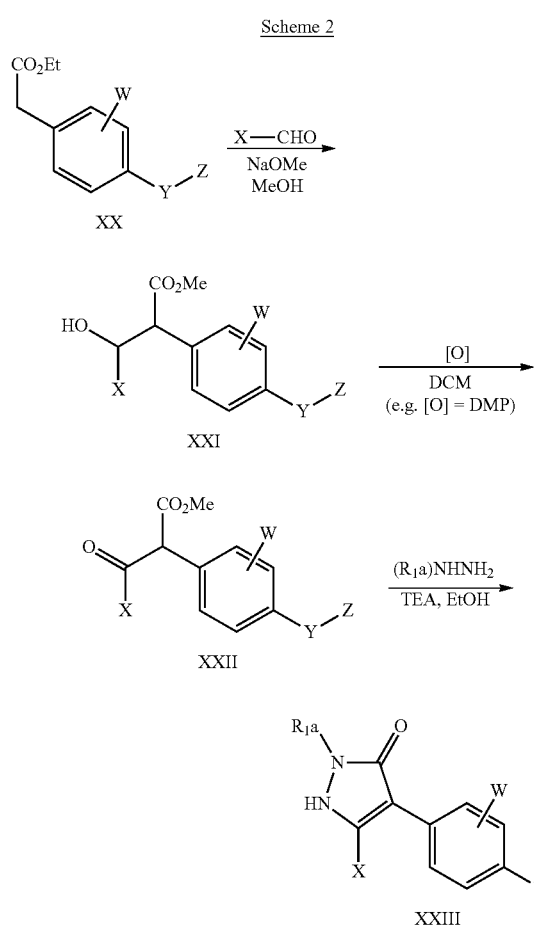

Compounds of the disclosure of Formulas (I), (II) or (III) in which X=aryl, phenyl or heteroaryl are as described previously and thus having general Formula XXXIV may be prepared generally as depicted in Scheme 3.

Scheme 3

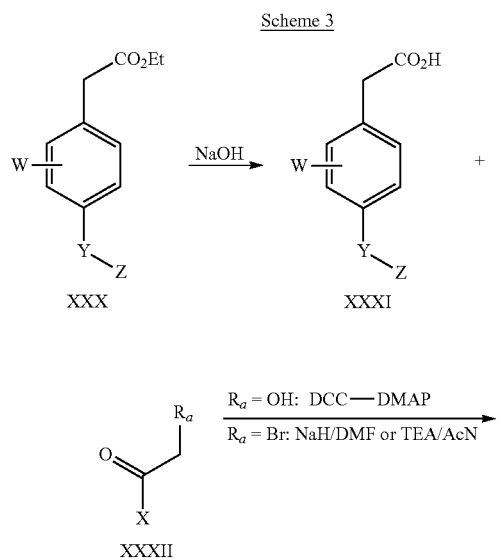

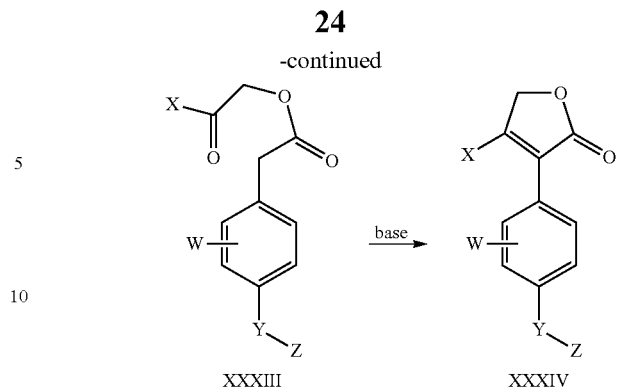

Compounds of the disclosure of Formulas (I), (II) or (III) in which X=heterocycloalkyl are as described previously and thus having general Formula XLIII may be prepared generally as depicted in Scheme 4:

Scheme 4

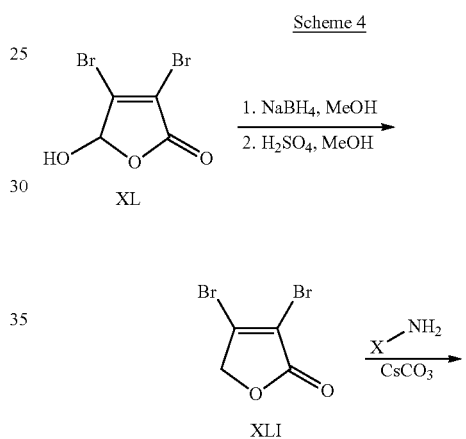

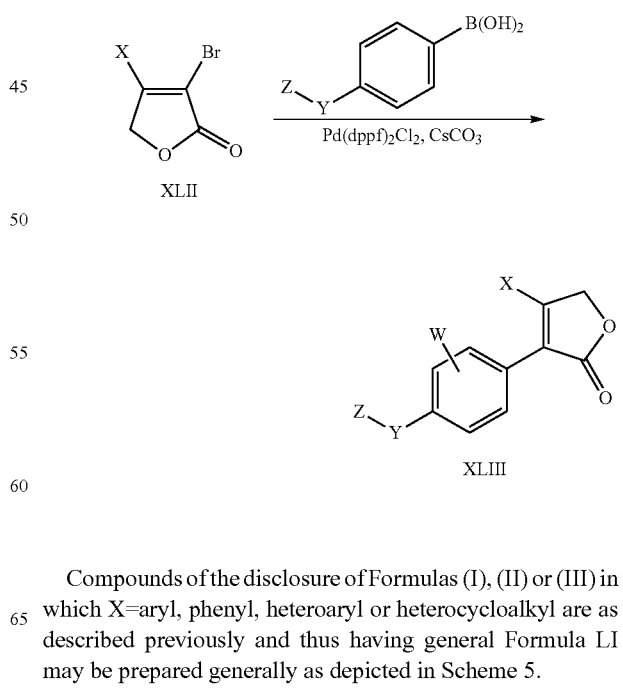

Compounds of the disclosure of Formulas (I), (II) or (III) in which X=aryl, phenyl, heteroaryl or heterocycloalkyl are as described previously and thus having general Formula LI may be prepared generally as depicted in Scheme 5.

Scheme 5

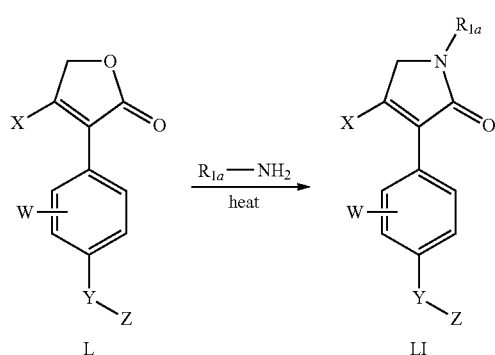

Compounds of the disclosure of Formulas (I), (II) or (III) in which X=phenyl or heteroaryl are as described previously and thus having general Formula LXIII may be prepared generally as depicted in Scheme 6.

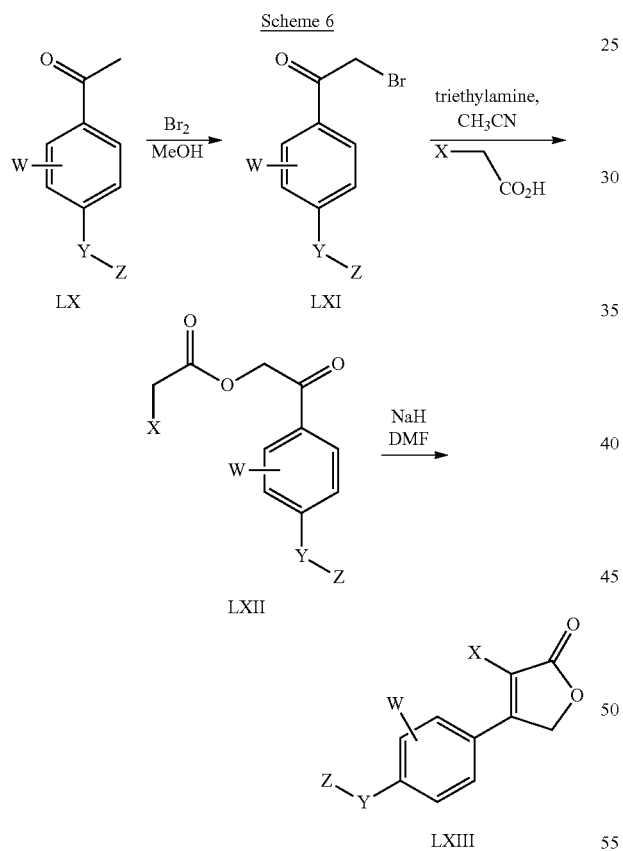

Reactive groups not involved in the above processes can be protected with standard protecting groups during the reactions and removed by standard procedures (T. W. Greene & P. G. M. Wuts, Protecting Groups in Organic Synthesis, Third Edition, Wiley-Interscience) known to those of ordinary skill in the art. Presently preferred protecting groups include methyl, benzyl, MEM, acetate and tetrahydropyranyl for the hydroxyl moiety, and BOC, Cbz, trifluoroacetamide and benzyl for the amino moiety, methyl, ethyl, tert-butyl and benzyl esters for the carboxylic acid moiety Experimental Procedures HPLC Conditions
Condition-A:
Column: Hypersil BDS C8 250×4.6 mm, 5 um (SHCL06E001)
Mobile Phase AcN (A): 0.1% TFA in Water (B).
Flow rate: 1.5 ml/min (Gradient)
Condition-B:
Column: Zobrax SB-C18 250×4.6 mm, 5 um
Mobile Phase AcN (A): 0.1% TFA in Water (B).
Flow rate: 1.5 ml/min (Gradient)
Condition-C:
Column: Targa C-18 250×4.6 mm, 5 um
Mobile Phase AcN (A): 0.1% TFA in Water (B).
Flow rate: 1.5 ml/min (Gradient)
Condition-D:
Column: Targa C18 250×4.6 mm, 5 um (SHCL-12)
Mobile Phase AcN (A): 5M Ammonium Acetate in Water. (B).
Flow rate: 1.0 ml/min (Gradient
Condition-E:
Column: Higgins-C18 250×4.6 mm, 5 um
Mobile Phase AcN (A): 0.1% TFA in Water (B).
Flow rate: 1.5 ml/min (Gradient)
Condition-F:
Column: Chiralpak AD
Mobile Phase: n-Hexane:Ethanol (50:50)
Flow rate: 0.6 ml/min (Gradient)
Condition-G:
Column: Venusil C8, 250×4.6 mm, 5 um.
Mobile Phase AcN (A): 0.1% TFA in Water (B).
Flow rate: 1.5 ml/min (Gradient)
Condition-H:
Column: Eclipse XDB-C18, 150×4.6 mm, 5um.
Mobile Phase: 0.1% TFA in Water (A): AcN (B).
Flow rate: 1.5 ml/min (Gradient)
Condition-I:
Column: Acquity BEH-C18, (50×2.1 mm, 1.7 um.)
Mobile Phase AcN (B)
Flow rate: 0.5 ml/min (Gradient)
Condition-J:
Column: Zobrax C18, (150×4.6 mm, 5 um.)
Mobile Phase AcN (A): 0.1% TFA in Water (B).
Flow rate: 1.0 ml/min (Gradient)

Synthesis of 3-(Pyridin-4-yl)-4-(4-(quinolin-2-yl-methoxy)phenyl)isoxazol-5(2H)-one (Example 1094)

Methyl 3-hydroxy-3-(pyridin-4-yl)-2-(4-(quinolin-2-ylmethoxy)phenyl)propanoate

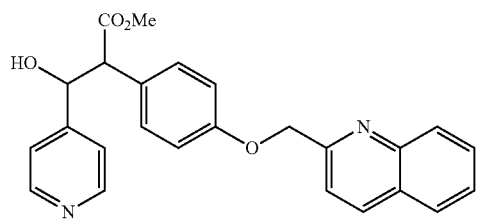 [SMILES: COC(=O)C(c1ccc(OCc2ccc3ccccc3n2)cc1)C(O)c1ccncc1]

To a 0° C. stirred solution of ethyl 2-(4-(quinolin-2-yl-methoxy)phenyl)acetate (1.0 g, 3.1 mmol) in methanol (10 mL), NaOMe (0.185 g, 3.42 mmol) was added slowly. After stirring for 10 minutes, isonicotinaldehyde (0.367 g, 3.42 mmol) was then added and the reaction mixture was stirred at RT for 16 h. The reaction mixture was then quenched with cold water; volatiles were concentrated in vacuo and extracted with EtOAc (2×20 mL). The combined organic layers were washed with water, dried over $Na_2SO_4$, filtered, and concentrated in vacuo to obtain crude product. The crude material was purified via silica gel column chromatography to afford methyl 3-hydroxy-3-(pyridin-4-yl)-2-(4-(quinolin-2-ylmethoxy)phenyl) propanoate (1.02 g, 85%) as a solid.

Methyl 3-oxo-3-(pyridin-4-yl)-2-(4-(quinolin-2-yl-methoxy)phenyl)propanoate

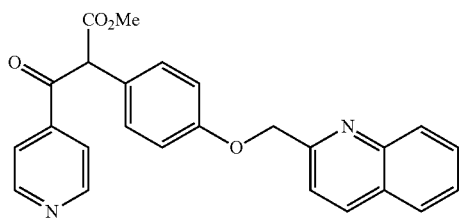 [SMILES: COC(=O)C(C(=O)c1ccncc1)c1ccc(OCc2ccc3ccccc3n2)cc1]

To a stirred solution of 3-hydroxy-3-(pyridin-4-yl)-2-(4-(quinolin-2-ylmethoxy)phenyl) propanoate (0.5 g, 1.2 mmol) in DCM (10 mL) was added Dess-Martin periodinane (1.024 g, 2.4 mmol) at 0° C. The reaction mixture was stirred at RT for 3 h, quenched with a saturated $NaHCO_3$ solution and extracted with EtOAc (2×30 mL). The combined organic layers were washed with water, brine, dried over $Na_2SO_4$, filtered and concentrated in vacuo to obtain the crude product. The crude material was purified via silica gel column chromatography to afford methyl 3-oxo-3-(pyridin-4-yl)-2-(4-(quinolin-2-ylmethoxy)phenyl) propanoate (0.4 g, 80%) as a solid.

3-(Pyridin-4-yl)-4-(4-(quinolin-2-ylmethoxy)phenyl) isoxazol-5(2H)-one (Example 1094)

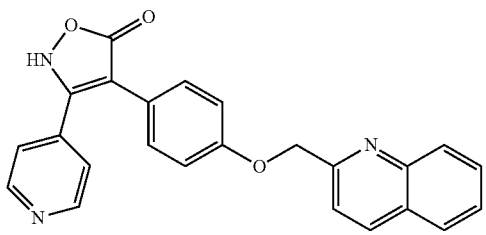 [SMILES: O=c1o[nH]c(-c2ccncc2)c1-c1ccc(OCc2ccc3ccccc3n2)cc1]

To a stirred solution of methyl 3-oxo-3-(pyridin-4-yl)-2-(4-(quinolin-2-ylmethoxy)phenyl) propanoate (100 mg, 0.24 mmol) in ethanol (0.5 mL), $NH_2OH$—HCl (0.083 g, 1.2 mmol) and TEA (0.101 mL, 0.72 mmol) were added to the mixture dropwise. The reaction mixture was then refluxed for 16 h and then concentrated in vacuo to obtain the crude product. The crude material was washed with water and EtOAc to afford 3-(pyridin-4-yl)-4-(4-(quinolin-2-ylmethoxy)phenyl)isoxazol-5(2H)-one (30 mg, 31%) as a solid. $^1$H NMR (500 MHz, $d_6$-DMSO): δ 8.68-8.61 (m, 2H), 8.42-8.38 (m, 1H), 8.02-7.94 (m, 2H), 7.79-7.74 (m, 1H), 7.69-7.64 (m, 1H), 7.62-7.58 (m, 1H), 7.42-7.38 (m, 2H), 7.19-7.14 (m, 2H), 7.01-6.92 (m, 2H), 5.38 (s, 2H), 3.59 (s, 1H). MS: M$^+$H: m/z=396.1. HPLC: 91%, (Condition-B).

Synthesis of 5-(Pyridin-4-yl)-4-(4-(quinolin-2-yl-methoxy)phenyl)-1H-pyrazol-3(2H)-one (Example 1096)

5-(Pyridin-4-yl)-4-(4-(quinolin-2-ylmethoxy)phenyl)-1H-pyrazol-3(2H)-one (Example 1096

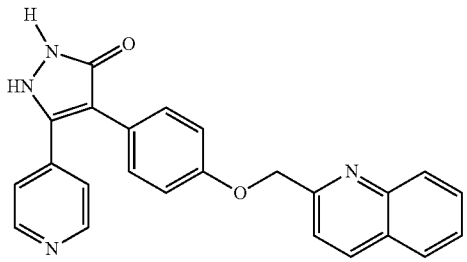 [SMILES: O=c1[nH][nH]c(-c2ccncc2)c1-c1ccc(OCc2ccc3ccccc3n2)cc1]

To a stirred solution of methyl 3-oxo-3-(pyridin-4-yl)-2-(4-(quinolin-2-ylmethoxy)phenyl)propanoate (0.2 g, 0.48 mmol) in ethanol (5 mL), $NH_2NH_2.H_2O$ (0.12 g, 2.42 mmol) and TEA (0.146 g, 1.45 mmol) were added dropwise at RT. The reaction mixture was then refluxed for 16 h and then concentrated in vacuo to obtain crude product. The crude material was washed with water (5 mL) and ether (5 mL) to afford 5-(pyridin-4-yl)-4-(4-(quinolin-2-ylmethoxy)phenyl)-1H-pyrazol-3(2H)-one (70 mg, 37%) as a white solid. $^1$H NMR (500 MHz, $d_6$-DMSO): δ 9.12 (bs, 1H), 8.38 (d, J=7.2 Hz, 2H), 8.02-7.96 (m, 3H), 7.76 (t, J=7.6 Hz, 2H), 7.64-7.56 (m, 3H), 7.16 (d, J=7.2 Hz, 2H), 6.96 (d, J=7.2 Hz, 2H), 5.38 (s, 2H), 3.21 (s, 1H). MS: M$^+$H: m/z=395.1 and HPLC: 80%, (Condition-C).

Synthesis of 2-methyl-5-(pyridin-4-yl)-4-(4-(quinolin-2-ylmethoxy)phenyl)-1H-pyrazol-3(2H)-one (Example 1097)

2-Methyl-5-(pyridin-4-yl)-4-(4-(quinolin-2-yl-methoxy)phenyl)-1H-pyrazol-3(2H)-one (Example 1097)

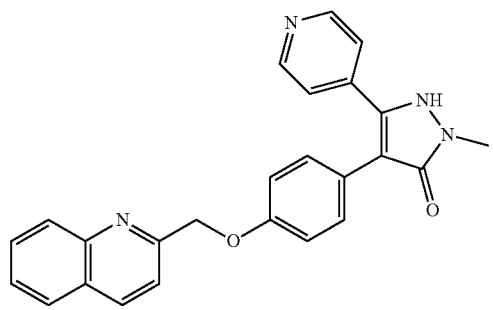 [SMILES: Cn1[nH]c(-c2ccncc2)c(-c2ccc(OCc3ccc4ccccc4n3)cc2)c1=O]

Following the procedure for the preparation of 5-(pyridin-4-yl)-4-(4-(quinolin-2-ylmethoxy)phenyl)-1H-pyrazol-3 (2H)-one using methyl hydrazine provided the title compound. Yield: 15%. $^1$H NMR (500 MHz, $d_6$-DMSO): δ 8.44-8.36 (m, 2H), 8.04-7.96 (m, 2H), 7.82-7.74 (m, 2H), 7.72-7.56 (m, 2H), 7.38-7.22 (m, 1H), 7.18-7.12 (m, 2H), 7.10-

7.06 (m, 1H), 7.01-6.98 (m, 2H), 5.36 (s, 2H), 3.69 (s, 1H), 3.59 (s, 3H). MS: M+H: m/z=409.1.

Synthesis of 4-(Pyridin-3-yl)-3-(4-(quinolin-2-ylmethoxy)phenyl)furan-2(5H)-one (Example 1098)

2-Bromo-1-(pyridin-4-yl)ethanone Hydrobromide

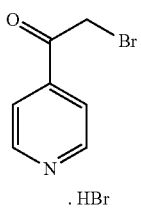

To a stirred solution of 1-(pyridin-4-yl)ethanone (10 g, 0.08 mol) in CCl$_4$ (150 mL) Br$_2$ (3.99 mL, 0.02 mol) was added dropwise at 0° C. The reaction mixture was then refluxed for 1 h, filtered and dried in vacuo to afford 2-bromo-1-(pyridin-4-yl)ethanone hydrobromide (22 g, 94%) as a solid.

Ethyl 2-(4-(quinolin-2-ylmethoxy)phenyl)acetate

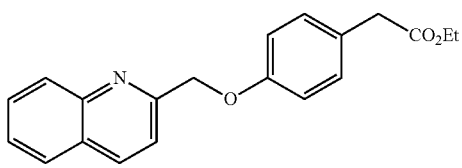 [SMILES: CCOC(=O)Cc1ccc(OCc2ccc3ccccc3n2)cc1]

To a stirred solution of ethyl 2-(4-hydroxyphenyl)acetate (10 g, 0.05 mol) in acetonitrile (150 mL) were added K$_2$CO$_3$ (23 g, 0.16 mol) and 2-(chloromethyl)quinoline (14.2 g, 0.06 mol) under an inert atmosphere. The reaction mixture was then heated at 80° C. for 16 h, diluted with water (50 mL) and extracted with EtOAc (3×100 mL). The combined organic layers were washed with water (100 mL) and brine (100 mL), dried over Na$_2$SO$_4$, filtered, and concentrated in vacuo to afford ethyl 2-(4-(quinolin-2-ylmethoxy)phenyl)acetate (19 g, 95%) as an oil.

2-(4-(Quinolin-2-ylmethoxy)phenyl)acetic Acid

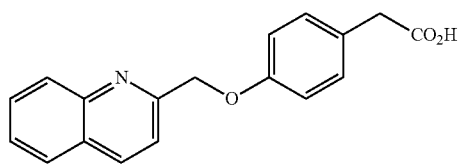 [SMILES: O=C(O)Cc1ccc(OCc2ccc3ccccc3n2)cc1]

To a stirred solution of ethyl 2-(4-(quinolin-2-ylmethoxy)phenyl)acetate (20 g, 0.05 mol) in MeOH (200 mL), a solution of KOH (12.6 g, 0.22 mol) in water (50 mL) was added dropwise and the reaction mixture was stirred for 1 h at RT. The methanol was then removed and the reaction mixture was washed with EtOAc (2×100 mL) and acidified to pH~3 with 1 N HCl at 0° C. The precipitated solid was then filtered and dried to afford 2-(4-(quinolin-2-ylmethoxy)phenyl)acetic acid (15 g, 92%) as a white solid.

2-Oxo-2-(pyridin-3-yl)ethyl 2-(4-(quinolin-2-ylmethoxy)phenyl)acetate

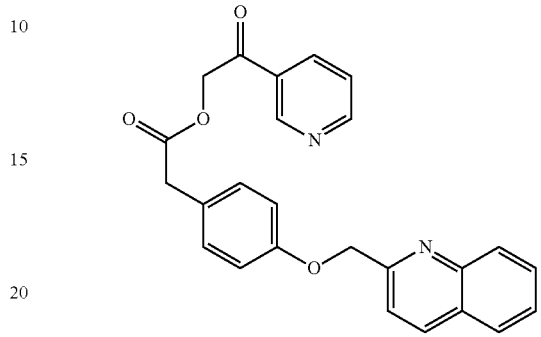

To a solution of 2-(4-(quinolin-2-ylmethoxy)phenyl)acetic acid (2.0 g, 0.006 mol) in acetonitrile (200 mL) were added TEA (1.74 mL, 0.01 mol), and 2-bromo-1-(pyridin-3-yl)ethanone (3.42 g, 0.017 mol) under an inert atmosphere. The reaction mixture was then stirred at RT for 16 h, concentrated in vacuo and the residue was extracted with EtOAc (2×100 mL). The combined organic layers were washed with water, dried over Na$_2$SO$_4$, filtered, and concentrated in vacuo to obtain the crude product. The crude material was purified via silica gel column chromatography to afford 2-oxo-2-(pyridin-3-yl)ethyl 2-(4-(quinolin-2-ylmethoxy)phenyl)acetate (1.5 g, 54%) as a solid.

4-(Pyridin-3-yl)-3-(4-(quinolin-2-ylmethoxy)phenyl) furan-2(5H)-one (Example 1098)

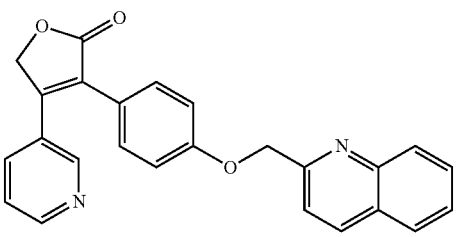 [SMILES: O=C1OCC(c2cccnc2)=C1c1ccc(OCc2ccc3ccccc3n2)cc1]

To a 0° C. solution of 2-oxo-2-(pyridin-3-yl)ethyl 2-(4-(quinolin-2-ylmethoxy)phenyl)acetate (200 mg, 0.48 mmol) in DMF (5 mL) was added NaH (58 mg, 1.21 mmol). The reaction mixture was then stirred at RT for 1 h, quenched with ice, and extracted with EtOAc (2×30 mL). The combined organic layers were washed with water, dried over Na$_2$SO$_4$, filtered, and concentrated in vacuo to obtain the crude product. The crude material was purified via silica gel column chromatography to afford 4-(pyridin-3-yl)-3-(4-(quinolin-2-ylmethoxy)phenyl)furan-2(5H)-one (10 mg, 5%) as a solid.

$^1$H NMR (500 MHz, d$_6$-DMSO): δ 8.41 (d, J=7.2 Hz, 1H), 8.04-7.96 (m, 2H), 7.82-7.76 (m, 2H), 7.70-7.58 (m, 3H), 7.20-7.12 (m, 3H), 7.02-6.96 (m, 3H), 5.35 (s, 2H), 3.52 (s, 2H). MS: M+H: m/z=395.2 and HPLC: 89%, (Condition-C).

Synthesis of 4-(Pyridin-4-yl)-3-(4-(quinolin-2-yl-methoxy)phenyl)furan-2(5H)-one (Example 37), Route A

2-(4-(Benzyloxy)phenyl)acetic Acid

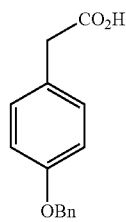

To a stirred solution of ethyl 2-(4-(benzyloxy)phenyl)acetate (20 g, 0.07 mol) in EtOH (300 mL) was added a solution of KOH (20.7 g, 0.37 mol) in water (100 mL) at RT. The reaction mixture was then stirred for additional 1 h at RT and then concentrated in vacuo. The residue was acidified to pH~2 using 2 N HCl and extracted with EtOAc (3×200 mL). The combined organic layers were washed with water, dried over $Na_2SO_4$, filtered, and concentrated in vacuo to afford 2-(4-(benzyloxy)phenyl)acetic acid (19 g, 98%) as a solid.

2-Bromo-1-(pyridin-4-yl)ethanone Hydrobromide

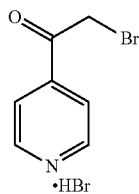

To a stirred solution of 1-(pyridin-4-yl)ethanone (10 g, 0.08 mol) in $CCl_4$ (150 mL), $Br_2$ (3.99 mL, 0.02 mol) was added dropwise at 0° C. The reaction mixture was then refluxed for 1 h, filtered, and dried in vacuo to afford 2-bromo-1-(pyridin-4-yl)ethanone hydro bromide (22 g, 94%) as a solid.

2-Oxo-2-(pyridin-4-yl)ethyl 2-(4-(benzyloxy)phenyl) acetate

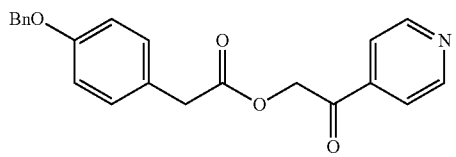 [SMILES: O=C(Cc1ccc(OCc2ccccc2)cc1)OCC(=O)c1ccncc1]

To a 10° C. stirred solution of 2-(4-(benzyloxy)phenyl) acetic acid (5.0 g, 0.02 mol) in MeOH (50 mL) was added a solution of potassium tert-butoxide (2.43 g, 0.02 mol) in MeOH (50 mL) under an inert atmosphere. The reaction mixture was stirred for 1 h, concentrated in vacuo and the residue was dissolved in DMF (30 mL). Potassium tert-butoxide (3.6 g, 0.03 mmol) was then added followed by 2-bromo-1-(pyridin-4-yl)ethanone hydrobromide (10.3 g, 0.05 mol), and the reaction mixture at RT. The reaction mixture was then stirred for an additional 16 h at RT, quenched with water, stirred for an additional 10 min and the precipitated solid was filtered. The crude solid was dissolved in EtOAc (200 mL) and washed with water, dried over $Na_2SO_4$, filtered and concentrated in vacuo to afford 2-oxo-2-(pyridin-4-yl)ethyl 2-(4-(benzyloxy)phenyl)acetate (3.6 g, 48%) as a solid.

3-(4-(Benzyloxy)phenyl)-4-(pyridin-4-yl)furan-2 (5H)-one

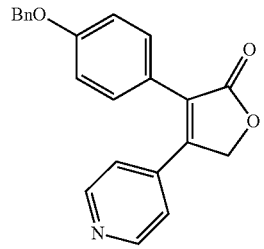 [SMILES: O=C1OCC(c2ccncc2)=C1c1ccc(OCc2ccccc2)cc1]

To a stirred solution of 2-oxo-2-(pyridin-4-yl)ethyl 2-(4-(benzyloxy)phenyl)acetate (1.8 g, 0.004 mol) in acetonitrile (50 mL) was added triethylamine (10 mL, 0.07 mol) under an inert atmosphere. The reaction mixture was then refluxed for 2 h, concentrated in vacuo, and the residue was dissolved in EtOAc (100 mL). The organic layer was washed with brine, dried over $Na_2SO_4$, filtered and concentrated in vacuo to yield the crude product. The crude material was purified via silica gel column chromatography to afford 3-(4-(benzyloxy)phenyl)-4-(pyridin-4-yl)furan-2(5H)-one (140 mg, 8%).

3-(4-hydroxyphenyl)-4-(pyridin-4-yl)furan-2(5H)-one

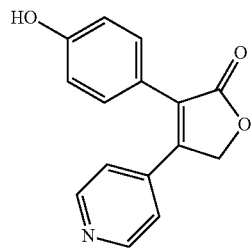 [SMILES: O=C1OCC(c2ccncc2)=C1c1ccc(O)cc1]

A mixture of 3-(4-(benzyloxy)phenyl)-4-(pyridin-4-yl)furan-2(5H)-one (1.0 g, 0.002 mol) in 33% HBr/AcOH (50 mL) was refluxed for 3 h. The reaction mixture was quenched with a saturated $NaHCO_3$ solution and extracted with EtOAc (2×50 mL). The combined organic layers were washed with water, dried over $Na_2SO_4$, filtered, and concentrated in vacuo to afford 3-(4-hydroxyphenyl)-4-(pyridin-4-yl)furan-2(5H)-one (0.7 g, 95%).

4-(Pyridin-4-yl)-3-(4-(quinolin-2-ylmethoxy)phenyl) furan-2(5H)-one (Example 37)

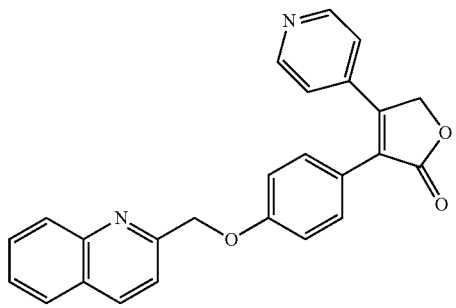 [SMILES: O=C1OCC(c2ccncc2)=C1c1ccc(OCc2ccc3ccccc3n2)cc1]

To a stirred solution of 3-(4-hydroxyphenyl)-4-(pyridin-4-yl)furan-2(5H)-one (700 mg, 2.76 mmol) in DMF (10 mL) was added K$_2$CO$_3$ (763.6 mg, 5.5 mmol) followed by 2-(chloromethyl)quinoline (711 mg, 3.32 mmol). The reaction mixture was then heated at 80° C. for 2 h, quenched with cold water, and extracted with EtOAc (2×25 mL). The combined organic layers were washed with brine, dried over Na$_2$SO$_4$, filtered, and concentrated in vacuo to obtain the crude product. The crude material was purified via silica gel column chromatography to afford 4-(pyridin-4-yl)-3-(4-(quinolin-2-ylmethoxy)phenyl) furan-2(5H)-one (190 mg, 19%) as a solid. $^1$H NMR (500 MHz, d$_6$-DMSO): δ 8.61 (d, J=7.7 Hz, 2H), 8.42 (d, J=7.1 Hz, 1H), 8.04-7.96 (m, 2H), 7.81-7.76 (m, 1H), 7.65 (d, J=7.4 Hz, 1H), 7.60-7.54 (m, 1H), 7.44-7.36 (m, 4H), 7.11 (d, J=7.2 Hz, 2H), 5.40 (s, 2H), 5.34 (s, 2H). MS: M$^+$H: m/z=395.1 and HPLC: 95%, (Condition-H).

Synthesis of 4-(Pyridin-4-yl)-3-(4-(quinolin-2-ylmethoxy)phenyl)furan-2(5H)-one (Example 37), Route B

Ethyl 2-(4-(quinolin-2-ylmethoxy)phenyl)acetate

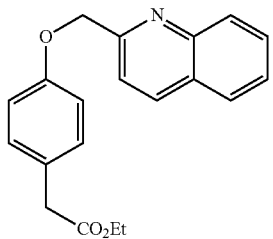

To a stirred solution of compound ethyl 2-(4-hydroxyphenyl)acetate (30 g, 0.16 mol) in acetonitrile (300 mL) was added K$_2$CO$_3$ (114.9 g, 0.83 mol) and 2-(chloromethyl) quinoline (42.7 g, 0.19 mol) at RT. The reaction mixture was refluxed for 16 h, filtered and the resulting solid residue was extracted with EtOAc (2×100 mL). The combined organic layers were washed with water, dried over Na$_2$SO$_4$ and concentrated in vacuo to afford ethyl 2-(4-(quinolin-2-ylmethoxy)phenyl)acetate (50 g, 93%) as a solid.

2-(4-(Quinolin-2-ylmethoxy)phenyl)acetic Acid

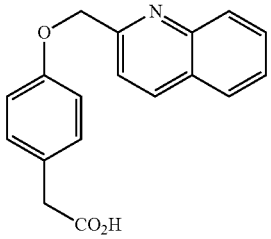 [SMILES: O=C(O)Cc1ccc(OCc2ccc3ccccc3n2)cc1]

To a solution of ethyl 2-(4-(quinolin-2-ylmethoxy)phenyl) acetate (8 g, 0.02 mol) in MeOH:THF (300 mL; 1:1) was added LiOH.H$_2$O (5.21 g, 0.124 mol). The reaction mixture was stirred at RT for 1 h and then concentrated in vacuo to obtain the crude compound. The crude material was acidified with HCl (1N), filtered and dried in vacuo to afford 2-(4-(quinolin-2-ylmethoxy)phenyl)acetic acid (7.0 g, 95%) as a solid.

4-(Pyridin-4-yl)-3-(4-(quinolin-2-ylmethoxy)phenyl) furan-2(5H)-one (Example 37)

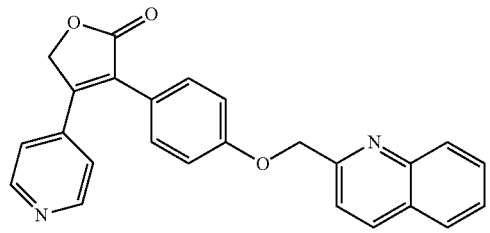 [SMILES: O=C1OCC(c2ccncc2)=C1c1ccc(OCc2ccc3ccccc3n2)cc1]

To a solution of 2-(4-(quinolin-2-ylmethoxy)phenyl)acetic acid (3.0 g, 0.01 mol) in acetonitrile (40 mL) were added TEA (1.3 mL, 0.01 mol) and 2-bromo-1-(pyridin-4-yl)ethanone hydrobromide (2.86 g, 0.01 mol) at RT under an inert atmosphere. The reaction mixture was stirred for 1 h and then cooled to 0° C. DBU (46.6 g, 0.03 mol) was then added and the reaction mixture was stirred for 2 h at 0° C. and quenched with HCl (1 N). The aqueous layer was basified with a NaHCO$_3$ solution and extracted with DCM (2×50 mL). The combined organic layers were washed with water, dried over Na$_2$SO$_4$ and concentrated in vacuo to obtain the crude product. The crude material was purified via silica gel column chromatography eluting with 25% EtOAc in hexanes to afford 4-(pyridin-4-yl)-3-(4-(quinolin-2-ylmethoxy)phenyl) furan-2(5H)-one (600 mg, 15%) as a solid.

Synthesis of 1-methyl-4-(pyridin-4-yl)-3-(4-(quinolin-2-ylmethoxy)phenyl)-1H-pyrrol-2(5H)-one (Example 94)

(Z)-4-Hydroxy-N-methyl-3-(pyridin-4-yl)-2-(4-(quinolin-2-ylmethoxy)phenyl)but-2-enamide

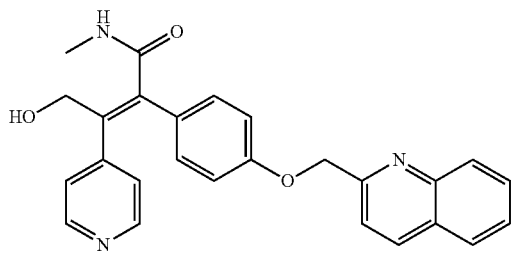 [SMILES: CNC(=O)/C(=C(\CO)c1ccncc1)c1ccc(OCc2ccc3ccccc3n2)cc1]

A solution of 4-(pyridin-4-yl)-3-(4-(quinolin-2-yl-methoxy)phenyl)furan-2(5H)-one (1.0 g, 0.002 mol) and MeNH$_2$ in MeOH (25 mL) was refluxed for 1 h. The reaction mixture was concentrated in vacuo to afford (Z)-4-hydroxy-N-methyl-3-(pyridin-4-yl)-2-(4-(quinolin-2-ylmethoxy) phenyl)but-2-enamide (920 mg, 86%) as a solid.

1-Methyl-4-(pyridin-4-yl)-3-(4-(quinolin-2-yl-methoxy)phenyl)-1H-pyrrol-2(5H)-one (Example 94)

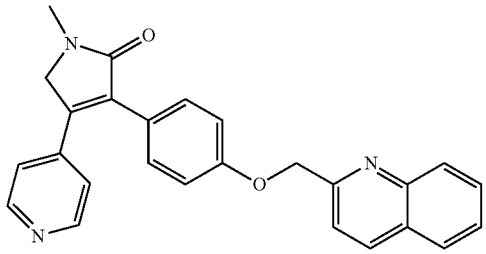 [SMILES: CN1CC(c2ccncc2)=C(c2ccc(OCc3ccc4ccccc4n3)cc2)C1=O]

To a 0° C. solution of (Z)-4-hydroxy-N-methyl-3-(pyridin-4-yl)-2-(4-(quinolin-2-ylmethoxy)phenyl)but-2-enamide (430 mg, 1.01 mmol) in 1:1 ether:DCM (20 mL), PBr$_3$ (0.114 mL, 1.21 mol) was added. The reaction mixture was stirred at RT for 2 h, diluted with DCM and basified with a NaHCO$_3$ solution. The organic layer was separated, washed with water, dried over Na$_2$SO$_4$ and concentrated in vacuo to obtain the crude product. The crude material was purified via silica gel column chromatography to afford 1-methyl-4-(pyridin-4-yl)-3-(4-(quinolin-2-ylmethoxy)phenyl)-1H-pyrrol-2(5H)-one (350 mg, 85%) as a solid. $^1$H NMR (500 MHz, CD$_3$OD): δ 8.81 (d, J=7.8 Hz, 2H), 8.24-8.19 (m, 2H), 8.11-7.94 (m, 3H), 7.85-7.80 (m, 1H), 7.59 (d, J=7.2 Hz, 2H), 7.44 (s, 2H), 7.21 (d, J=7.2 Hz, 2H), 5.61 (s, 2H), 3.38 (s, 2H), 3.09 (s, 3H). MS: M$^+$H: m/z=408.2. HPLC: 89%, (Condition-B).

Synthesis of 4-morpholino-3-(4-(quinolin-2-yl-methoxy)phenyl)furan-2(5H)-one (Example 1085)

2-((4-Bromophenoxy)methyl)quinoline

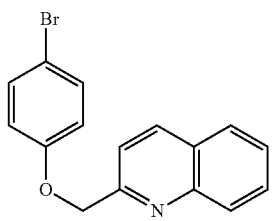 [SMILES: Brc1ccc(OCc2ccc3ccccc3n2)cc1]

To a stirred solution of 4-bromophenol (10 g, 0.057 mol) and 2-(chloro methyl)quinoline (15.4 g, 0.063 mol) in AcN (25 mL) was added K$_2$CO$_3$ (24 g, 0.17 mol). The reaction mixture was refluxed for 3 h, filtered and the filtrate was concentrated in vacuo. The residue was diluted with water and extracted with EtOAc (2×200 mL). The combined organic layers were dried over anhydrous Na$_2$SO$_4$, filtered, and concentrated in vacuo to obtain 2-((4-bromophenoxy) methyl)quinoline (9 g, 50%) as a solid.

2-((4-(4,4,5,5-Tetramethyl-1,3,2-dioxaborolan-2-yl) phenoxy)methyl)quinoline

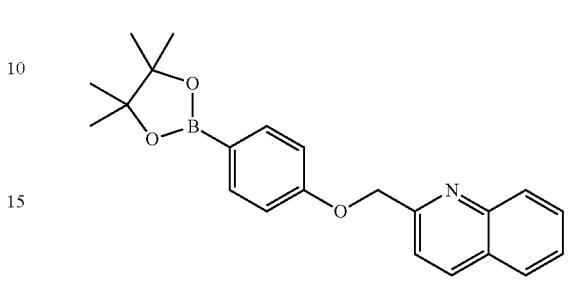

To a stirred solution of 2-((4-bromophenoxy)methyl) quinoline (3 g, 0.008 mol) in dioxane (20 mL) was added bispinacolato diborane (2.7 g, 0.010 mol) followed by potassium acetate (2.59 g, 0.026 mol) at room temperature under a N$_2$ atmosphere. The reaction mixture was stirred for 10 minutes and then P(Cy)$_3$ (0.18 g, 0.65 mmol) followed by Pd(dba)$_2$ (0.32 g, 0.35 mmol) were added to reaction mixture. The reaction mixture was then refluxed for 1 h, diluted with water and extracted with EtOAc (2×100 mL). The combined organic layers were dried over anhydrous Na$_2$SO$_4$, filtered, and concentrated in vacuo to afford 2-((4-(4,4,5,5-tetramethyl-1,3,2-dioxaborolan-2-yl)phenoxy)methyl)quinoline (2.5 g, 74%) as a solid.

3,4-Dibromofuran-2(5H)-one

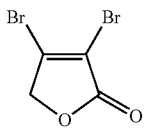

To a stirred solution of 3,4-dibromo-5-hydroxyfuran-2 (5H)-one (3.0 g, 0.011 mol) in MeOH (27 mL) was added NaBH$_4$ (660 mg, 0.017 mol) at 0° C. under a N$_2$ atmosphere. The reaction mixture was stirred for 30 minutes and then a solution of H$_2$SO$_4$ (1.8 g) in MeOH (9 mL) was added. The reaction mixture was stirred for an additional 1 h, concentrated in vacuo and the residue was dissolved in DCM (100 mL). The organic layer was then washed with water, dried over anhydrous Na$_2$SO$_4$, filtered, and concentrated in vacuo to afford 3,4-dibromofuran-2(5H)-one (2.6 g, 93%) as a solid.

3-Bromo-4-morpholinofuran-2(5H)-one

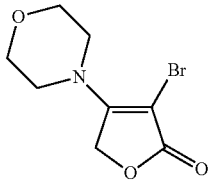 [SMILES: O=C1OCC(N2CCOCC2)=C1Br]

To a stirred solution of 3,4-dibromofuran-2(5H)-one (1 g, 0.004 mol) in DMF (10 mL) was added Cs₂CO₃ (1.34 g, 0.004 mol) followed by morpholine (360 mg, 0.004 mol) at room temperature under a N₂ atmosphere. The reaction mixture was then stirred for 30 minutes, quenched with ice water and extracted with EtOAc (2×50 mL). The combined organic layers were washed with water, dried over anhydrous Na₂SO₄, filtered, and concentrated in vacuo to afford 3-bromo-4-morpholinofuran-2(5H)-one (0.87 g, 85%) as a solid.

4-Morpholino-3-(4-(quinolin-2-ylmethoxy)phenyl)furan-2(5H)-one (Example 1085)

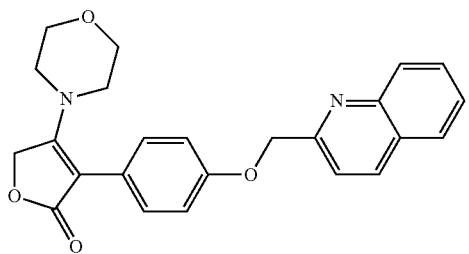 [SMILES: O=C1OCC(N2CCOCC2)=C1c1ccc(OCc2ccc3ccccc3n2)cc1]

To a stirred solution of 3-bromo-4-morpholinofuran-2(5H)-one (300 mg, 1.20 mmol) in 2:1 toluene/H₂O (8 mL) were added 2-((4-(4,4,5,5-tetramethyl-1,3,2-dioxaborolan-2-yl)phenoxy)methyl)quinoline (480 mg, 1.33 mmol), Cs₂CO₃ (1.54 g, 4.23 mmol) and Pd(dppf)Cl₂ (197.5 mg, 0.24 mmol). The reaction mixture was then refluxed for 4 h, filtered and the filtrate was partitioned between water and EtOAc. The organic layer was separated, washed with water, dried over anhydrous Na₂SO₄, filtered, and concentrated in vacuo. The crude material was purified via silica gel column chromatography eluting with 40% EtOAc in hexanes to afford 4-morpholino-3-(4-(quinolin-2-ylmethoxy)phenyl)furan-2(5H)-one (50 mg, 10%) as a solid. ¹H NMR (500 MHz, d₆-DMSO): δ 8.42 (d, J=7.6 Hz, 1H), 8.04-7.96 (m, 2H), 7.82-7.76 (m, 1H), 7.70-7.67 (m, 1H), 7.65-7.59 (m, 1H), 7.17 (d, J=7.2 Hz, 2H), 7.05 (d, J=7.2 Hz, 2H), 5.38 (s, 2H), 4.91 (s, 2H), 3.60 (bs, 4H), 3.19 (bs, 4H). MS: M⁺H: m/z=403.1; M⁺Na: m/z=425.2 HPLC: 90%, (Condition-J).

Synthesis of 3-(4-methoxyphenyl)-4-(4-(2-(quinolin-2-yl)ethyl)phenyl)furan-2(5H)-one (Example 14)

Ethyl 2-(4-methoxyphenyl)acetate

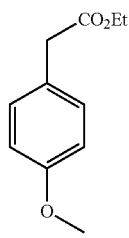

To a solution of ethyl 2-(4-hydroxyphenyl)acetate (15 g, 0.09 mmol) in acetonitrile (100 mL) were added anhydrous K₂CO₃ (27.23 g, 0.19 mol) followed by Me₂SO₄ (14.94 g, 0.11 mol) at RT. The reaction mixture was then refluxed for 5 h, filtered through a pad of Celite® and the filtrate was concentrated in vacuo. The residue was dissolved in EtOAc (300 mL). The organic layer was then washed with water, dried over Na₂SO₄ and concentrated in vacuo to afford ethyl 2-(4-methoxyphenyl)acetate (16 g, 84%) as a solid.

2-(4-Methoxyphenyl)acetic Acid

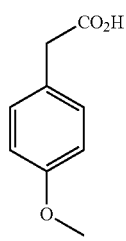

To a solution of ethyl 2-(4-methoxyphenyl)acetate (5.0 g, 0.025 mol) in 2:2:1 MeOH:THF:H₂O (50 mL) was added LiOH.H₂O (5.14 g, 0.128 mol). The reaction mixture was stirred at RT for 16 h and concentrated in vacuo to obtain the crude product. The crude material was acidified with HCl (1N) to pH 2 and then the product was extracted with EtOAc (2×100 mL). The combined organic layers were washed with water, dried over Na₂SO₄, and concentrated in vacuo to afford 2-(4-methoxyphenyl)acetic acid (4.05 g, 94%) as a solid.

1-(4-(Benzyloxy)phenyl)ethanone

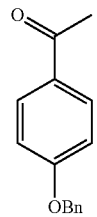

To a solution of 1-(4-hydroxyphenyl)ethanone (10 g, 0.07 mol) in DMF (15 mL), were added anhydrous K₂CO₃ (20.3 g, 0.14 mol) and benzyl chloride (11.16 g, 0.08 mmol). The reaction mixture was then stirred at RT for 16 h, quenched with ice, and a solid was precipitated. The obtained solid residue was filtered and dried in vacuo to afford 1-(4-(benzyloxy)phenyl)ethanone (14.7 g, 89%) as a solid.

1-(4-(Benzyloxy)phenyl)-3-phenylpropan-1-one

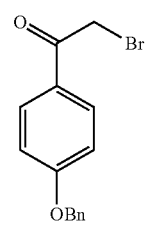

To a solution of 1-(4-(benzyloxy)phenyl)ethanone (5.0 g, 0.02 mol) in MeOH (120 mL) was added a solution of Br₂ (4.22 g, 0.026 mol) in MeOH (13 mL). The reaction mixture was stirred at RT for 3 h and then concentrated in vacuo. The residue was then treated with HCl (1N, 20 mL), quenched with ice, and the resulting solid precipitate was filtered and dried in vacuo to afford 1-(4-(benzyloxy)phenyl)-3-phenylpropan-1-one (6 g, 89%) as a white solid.

2-(4-(Benzyloxy)phenyl)-2-oxoethyl 2-(4-methoxyphenyl)acetate

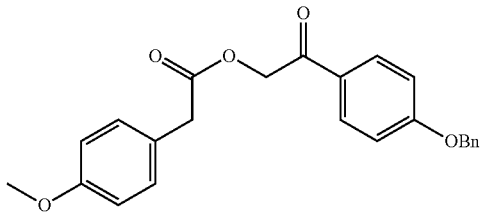 [SMILES: COc1ccc(CC(=O)OCC(=O)c2ccc(OCc3ccccc3)cc2)cc1]

To a stirred solution of 2-(4-methoxyphenyl)acetic acid (3 g, 0.01 mol) in acetonitrile (60 mL) were added TEA (16.5 mL, 0.129 mol) and 1-(4-(benzyloxy)phenyl)-3-phenylpropan-1-one (6.6 g, 0.02 mol). The reaction mixture was stirred at RT for 16 h, concentrated in vacuo and the resulting residue was extracted with EtOAc (2×100 mL). The combined organic layers were washed with water, dried over $Na_2SO_4$ and concentrated in vacuo to afford 2-(4-(benzyloxy)phenyl)-2-oxoethyl 2-(4-methoxyphenyl)acetate (5 g, 71%) as a brown solid.

4-(4-(Benzyloxy)phenyl)-3-(4-methoxyphenyl)furan-2(5H)-one

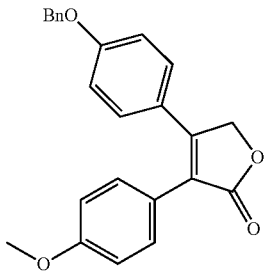 [SMILES: COc1ccc(C2=C(c3ccc(OCc4ccccc4)cc3)COC2=O)cc1]

To a 0° C. solution of 2-(4-(benzyloxy)phenyl)-2-oxoethyl 2-(4-methoxyphenyl)acetate (3.0 g, 0.007 mol) in DMF (20 mL) was added NaH (0.96 g, 0.01 mol). The reaction mixture was stirred at RT for 30 minutes and quenched with ice to obtain a solid precipitate. The solid precipitate was filtered and dried in vacuo to afford 4-(4-(benzyloxy)phenyl)-3-(4-methoxyphenyl)furan-2(5H)-one (2.4 g, 84%) as a solid.

4-(4-Hydroxyphenyl)-3-(4-methoxyphenyl)furan-2(5H)-one

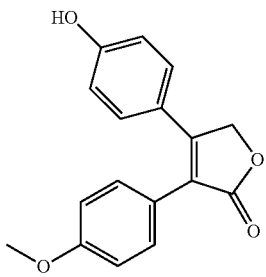 [SMILES: COc1ccc(C2=C(c3ccc(O)cc3)COC2=O)cc1]

To a 0° C. solution of 4-(4-(benzyloxy)phenyl)-3-(4-methoxyphenyl)furan-2(5H)-one (1.5 g, 0.004 mol) in MeOH (50 mL) was added $Pd(OH)_2$ (150 mg, 1.068 mol) under an inert atmosphere. The reaction mixture was then stirred under a hydrogen atmosphere for 2 h at RT, filtered through a pad of Celite® and the filtrate was concentrated in vacuo to afford 4-(4-hydroxyphenyl)-3-(4-methoxyphenyl)furan-2(5H)-one (900 mg, 81%) as a solid.

3-(4-Methoxyphenyl)-4-(4-(2-(quinolin-2-yl)ethyl)phenyl)furan-2(5H)-one (Example 14)

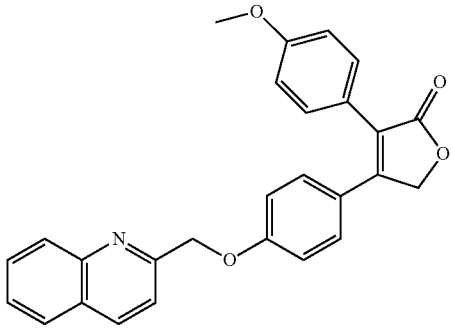 [SMILES: COc1ccc(C2=C(c3ccc(OCc4ccc5ccccc5n4)cc3)COC2=O)cc1]

To a stirred solution of 4-(4-hydroxyphenyl)-3-(4-methoxyphenyl)furan-2(5H)-one (280 mg, 0.99 mol) in DMF (5 mL) were added $K_2CO_3$ (274 mg, 1.98 mol) and 2-(chloromethyl)quinoline (255 mg, 1.19 mol) at RT. The reaction mixture was then heated at 80° C. for 3 h, quenched with ice and then extracted with EtOAc (2×20 mL). The combined organic layers were washed with water, dried over $Na_2SO_4$, and concentrated in vacuo to obtain the crude product. The crude material was purified via silica gel column chromatography using 20% ethyl acetate in hexanes to afford 3-(4-methoxyphenyl)-4-(4-(2-(quinolin-2-yl)ethyl)phenyl)furan-2(5H)-one (50 mg, 12%) as a yellow solid.

$^1$H NMR (500 MHz, $d_6$-DMSO): δ 8.41 (d, J=7.8 Hz, 1H), 8.02-7.98 (m, 2H), 7.78 (t, J=7.6 Hz, 1H), 7.68-7.52 (m, 1H), 7.23 (d, J=7.2 Hz, 2H), 7.25 (d, J=7.6 Hz, 2H), 7.10 (d, J=7.6 Hz, 2H), 6.98 (d, J=7.2 Hz, 2H), 5.40 (s, 2H), 5.25 (s, 2H), 3.79 (s, 3H). MS: M+H: m/z=424.2. HPLC: 97%, (Condition-H).

Synthesis of 3-(4-methoxyphenyl)-4-(4-((6-methylpyridin-2-yl)methoxy)phenyl)furan-2(5H)-one (Example 1095)

2,6-Dimethylpyridine 1-oxide

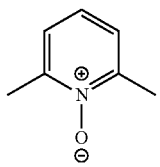

To a 0° C. solution of 2,6-dimethylpyridine (1.0 g, 0.009 mol) in $CHCl_3$ (25 mL) was added mCPBA (3.17 g, 0.01 mol). The reaction mixture was then stirred for 12 h at RT, quenched with a saturated $Na_2CO_3$ solution. The organic layer was separated, dried over $Na_2SO_4$ and concentrated in vacuo to afford 2,6-dimethylpyridine 1-oxide (980 mg, 85%) as a solid.

(6-Methylpyridin-2-yl)methyl Acetate

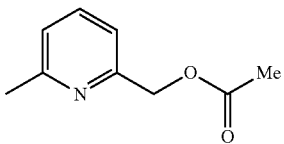

A solution of 2,6-dimethylpyridine 1-oxide (980 mg, 0.79 mmol) in acetic anhydride (5 mL) was refluxed for 1 h. The reaction mixture was then concentrated in vacuo to obtain the crude product. The crude material was purified via silica gel column chromatography using 20% ethyl acetate in hexanes to afford (6-methylpyridin-2-yl)methyl acetate (1.0 g) as a solid.

(6-Methylpyridin-2-yl)methanol Hydrochloride

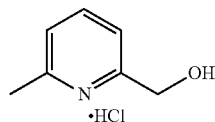

A solution of (6-methylpyridin-2-yl)methyl acetate (1.0 g) in concentrated HCl (3 mL) was refluxed for 1 h. The reaction mixture was then concentrated in vacuo to obtain the crude product. The crude material was azeotroped with toluene, and the residue obtained was filtered and dried in vacuo to afford (6-methylpyridin-2-yl)methanol hydrochloride (811 mg) as a solid.

2-(Chloromethyl)-6-methylpyridine

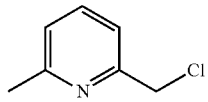

A solution of (6-methylpyridin-2-yl)methanol hydrochloride (1.0 g, 0.008 mol) in SOCl$_2$ (3 mL) was stirred at RT for 1 h. The reaction mixture was then concentrated in vacuo to obtain the crude product. The crude material was azeotroped with toluene and the resulting residue was filtered and dried in vacuo to afford 2-(chloromethyl)-6-methylpyridine (800 mg, 63%) as a light brown solid.

3-(4-methoxyphenyl)-4-(4-((6-methylpyridin-2-yl)methoxy)phenyl)furan-2(5H)-one (Example 1095)

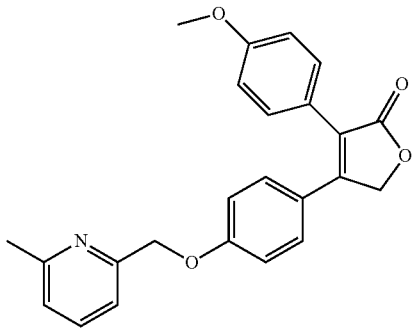 [SMILES: COc1ccc(C2=C(c3ccc(OCc4cccc(C)n4)cc3)COC2=O)cc1]

To a solution of 4-(4-hydroxyphenyl)-3-(4-methoxyphenyl)furan-2(5H)-one (300 mg, 1.06 mmol) in DMF (10 mL) were added K$_2$CO$_3$ (294 mg, 2.12 mmol), 2-(chloromethyl)-6-methylpyridine (225 mg, 1.59 mol) at RT. The reaction mixture was then heated at 80° C. for 16 h, quenched with ice and then extracted with EtOAc (2×100 mL). The combined organic layers were washed with water, dried over Na$_2$SO$_4$, and concentrated in vacuo to obtain the crude product. The crude material was purified via silica gel column chromatography to afford 3-(4-methoxyphenyl)-4-(4-((6-methylpyridin-2-yl)methoxy)phenyl)furan-2(5H)-one (10 mg) as a solid. $^1$H NMR (500 MHz, d$_6$-DMSO): δ 8.44 (d, J=7.2 Hz, 1H), 7.79 (m, 1H), 7.71 (d, J=7.6 Hz, 1H), 7.63 (t, J=7.6 Hz, 1H), 7.38-7.27 (m, 3H), 7.16 (d, J=7.2 Hz, 2H), 6.99-6.92 (m, 2H), 5.41 (s, 2H), 5.33 (s, 2H), 2.79 (s, 3H). MS: M$^+$H: m/z=388.2.

Synthesis of 4-(3-chloro-4-methoxyphenyl)-3-(4-(quinolin-2-ylmethoxy)phenyl)furan-2(5H)-one (Example 54)

2-Bromo-1-(3-chloro-4-methoxyphenyl)ethanone

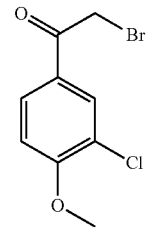

To a solution of 1-(3-chloro-4-methoxyphenyl)ethanone (1.0 g, 5.42 mmol) in MeOH (29.5 mL) was added a solution of bromine (0.33 mL, 6.50 mmol) in MeOH (10 mL) at RT. The reaction mixture was then stirred for 2 h, quenched with ice and extracted with DCM (2×20 mL). The combined organic layers were washed with water, dried over Na$_2$SO$_4$, and concentrated in vacuo to afford 2-bromo-1-(3-chloro-4-methoxyphenyl)ethanone (1.0 g, 70%) as solid.

2-(3-chloro-4-methoxyphenyl)-2-oxoethyl 2-(4-(quinolin-2-ylmethoxy)phenyl)acetate

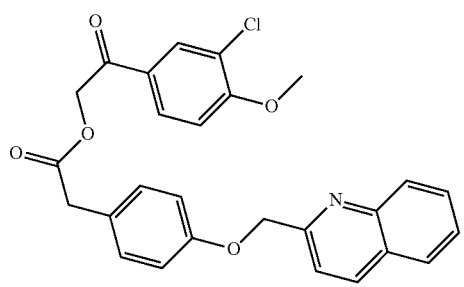 [SMILES: COc1ccc(C(=O)COC(=O)Cc2ccc(OCc3ccc4ccccc4n3)cc2)cc1Cl]

To a solution of 2-(4-(quinolin-2-ylmethoxy)phenyl)acetic acid (1.0 g, 5.42 mmol) in acetonitrile (20 mL) were added Et$_3$N (5.54 mL, 43.4 mmol) and 2-bromo-1-(3-chloro-4-methoxyphenyl)ethanone (1.07 g, 3.65 mmol) under an inert atmosphere. The reaction mixture was then stirred at RT for 1 h and concentrated in vacuo to obtain the crude product. The crude material was extracted with EtOAc (2×50 mL). The combined organic layers were washed with water, dried over Na$_2$SO$_4$, and concentrated in vacuo to afford 2-(3-chloro-4-methoxyphenyl)-2-oxoethyl 2-(4-(quinolin-2-ylmethoxy)phenyl)acetate (750 mg, 29%) as a solid.

4-(3-Chloro-4-methoxyphenyl)-3-(4-(quinolin-2-ylmethoxy)phenyl)furan-2(5H)-one (Example 54)

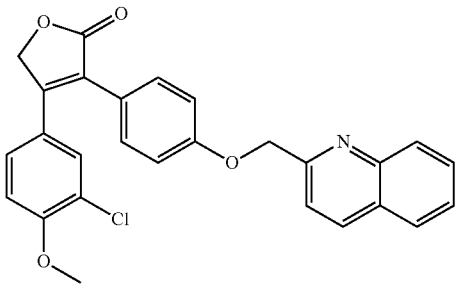 [SMILES: COc1ccc(C2=C(c3ccc(OCc4ccc5ccccc5n4)cc3)C(=O)OC2)cc1Cl]

To a 0° C. solution of 2-(3-chloro-4-methoxyphenyl)-2-oxo-ethyl 2-(4-(quinolin-2-ylmethoxy)phenyl)acetate (750 mg, 1.58 mmol) in DMF (10 mL) was added NaH (190 mg, 3.95 mmol). The reaction mixture was then stirred at RT for 1 h, quenched with ice and extracted with EtOAc (2×50 mL). The combined organic layers were washed with water, dried over $Na_2SO_4$, and concentrated in vacuo to obtain the crude product. The crude material was purified via silica gel column chromatography to afford 4-(3-chloro-4-methoxyphenyl)-3-(4-(quinolin-2-ylmethoxy)phenyl)furan-2(5H)-one (40 mg, 6%) as a solid. $^1$H NMR (500 MHz, $d_6$-DMSO): δ 8.42-8.38 (m, 1H), 8.16-8.05 (m, 2H), 7.72 (t, J=7.6 Hz, 1H), 7.49-7.39 (m, 2H), 7.66 (d, J=8.2 Hz, 1H), 7.58 (t, J=7.2 Hz, 1H), 7.42-7.36 (m, 1H), 7.29-7.20 (m, 2H), 7.17-7.10 (m, 2H), 5.45 (s, 2H), 5.23 (s, 2H), 3.85 (s, 3H). MS: M$^+$H: m/z=458.1. HPLC: 93%, (Condition-H).

Synthesis of 4-(3-fluoro-4-methoxyphenyl)-3-(4-(quinolin-2-ylmethoxy)phenyl)furan-2(5H)-one (Example 53)

4-(3-fluoro-4-methoxyphenyl)-3-(4-(quinolin-2-ylmethoxy)phenyl)furan-2(5H)-one (Example 53)

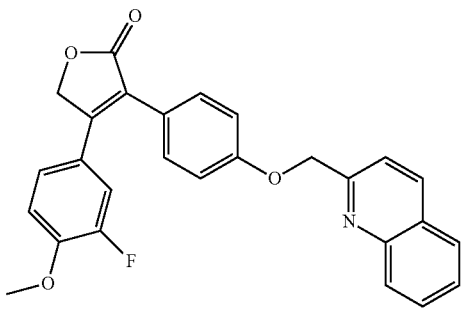 [SMILES: COc1ccc(C2=C(c3ccc(OCc4ccc5ccccc5n4)cc3)C(=O)OC2)cc1F]

Following the procedures for the preparation of 4-(3-chloro-4-methoxyphenyl)-3-(4-(quinolin-2-ylmethoxy)phenyl)furan-2(5H)-one using 2-bromo-1-(3-fluoro-4-methoxyphenyl)ethanone provided the title compound. $^1$H NMR (500 MHz, $d_6$-DMSO): δ 8.42-8.38 (m, 1H), 8.16-8.05 (m, 2H), 7.72 (t, J=7.6 Hz, 1H), 7.49-7.39 (m, 2H), 7.66 (d, J=8.2 Hz, 1H); 7.58 (t, J=7.2 Hz, 1H), 7.42-7.36 (m, 1H), 7.29-7.20 (m, 2H), 7.17-7.10 (m, 2H), 5.45 (s, 2H), 5.23 (s, 2H), 3.85 (s, 3H). MS: M$^+$H: m/z=442.2 and HPLC: 92%, (Condition-J).

Synthesis of 4-(4-methoxyphenyl)-3-(4-(quinolin-2-ylmethoxy)phenyl)furan-2(5H)-one (Example 59)

4-(4-Methoxyphenyl)-3-(4-(quinolin-2-ylmethoxy)phenyl)furan-2(5H)-one (Example 59)

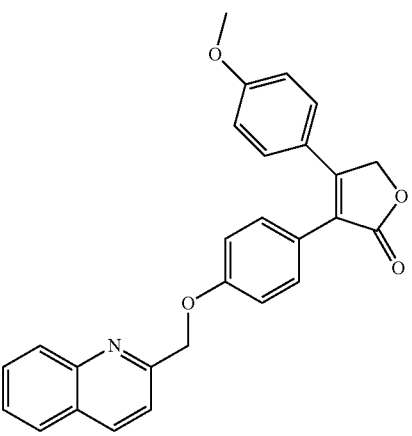 [SMILES: COc1ccc(C2=C(c3ccc(OCc4ccc5ccccc5n4)cc3)C(=O)OC2)cc1]

Following the procedure for the preparation of 4-(3-chloro-4-methoxyphenyl)-3-(4-(quinolin-2-ylmethoxy)phenyl)furan-2(5H)-one using 2-bromo-1-(4-methoxyphenyl)ethanone provided the title compound. $^1$H NMR (500 MHz, CDCl$_3$): δ 8.86-8.78 (m, 2H), 8.21 (d, J=7.8 Hz, 1H), 8.08 (d, J=7.6 Hz, 1H), 7.82 (d, J=7.6 Hz, 1H), 7.68-7.64 (m, 1H), 7.58-7.50 (m, 1H), 7.39 (d, J=7.2 Hz, 2H), 7.29-7.21 (m, 1H), 7.02 (d, J=7.4 Hz, 2H), 6.92 (d, J=7.4 Hz, 2H), 5.41 (s, 2H), 5.05 (s, 2H), 3.92 (s, 3H). MS: M$^+$H: m/z=424.2; M$^+$Na: m/z=446.1. HPLC: 90%, (Condition-C).

Synthesis of 4-(4-methoxyphenyl)-1-methyl-3-(4-(quinolin-2-ylmethoxy)phenyl)-1H-pyrrol-2(5H)-one (Example 125)

4-(4-Methoxyphenyl)-1-methyl-3-(4-(quinolin-2-ylmethoxy)phenyl)-1H-pyrrol-2(5H)-one (Example 125)

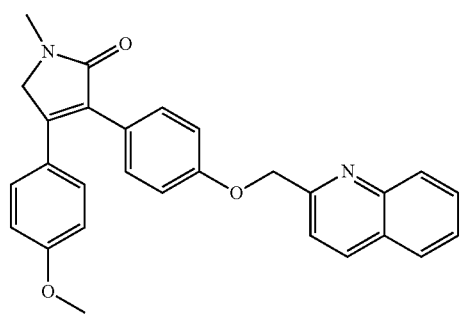 [SMILES: COc1ccc(C2=C(c3ccc(OCc4ccc5ccccc5n4)cc3)C(=O)N(C)C2)cc1]

A stirred solution of 4-(4-methoxyphenyl)-3-(4-(quinolin-2-ylmethoxy)phenyl)furan-2(5H)-one (500 mg, 1.18 mmol) in 2N methanolic MeNH$_2$ (50 mL) was refluxed for 3 h. The reaction mixture was then concentrated in vacuo and the residue was dissolved in 4N HCl in dioxane The reaction mixture was refluxed for 16 h, then basified with aqueous NaHCO$_3$ solution and extracted with EtOAc (2×30 mL). The combined organic layers were washed with water, dried over Na$_2$SO$_4$, filtered, and concentrated in vacuo to obtain the crude product. The crude material was purified via silica gel column chromatography to afford 4-(4-methoxyphenyl)-1-methyl-3-(4-(quinolin-2-ylmethoxy)phenyl)-1H-pyrrol-2(5H)-one (150 mg, 29%) as a solid. $^1$H NMR (500 MHz, d$_6$-DMSO): δ 8.43-8.39 (m, 1H), 8.04-7.98 (m, 2H), 7.82-7.56 (m, 3H), 7.18-7.09 (m, 4H), 7.04 (d, J=7.2 Hz, 2H), 6.82 (d, J=7.2 Hz, 2H), 5.39 (s, 2H), 4.38 (s, 2H), 3.78 (s, 3H), 2.99 (s, 3H). MS: M$^+$H: m/z=437.1; M$^+$Na: m/z=459.2; M$^+$K: m/z=475.2 and HPLC: 87%, (Condition-B).

Synthesis of 2-methoxy-5-(5-oxo-4-(4-(quinolin-2-ylmethoxy)phenyl)-2,5-dihydrofuran-3-yl)benzonitrile (Example 55)

5-(2-bromoacetyl)-2-methoxybenzonitrile may be prepared by the following scheme

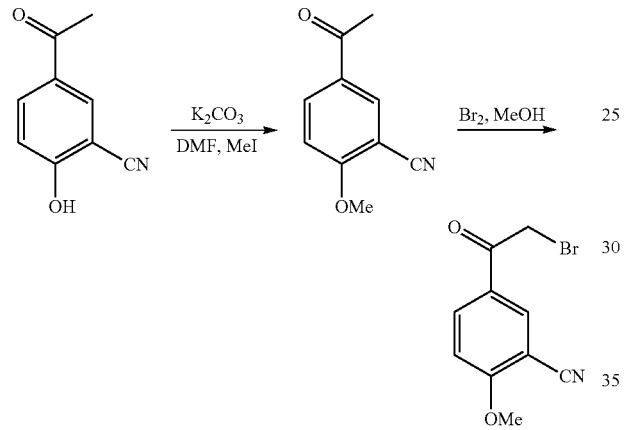

2-Methoxy-5-(5-oxo-4-(4-(quinolin-2-ylmethoxy)phenyl)-2,5-dihydrofuran-3-yl)benzonitrile (Example 55)

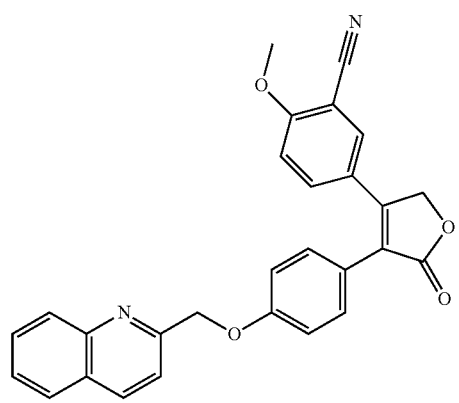 [SMILES: COc1ccc(C2=C(c3ccc(OCc4ccc5ccccc5n4)cc3)C(=O)OC2)cc1C#N]

Following the procedure for the preparation of 4-(3-chloro-4-methoxyphenyl)-3-(4-(quinolin-2-ylmethoxy)phenyl)furan-2(5H)-one-using 5-(2-bromoacetyl)-2-methoxybenzonitrile provided the title compound. $^1$H NMR (500 MHz, d$_6$-DMSO): δ 8.32-8.28 (m, 1H), 8.06-7.95 (m, 2H), 7.81-7.76 (m, 2H), 7.62-7.56 (m, 1H), 7.49-7.39 (m, 2H), 7.26-7.18 (m, 3H), 7.12-7.05 (m, 2H), 5.41 (s, 2H), 5.33 (s, 2H), 3.89 (s, 3H). MS: M$^+$H: m/z=449.0. HPLC: 91%, (Condition-H).

Synthesis of 3-(3-chloro-4-(quinolin-2-ylmethoxy)phenyl)-4-(pyridin-4-yl)furan-2(5H)-one (Example 1099)

Ethyl 2-(3-chloro-4-hydroxyphenyl)acetate

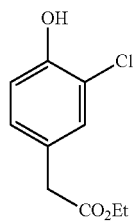

To a 0° C. solution of ethyl 2-(4-hydroxyphenyl)acetate (5.0 g, 0.02 mol) in THF (100 mL) was added NCS (4.45 g, 0.03 mol). The reaction mixture was then stirred at RT for 16 h and then extracted with EtOAc (2×200 mL). The combined organic layers were washed with water, dried over Na$_2$SO$_4$, and concentrated in vacuo to afford ethyl 2-(3-chloro-4-hydroxyphenyl)acetate (5 g, 84%) as a solid.

Ethyl 2-(3-chloro-4-(quinolin-2-ylmethoxy)phenyl)acetate

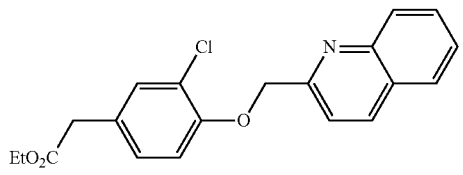 [SMILES: CCOC(=O)Cc1ccc(OCc2ccc3ccccc3n2)c(Cl)c1]

To a solution of compound ethyl 2-(3-chloro-4-hydroxyphenyl)acetate (2.0 g, 0.009 mol) in DMF (10 mL) was added K$_2$CO$_3$ (3.8 g, 0.02 mol) at RT. The reaction mixture was stirred for 10 minutes and then 2-(chloromethyl)quinoline (1.2 g, 0.19 mol) was added. The reaction mixture was refluxed for 16 h, quenched with ice water and filtered. The residue that was obtained was extracted with DCM (2×100 mL). The combined organic layers were washed with water and brine, dried over Na$_2$SO$_4$, and concentrated in vacuo to afford ethyl 2-(3-chloro-4-(quinolin-2-ylmethoxy)phenyl)acetate (1.5 g, 45%) as a solid.

2-(3-Chloro-4-(quinolin-2-ylmethoxy)phenyl)acetic Acid

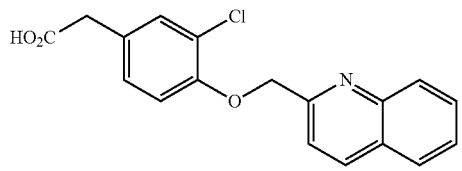 [SMILES: O=C(O)Cc1ccc(OCc2ccc3ccccc3n2)c(Cl)c1]

To a solution of ethyl 2-(3-chloro-4-(quinolin-2-ylmethoxy)phenyl)acetate (1.0 g, 0.02 mol) in 1:1 MeOH:THF (20 mL) was added LiOH.H$_2$O (1.76 g, 0.008 mol). The reaction mixture was then stirred at RT for 16 h and then concentrated in vacuo to obtain the crude product. The crude material was diluted with water and adjusted to pH 4 using 1N HCl. The mixture was then filtered and the residue was dried in vacuo to afford 2-(3-chloro-4-(quinolin-2-ylmethoxy)phenyl)acetic acid (800 mg, 86%) as a solid.

3-(3-chloro-4-(quinolin-2-ylmethoxy)phenyl)-4-(pyridin-4-yl)furan-2(5H)-one (Example 1099)

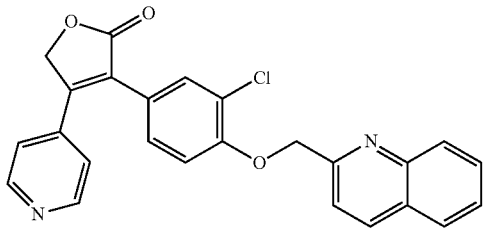 [SMILES: O=C1OCC(c2ccncc2)=C1c1ccc(OCc2ccc3ccccc3n2)c(Cl)c1]

To a stirred solution of 2-(3-chloro-4-(quinolin-2-ylmethoxy)phenyl)acetic acid (6.0 g, 0.01 mol) in acetonitrile (50 mL) were added TEA (2.58 mL, 0.02 mol) and 2-bromo-1-(pyridin-4-yl)ethanone hydrobromide (6.16 g, 0.02 mol) at RT under an inert atmosphere. The reaction mixture was stirred for 30 minutes, cooled to 0° C., and then DBU (5.5 mL, 0.03 mol) was added. The reaction was stirred for an additional 15 minutes and then quenched with HCl (1 N) and extracted with DCM (2×300 mL). The combined organic layers were washed with water, dried over $Na_2SO_4$, and concentrated in vacuo to obtain the crude product. The crude material was purified via silica gel column chromatography to afford 3-(3-chloro-4-(quinolin-2-ylmethoxy)phenyl)-4-(pyridin-4-yl)furan-2(5H)-one (500 mg) as a solid. $^1$H NMR (500 MHz, $d_6$-DMSO): δ 8.64 (d, J=7.8 Hz, 2H), 8.50-8.44 (m, 1H), 8.04-7.98 (m, 2H), 7.8 (t, J=7.2 Hz, 1H), 7.74 (d, J=7.6 Hz, 1H), 7.64 (t, J=7.2 Hz, 1H), 7.50 (s, 1H), 7.38-7.32 (m, 3H), 7.26-7.22 (m, 1H), 5.55 (s, 2H), 5.38 (s, 2H). MS: $M^+H$: m/z=429.1. HPLC: 90%, (Condition-I).

Tables

In the following tables of examples, if a specific example contains a single value in the column "$R_{1a}$ and $R_{1b}$", then both $R_{1a}$ and $R_{1b}$ (if present) are taken to be this value. If this column contains multiple values separated by a comma, the first value is taken to be $R_{1a}$ and the second to be $R_{1b}$. In the following tables, if a specific example contains multiple instances of $R_2$, they will be separated by commas in the table (e.g. Me, Me or Et, Me). If the $R_2$ column contains a value "--group--" e.g. "--cyclopropyl--", then both $R_2$ values are taken together to be a spiro ring.

In a further aspect the compounds of the disclosure are embodied in with distinct examples listed in the table below taken from Formula (I):

| Ex. # | HET | X | Y | Z | $R_{1a}$, $R_{1b}$ | $R_2$ | $R_3$ | $R_4$ | $R_7$ |
|---|---|---|---|---|---|---|---|---|---|
| 1 | A1 | 4-pyridinyl | $OCH_2$ | 2-quinoline | — | — | H | H | — |
| 2 | A1 | 4-pyridinyl | $OCH_2$ | 2-benzimidazole | — | — | H | H | — |
| 3 | A1 | 4-pyridinyl | $OCH_2$ | 2-tetrahydroisoquinoline | — | — | H | H | — |
| 4 | A1 | 4-pyridinyl | $OCH_2$ | 2-pyridinyl | — | — | H | H | — |
| 5 | A1 | 4-pyridinyl | $OCH_2$ | 2-benzoxazole | — | — | H | H | — |
| 6 | A1 | 4-pyridinyl | $OCH_2$ | 2-benzthiazole | — | — | H | H | — |
| 7 | A1 | 4-pyridinyl | $OCH_2$ | 2-quinoxaline | — | — | H | H | — |
| 8 | A1 | 4-pyridinyl | $OCH_2$ | 2-naphthyridine | — | — | H | H | — |
| 9 | A1 | 4-pyridinyl | $OCH_2$ | 2-quinazoline | — | — | H | H | — |
| 10 | A1 | 3-pyridinyl | $OCH_2$ | 2-quinoline | — | — | H | H | — |
| 11 | A1 | 3,4-diOMe—Ph | $OCH_2$ | 2-quinoline | — | — | H | H | — |
| 12 | A1 | 3-Me-4-pyridinyl | $OCH_2$ | 2-quinoline | — | — | H | H | — |
| 13 | A1 | 3-OMe-4-pyridinyl | $OCH_2$ | 2-quinoline | — | — | H | H | — |
| 14 | A1 | 4-OMe-phenyl | $OCH_2$ | 2-quinoline | — | — | H | H | — |
| 15 | A1 | 4-pyridinyl | $CH_2O$ | 2-quinoline | — | — | H | H | — |
| 16 | A2 | 4-pyridinyl | $OCH_2$ | 2-quinoline | — | — | H | H | H |
| 17 | A2 | 4-pyridinyl | $OCH_2$ | 2-benzimidazole | — | — | H | H | Me |
| 18 | A2 | 4-pyridinyl | $OCH_2$ | 2-tetrahydroisoquinoline | — | — | H | H | Me |
| 19 | A2 | 4-pyridinyl | $OCH_2$ | 2-pyridinyl | — | — | H | H | Me |
| 20 | A2 | 4-pyridinyl | $OCH_2$ | 2-benzoxazole | — | — | H | H | Me |
| 21 | A2 | 4-pyridinyl | $OCH_2$ | 2-benzthiazole | — | — | H | H | Me |
| 22 | A2 | 4-pyridinyl | $OCH_2$ | 2-quinoxaline | — | — | H | H | Me |
| 23 | A2 | 4-pyridinyl | $OCH_2$ | 2-naphthyridine | — | — | H | H | Me |
| 24 | A2 | 4-pyridinyl | $OCH_2$ | 2-quinazoline | — | — | H | H | Me |
| 25 | A2 | 3-pyridinyl | $OCH_2$ | 2-quinoline | — | — | H | H | H |
| 26 | A2 | 3,4-diOMe—Ph | $OCH_2$ | 2-quinoline | — | — | H | H | H |
| 27 | A2 | 3-Me-4-pyridinyl | $OCH_2$ | 2-quinoline | — | — | H | H | H |
| 28 | A2 | 3-OMe-4-pyridinyl | $OCH_2$ | 2-quinoline | — | — | H | H | H |
| 29 | A2 | 4-OMe-phenyl | $OCH_2$ | 2-quinoline | — | — | H | H | H |
| 30 | A2 | 4-pyridinyl | $OCH_2$ | 2-quinoline | — | — | H | H | Me |
| 31 | A2 | 4-pyridinyl | $CH_2O$ | 2-quinoline | — | — | H | H | H |
| 32 | A2 | 4-pyridinyl | $CH_2O$ | 2-quinoline | — | — | H | H | Me |
| 33 | A3 | 4-pyridinyl | $OCH_2$ | 2-quinoline | — | — | — | — | H |
| 34 | A3 | 4-pyridinyl | $CH_2O$ | 2-quinoline | — | — | — | — | H |
| 35 | A6 | 4-pyridinyl | $OCH_2$ | 2-quinoline | H, — | — | — | — | H |
| 36 | A6 | 4-pyridinyl | $CH_2O$ | 2-quinoline | H, — | — | — | — | H |
| 37 | A7 | 4-pyridinyl | $OCH_2$ | 2-quinoline | — | — | H | H | — |
| 38 | A7 | 4-pyridinyl | $OCH_2$ | 2-tetrahydroisoquinoline | — | — | H | H | — |
| 39 | A7 | 4-pyridinyl | $OCH_2$ | 2-pyridinyl | — | — | H | H | — |
| 40 | A7 | 4-pyridinyl | $OCH_2$ | 2-benzoxazole | — | — | H | H | — |
| 41 | A7 | 4-pyridinyl | $OCH_2$ | 2-benzthiazole | — | — | H | H | — |
| 42 | A7 | 4-pyridinyl | $OCH_2$ | 2-quinoxaline | — | — | H | H | — |
| 43 | A7 | 4-pyridinyl | $OCH_2$ | 2-naphthyridine | — | — | H | H | — |
| 44 | A7 | 4-pyridinyl | $OCH_2$ | 2-quinazoline | — | — | H | H | — |
| 45 | A7 | 4-pyridinyl | $CH_2O$ | 2-quinoline | — | — | H | H | — |
| 46 | A7 | 4-pyramidinyl | $OCH_2$ | 2-quinoline | — | — | H | H | — |
| 47 | A7 | 4-pyrazolyl | $OCH_2$ | 2-quinoline | — | — | H | H | — |

-continued

| Ex. # | HET | X | Y | Z | R₁ₐ, R₁ᵦ | R₂ | R₃ | R₄ | R₇ |
|---|---|---|---|---|---|---|---|---|---|
| 48 | A7 | 5-pyridin-2(1H)-onyl | OCH₂ | 2-quinoline | — | — | H | H | — |
| 49 | A7 | 4-pyridin-2(1H)-onyl | OCH₂ | 2-quinoline | — | — | H | H | — |
| 50 | A7 | 4-pyridazinyl | OCH₂ | 2-quinoline | — | — | H | H | — |
| 51 | A7 | 3-(1-methyl-1H-pyrazolyl) | OCH₂ | 2-quinoline | — | — | H | H | — |
| 52 | A7 | 4-(1-methyl-1H-pyrazolyl) | OCH₂ | 2-quinoline | — | — | H | H | — |
| 53 | A7 | 3-F,4-OMe phenyl | OCH₂ | 2-quinoline | — | — | H | H | — |
| 54 | A7 | 3-Cl,4-OMe phenyl | OCH₂ | 2-quinoline | — | — | H | H | — |
| 55 | A7 | 3-CN,4-OMe phenyl | OCH₂ | 2-quinoline | — | — | H | H | — |
| 56 | A7 | 3-OMe,4-F phenyl | OCH₂ | 2-quinoline | — | — | H | H | — |
| 57 | A7 | 3-OMe,4-Cl phenyl | OCH₂ | 2-quinoline | — | — | H | H | — |
| 58 | A7 | 3-OMe,4-CN phenyl | OCH₂ | 2-quinoline | — | — | H | H | — |
| 59 | A7 | 4-MeO-phenyl | OCH₂ | 2-quinoline | — | — | H | H | — |
| 60 | A7 | 4-NC-phenyl | OCH₂ | 2-quinoline | — | — | H | H | — |
| 61 | A7 | 4-Cl-phenyl | OCH₂ | 2-quinoline | — | — | H | H | — |
| 62 | A7 | 4-F-phenyl | OCH₂ | 2-quinoline | — | — | H | H | — |
| 63 | A7 | 4-F₃C-phenyl | OCH₂ | 2-quinoline | — | — | H | H | — |
| 64 | A7 | 4-CF₃O-phenyl | OCH₂ | 2-quinoline | — | — | H | H | — |
| 65 | A7 | 4-F₃CH₂C-phenyl | OCH₂ | 2-quinoline | — | — | H | H | — |
| 66 | A7 | 4-EtO-phenyl | OCH₂ | 2-quinoline | — | — | H | H | — |

-continued

| Ex. # | HET | X | Y Z | $R_{1a}, R_{1b}$ | $R_2$ | $R_3$ | $R_4$ | $R_7$ |
|---|---|---|---|---|---|---|---|---|
| 67 | A7 | iPrO-C6H4- | OCH$_2$ 2-quinoline | — | — | H | H | — |
| 68 | A7 | F$_2$CHO-C6H4- | OCH$_2$ 2-quinoline | — | — | H | H | — |
| 69 | A7 | cyclopropyl-O-C6H4- | OCH$_2$ 2-quinoline | — | — | H | H | — |
| 70 | A7 | cyclopropyl-CH$_2$-O-C6H4- | OCH$_2$ 2-quinoline | — | — | H | H | — |
| 71 | A7 | CF$_3$CH$_2$O-C6H4- | OCH$_2$ 2-quinoline | — | — | H | H | — |
| 72 | A7 | Br-C6H4- | OCH$_2$ 2-quinoline | — | — | H | H | — |
| 73 | A7 | O$_2$N-C6H4- | OCH$_2$ 2-quinoline | — | — | H | H | — |
| 74 | A7 | F$_2$CH-C6H4- | OCH$_2$ 2-quinoline | — | — | H | H | — |
| 75 | A7 | benzofurazanyl | OCH$_2$ 2-quinoline | — | — | H | H | — |

-continued

| Ex. # | HET | X | Y | Z | R₁ₐ, R₁ᵦ | R₂ | R₃ | R₄ | R₇ |
|---|---|---|---|---|---|---|---|---|---|
| 76 | A7 | benzothiadiazole | | OCH₂ | 2-quinoline | — | — | H | H | — |
| 77 | A7 | 2-(difluoromethoxy)-3-chlorophenyl | | OCH₂ | 2-quinoline | — | — | H | H | — |
| 78 | A7 | 2-(difluoromethoxy)-3-cyanophenyl | | OCH₂ | 2-quinoline | — | — | H | H | — |
| 79 | A7 | 1-tetrazolyl | | OCH₂ | 2-quinoline | — | — | H | H | — |
| 80 | A7 | oxazol-5-yl | | OCH₂ | 2-quinoline | — | — | H | H | — |
| 81 | A7 | oxazol-4-yl | | OCH₂ | 2-quinoline | — | — | H | H | — |
| 82 | A7 | thiazol-5-yl | | OCH₂ | 2-quinoline | — | — | H | H | — |
| 83 | A7 | thiazol-4-yl | | OCH₂ | 2-quinoline | — | — | H | H | — |
| 84 | A7 | 2H-tetrazol-5-yl | | OCH₂ | 2-quinoline | — | — | H | H | — |
| 85 | A8 | 4-pyridinyl | | OCH₂ | 2-quinoline | — | — | H | H | H |
| 86 | A8 | 4-pyridinyl | | OCH₂ | 2-benzimidazole | — | — | H | H | Me |
| 87 | A8 | 4-pyridinyl | | OCH₂ | 2-tetrahydroisoquinoline | — | — | H | H | Me |
| 88 | A8 | 4-pyridinyl | | OCH₂ | 2-pyridinyl | — | — | H | H | Me |
| 89 | A8 | 4-pyridinyl | | OCH₂ | 2-benzoxazole | — | — | H | H | Me |
| 90 | A8 | 4-pyridinyl | | OCH₂ | 2-benzthiazole | — | — | H | H | Me |
| 91 | A8 | 4-pyridinyl | | OCH₂ | 2-quinoxaline | — | — | H | H | Me |

-continued

| Ex. # | HET | X | Y | Z | R1a, R1b | R2 | R3 | R4 | R7 |
|---|---|---|---|---|---|---|---|---|---|
| 92 | A8 | 4-pyridinyl | OCH2 | 2-naphthyridine | — | — | H | H | Me |
| 93 | A8 | 4-pyridinyl | OCH2 | 2-quinazoline | — | — | H | H | Me |
| 94 | A8 | 4-pyridinyl | OCH2 | 2-quinoline | — | — | H | H | Me |
| 95 | A8 | 4-pyridinyl | CH2O | 2-quinoline | — | — | H | H | H |
| 96 | A8 | 4-pyridinyl | CH2O | 2-quinoline | — | — | H | H | Me |
| 97 | A8 | 4-pyridinyl | OCH2 | 2-quinoline | — | — | H | H | cyclopropyl |
| 98 | A8 | 4-pyridinyl | OCH2 | 2-quinoline | — | — | H | H | —CH2CF3 |
| 99 | A8 | MeO-C6H4- | OCH2 | 2-quinoline | — | — | H | H | H |
| 100 | A8 | NC-C6H4- | OCH2 | 2-quinoline | — | — | H | H | H |
| 101 | A8 | Cl-C6H4- | OCH2 | 2-quinoline | — | — | H | H | H |
| 102 | A8 | F-C6H4- | OCH2 | 2-quinoline | — | — | H | H | H |
| 103 | A8 | F3C-C6H4- | OCH2 | 2-quinoline | — | — | H | H | H |
| 104 | A8 | CF3O-C6H4- | OCH2 | 2-quinoline | — | — | H | H | H |
| 105 | A8 | F3CH2C-C6H4- | OCH2 | 2-quinoline | — | — | H | H | H |
| 106 | A8 | EtO-C6H4- | OCH2 | 2-quinoline | — | — | H | H | H |
| 107 | A8 | iPrO-C6H4- | OCH2 | 2-quinoline | — | — | H | H | H |

-continued

| Ex. # | HET | X | Y | Z | $R_{1a}, R_{1b}$ | $R_2$ | $R_3$ | $R_4$ | $R_7$ |
|---|---|---|---|---|---|---|---|---|---|
| 108 | A8 | F₂CHO-C₆H₄- | OCH₂ | 2-quinoline | — | — | H | H | H |
| 109 | A8 | cyclopropyl-O-C₆H₄- | OCH₂ | 2-quinoline | — | — | H | H | H |
| 110 | A8 | cyclopropyl-CH₂-O-C₆H₄- | OCH₂ | 2-quinoline | — | — | H | H | H |
| 111 | A8 | CF₃CH₂-O-C₆H₄- | OCH₂ | 2-quinoline | — | — | H | H | H |
| 112 | A8 | Br-C₆H₄- | OCH₂ | 2-quinoline | — | — | H | H | H |
| 113 | A8 | O₂N-C₆H₄- | OCH₂ | 2-quinoline | — | — | H | H | H |
| 114 | A8 | F₂CH-C₆H₄- | OCH₂ | 2-quinoline | — | — | H | H | H |
| 115 | A8 | benzo[1,2,5]oxadiazol-5-yl | OCH₂ | 2-quinoline | — | — | H | H | H |
| 116 | A8 | benzo[1,2,5]thiadiazol-5-yl | OCH₂ | 2-quinoline | — | — | H | H | H |

-continued

| Ex. # | HET | X | Y | Z | R$_{1a}$, R$_{1b}$ | R$_2$ | R$_3$ | R$_4$ | R$_7$ |
|---|---|---|---|---|---|---|---|---|---|
| 117 | A8 | 3-Cl-4-(OCHF$_2$)phenyl | OCH$_2$ | 2-quinoline | — | — | H | H | H |
| 118 | A8 | 2-(OCHF$_2$)-5-CN-phenyl | OCH$_2$ | 2-quinoline | — | — | H | H | H |
| 119 | A8 | 1-tetrazolyl | OCH$_2$ | 2-quinoline | — | — | H | H | H |
| 120 | A8 | 5-oxazolyl | OCH$_2$ | 2-quinoline | — | — | H | H | H |
| 121 | A8 | 4-oxazolyl | OCH$_2$ | 2-quinoline | — | — | H | H | H |
| 122 | A8 | 5-thiazolyl | OCH$_2$ | 2-quinoline | — | — | H | H | H |
| 123 | A8 | 4-thiazolyl | OCH$_2$ | 2-quinoline | — | — | H | H | H |
| 124 | A8 | 5-(2H-tetrazolyl) | OCH$_2$ | 2-quinoline | — | — | H | H | H |
| 125 | A8 | 4-MeO-phenyl | OCH$_2$ | 2-quinoline | — | — | H | H | Me |
| 126 | A8 | 4-CN-phenyl | OCH$_2$ | 2-quinoline | — | — | H | H | Me |

-continued

| Ex. # | HET | X | Y | Z | $R_{1a}, R_{1b}$ | $R_2$ | $R_3$ | $R_4$ | $R_7$ |
|---|---|---|---|---|---|---|---|---|---|
| 127 | A8 | Cl-C6H4- (4-Cl-phenyl) | OCH$_2$ | 2-quinoline | — | — | H | H | Me |
| 128 | A8 | F-C6H4- (4-F-phenyl) | OCH$_2$ | 2-quinoline | — | — | H | H | Me |
| 129 | A8 | F$_3$C-C6H4- (4-CF$_3$-phenyl) | OCH$_2$ | 2-quinoline | — | — | H | H | Me |
| 130 | A8 | CF$_3$O-C6H4- (4-OCF$_3$-phenyl) | OCH$_2$ | 2-quinoline | — | — | H | H | Me |
| 131 | A8 | F$_3$CH$_2$C-C6H4- (4-CH$_2$CF$_3$-phenyl) | OCH$_2$ | 2-quinoline | — | — | H | H | Me |
| 132 | A8 | EtO-C6H4- (4-OEt-phenyl) | OCH$_2$ | 2-quinoline | — | — | H | H | Me |
| 133 | A8 | iPrO-C6H4- (4-OiPr-phenyl) | OCH$_2$ | 2-quinoline | — | — | H | H | Me |
| 134 | A8 | F$_2$CHO-C6H4- (4-OCHF$_2$-phenyl) | OCH$_2$ | 2-quinoline | — | — | H | H | Me |
| 135 | A8 | cyclopropyl-O-C6H4- | OCH$_2$ | 2-quinoline | — | — | H | H | Me |
| 136 | A8 | cyclopropyl-CH$_2$-O-C6H4- | OCH$_2$ | 2-quinoline | — | — | H | H | Me |

| Ex. # | HET | X | Y Z | $R_{1a}, R_{1b}$ | $R_2$ | $R_3$ | $R_4$ | $R_7$ |
|---|---|---|---|---|---|---|---|---|
| 137 | A8 | 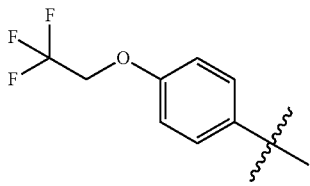 [SMILES: *c1ccc(OCC(F)(F)F)cc1] | OCH$_2$ 2-quinoline | — | — | H | H | Me |
| 138 | A8 | 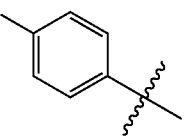 | OCH$_2$ 2-quinoline | — | — | H | H | Me |
| 139 | A8 | 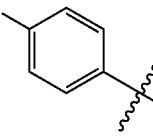 | OCH$_2$ 2-quinoline | — | — | H | H | Me |
| 140 | A8 | 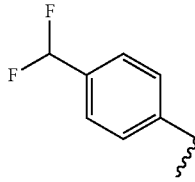 | OCH$_2$ 2-quinoline | — | — | H | H | Me |
| 141 | A8 | 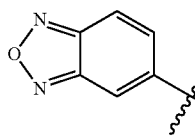 | OCH$_2$ 2-quinoline | — | — | H | H | Me |
| 142 | A8 | 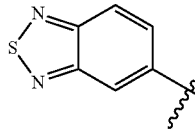 | OCH$_2$ 2-quinoline | — | — | H | H | Me |
| 143 | A8 | 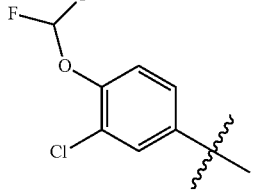 | OCH$_2$ 2-quinoline | — | — | H | H | Me |
| 144 | A8 | 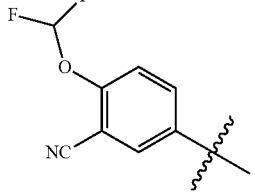 | OCH$_2$ 2-quinoline | — | — | H | H | Me |
| 145 | A8 | 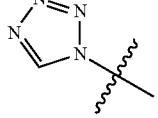 | OCH$_2$ 2-quinoline | — | — | H | H | Me |

-continued

| Ex. # | HET | X | Y | Z | R1a, R1b | R2 | R3 | R4 | R7 |
|---|---|---|---|---|---|---|---|---|---|
| 146 | A8 | oxazol-5-yl | OCH2 | 2-quinoline | — | — | H | H | Me |
| 147 | A8 | oxazol-4-yl | OCH2 | 2-quinoline | — | — | H | H | Me |
| 148 | A8 | thiazol-5-yl | OCH2 | 2-quinoline | — | — | H | H | Me |
| 149 | A8 | thiazol-4-yl | OCH2 | 2-quinoline | — | — | H | H | Me |
| 150 | A8 | 2H-tetrazol-5-yl | OCH2 | 2-quinoline | — | — | H | H | Me |
| 151 | A10 | 4-pyridinyl | OCH2 | 2-quinoline | H, — | — | — | — | — |
| 153 | A11 | 4-pyridinyl | OCH2 | 2-quinoline | H, — | — | — | — | — |
| 154 | A11 | 4-pyridinyl | CH2O | 2-quinoline | H, — | — | — | — | — |
| 155 | A12 | 4-pyridinyl | OCH2 | 2-quinoline | H, — | — | — | — | — |
| 156 | A12 | 4-pyridinyl | CH2O | 2-quinoline | H, — | — | — | — | — |
| 157 | A13 | 4-pyridinyl | OCH2 | 2-quinoline | H, H | — | — | — | — |
| 158 | A13 | 4-pyridinyl | CH2O | 2-quinoline | H, H | — | — | — | — |
| 159 | A14 | 4-pyridinyl | OCH2 | 2-quinoline | H, H | — | — | — | — |
| 160 | A14 | 4-pyridinyl | CH2O | 2-quinoline | H, H | — | — | — | — |
| 161 | A14 | 4-pyridinyl | CH2O | 2-quinoline | H, Me | — | — | — | — |
| 162 | A15 | 4-pyridinyl | OCH2 | 2-quinoline | H, — | — | — | — | — |
| 163 | A15 | 4-pyridinyl | CH2O | 2-quinoline | H, — | — | — | — | — |
| 164 | A25 | 4-pyridinyl | OCH2 | 2-quinoline | — | H | — | — | — |
| 165 | A29 | pyrimidin-4-yl | OCH2 | 2-quinoline | — | H, H | — | — | — |
| 166 | A29 | 1,3,5-triazin-2-yl | OCH2 | 2-quinoline | — | H, H | — | — | — |
| 167 | A29 | pyridazin-4-yl | OCH2 | 2-quinoline | — | H, H | — | — | — |
| 168 | A29 | 2-hydroxypyridin-4-yl | OCH2 | 2-quinoline | — | H, H | — | — | — |

-continued

| Ex. # | HET | X | Y | Z | R$_{1a}$, R$_{1b}$ | R$_2$ | R$_3$ | R$_4$ | R$_7$ |
|---|---|---|---|---|---|---|---|---|---|
| 169 | A29 | 2-methoxypyridin-4-yl | OCH$_2$ | 2-quinoline | — | H, H | — | — | — |
| 170 | A29 | 2-hydroxypyridin-5-yl | OCH$_2$ | 2-quinoline | — | H, H | — | — | — |
| 171 | A29 | 2-methoxypyridin-5-yl | OCH$_2$ | 2-quinoline | — | H, H | — | — | — |
| 172 | A29 | 3-fluoro-4-methoxyphenyl | OCH$_2$ | 2-quinoline | — | H, H | — | — | — |
| 173 | A29 | 3-chloro-4-methoxyphenyl | OCH$_2$ | 2-quinoline | — | H, H | — | — | — |
| 174 | A29 | 3-bromo-4-methoxyphenyl | OCH$_2$ | 2-quinoline | — | H, H | — | — | — |
| 175 | A29 | 3-cyano-4-methoxyphenyl | OCH$_2$ | 2-quinoline | — | H, H | — | — | — |
| 176 | A29 | 4-methoxyphenyl | OCH$_2$ | 2-quinoline | — | H, H | — | — | — |
| 177 | A29 | 4-cyanophenyl | OCH$_2$ | 2-quinoline | — | H, H | — | — | — |

-continued

| Ex. # | HET | X | Y | Z | $R_{1a}, R_{1b}$ | $R_2$ | $R_3$ | $R_4$ | $R_7$ |
|---|---|---|---|---|---|---|---|---|---|
| 178 | A29 | 4-CN, 3-F phenyl | OCH$_2$ | 2-quinoline | — | H, H | — | — | — |
| 179 | A29 | 4-CN, 3-Cl phenyl | OCH$_2$ | 2-quinoline | — | H, H | — | — | — |
| 180 | A29 | 4-CN, 3-Br phenyl | OCH$_2$ | 2-quinoline | — | H, H | — | — | — |
| 181 | A29 | 4-CN, 3-OMe phenyl | OCH$_2$ | 2-quinoline | — | H, H | — | — | — |
| 182 | A29 | 3,4-diCN phenyl | OCH$_2$ | 2-quinoline | — | H, H | — | — | — |
| 183 | A29 | 4-Cl phenyl | OCH$_2$ | 2-quinoline | — | H, H | — | — | — |
| 184 | A29 | 4-Cl, 3-F phenyl | OCH$_2$ | 2-quinoline | — | H, H | — | — | — |
| 185 | A29 | 3,4-diCl phenyl | OCH$_2$ | 2-quinoline | — | H, H | — | — | — |

-continued

| Ex. # | HET | X | Y | Z | $R_{1a}, R_{1b}$ | $R_2$ | $R_3$ | $R_4$ | $R_7$ |
|---|---|---|---|---|---|---|---|---|---|
| 186 | A29 | 4-Cl, 3-Br-phenyl | OCH$_2$ | 2-quinoline | — | H, H | — | — | — |
| 187 | A29 | 4-Cl, 3-OMe-phenyl | OCH$_2$ | 2-quinoline | — | H, H | — | — | — |
| 188 | A29 | 4-Cl, 3-CN-phenyl | OCH$_2$ | 2-quinoline | — | H, H | — | — | — |
| 189 | A29 | 4-F-phenyl | OCH$_2$ | 2-quinoline | — | H, H | — | — | — |
| 190 | A29 | 4-F$_3$C-phenyl | OCH$_2$ | 2-quinoline | — | H, H | — | — | — |
| 191 | A29 | 4-CF$_3$O-phenyl | OCH$_2$ | 2-quinoline | — | H, H | — | — | — |
| 192 | A29 | 4-F$_3$CH$_2$C-phenyl | OCH$_2$ | 2-quinoline | — | H, H | — | — | — |
| 193 | A29 | 4-EtO-phenyl | OCH$_2$ | 2-quinoline | — | H, H | — | — | — |
| 194 | A29 | 4-iPrO-phenyl | OCH$_2$ | 2-quinoline | — | H, H | — | — | — |

-continued

| Ex. # | HET | X | Y Z | $R_{1a}, R_{1b}$ | $R_2$ | $R_3$ | $R_4$ | $R_7$ |
|---|---|---|---|---|---|---|---|---|
| 195 | A29 | F$_2$CHO-phenyl- | OCH$_2$ 2-quinoline | — | H, H | — | — | — |
| 196 | A29 | cyclopropyl-O-phenyl- | OCH$_2$ 2-quinoline | — | H, H | — | — | — |
| 197 | A29 | cyclopropyl-CH$_2$-O-phenyl- | OCH$_2$ 2-quinoline | — | H, H | — | — | — |
| 198 | A29 | CF$_3$CH$_2$-O-phenyl- | OCH$_2$ 2-quinoline | — | H, H | — | — | — |
| 199 | A29 | Br-phenyl- | OCH$_2$ 2-quinoline | — | H, H | — | — | — |
| 200 | A29 | O$_2$N-phenyl- | OCH$_2$ 2-quinoline | — | H, H | — | — | — |
| 201 | A29 | F$_2$CH-phenyl- | OCH$_2$ 2-quinoline | — | H, H | — | — | — |
| 202 | A29 | benzoxadiazolyl | OCH$_2$ 2-quinoline | — | H, H | — | — | — |
| 203 | A29 | benzothiadiazolyl | OCH$_2$ 2-quinoline | — | H, H | — | — | — |

-continued

| Ex. # | HET | X | Y | Z | R₁ₐ, R₁ᵦ | R₂ | R₃ | R₄ | R₇ |
|---|---|---|---|---|---|---|---|---|---|
| 204 | A29 | 3-chloro-4-(difluoromethoxy)phenyl | OCH₂ | 2-quinoline | — | H, H | — | — | — |
| 205 | A29 | 2-(difluoromethoxy)-5-cyanophenyl | OCH₂ | 2-quinoline | — | H, H | — | — | — |
| 206 | A29 | 1H-tetrazol-1-yl-methyl | OCH₂ | 2-quinoline | — | H, H | — | — | — |
| 207 | A29 | oxazol-5-yl | OCH₂ | 2-quinoline | — | H, H | — | — | — |
| 208 | A29 | oxazol-4-yl | OCH₂ | 2-quinoline | — | H, H | — | — | — |
| 209 | A29 | thiazol-5-yl | OCH₂ | 2-quinoline | — | H, H | — | — | — |
| 210 | A29 | thiazol-4-yl | OCH₂ | 2-quinoline | — | H, H | — | — | — |
| 211 | A29 | 2H-tetrazol-5-yl | OCH₂ | 2-quinoline | — | H, H | — | — | — |
| 212 | A29 | 4-fluorophenyl | OCH₂ | 3,5-dimethylpyridin-2-yl | — | H, H | — | — | — |
| 213 | A29 | 4-(trifluoromethyl)phenyl | OCH₂ | 3,5-dimethylpyridin-2-yl | — | H, H | — | — | — |

-continued

| Ex. # | HET | X | Y | Z | R_{1a}, R_{1b} | R_2 | R_3 | R_4 | R_7 |
|---|---|---|---|---|---|---|---|---|---|
| 214 | A29 | CF₃O-phenyl | OCH₂ | 3,5-dimethylpyridin-2-yl | — | H, H | — | — | — |
| 215 | A29 | F₃CH₂C-phenyl | OCH₂ | 3,5-dimethylpyridin-2-yl | — | H, H | — | — | — |
| 216 | A29 | EtO-phenyl | OCH₂ | 3,5-dimethylpyridin-2-yl | — | H, H | — | — | — |
| 217 | A29 | iPrO-phenyl | OCH₂ | 3,5-dimethylpyridin-2-yl | — | H, H | — | — | — |
| 218 | A29 | CHF₂O-phenyl | OCH₂ | 3,5-dimethylpyridin-2-yl | — | H, H | — | — | — |
| 219 | A29 | cyclopropyl-O-phenyl | OCH₂ | 3,5-dimethylpyridin-2-yl | — | H, H | — | — | — |
| 220 | A29 | cyclopropyl-CH₂O-phenyl | OCH₂ | 3,5-dimethylpyridin-2-yl | — | H, H | — | — | — |
| 221 | A29 | CF₃CH₂O-phenyl | OCH₂ | 3,5-dimethylpyridin-2-yl | — | H, H | — | — | — |
| 222 | A29 | Br-phenyl | OCH₂ | 3,5-dimethylpyridin-2-yl | — | H, H | — | — | — |
| 223 | A29 | O₂N-phenyl | OCH₂ | 3,5-dimethylpyridin-2-yl | — | H, H | — | — | — |

-continued
| Ex. # | HET | X | Y | Z | R$_{1a}$, R$_{1b}$ | R$_2$ | R$_3$ | R$_4$ | R$_7$ |
|---|---|---|---|---|---|---|---|---|---|
| 224 | A29 | 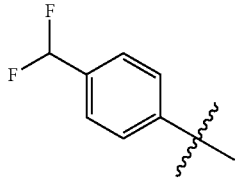 [SMILES: *c1ccc(C(F)F)cc1] | OCH$_2$ | 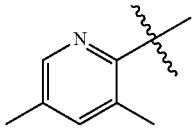 | — | H, H | — | — | — |
| 225 | A29 | 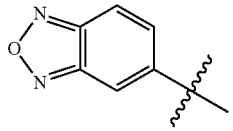 | OCH$_2$ | 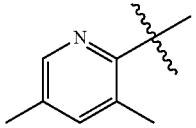 | — | H, H | — | — | — |
| 226 | A29 | 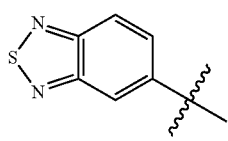 | OCH$_2$ | 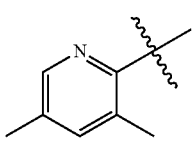 | — | H, H | — | — | — |
| 227 | A29 | 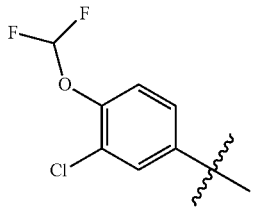 [SMILES: *c1ccc(OC(F)F)c(Cl)c1] | OCH$_2$ | 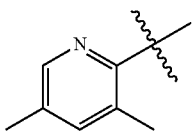 | — | H, H | — | — | — |
| 228 | A29 | 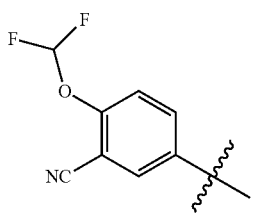 [SMILES: *c1ccc(OC(F)F)c(C#N)c1] | OCH$_2$ | 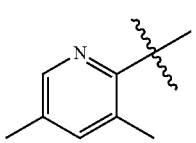 | — | H, H | — | — | — |
| 229 | A29 | 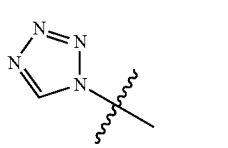 [SMILES: *n1cnnn1] | OCH$_2$ | 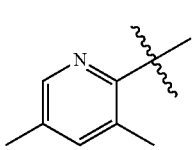 | — | H, H | — | — | — |
| 230 | A29 | 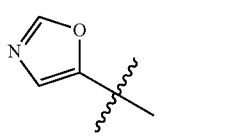 | OCH$_2$ | 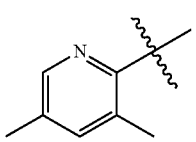 | — | H, H | — | — | — |
| 231 | A29 | 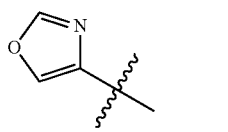 [SMILES: *c1cocn1] | OCH$_2$ | 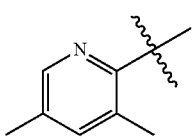 | — | H, H | — | — | — |
| 232 | A29 | 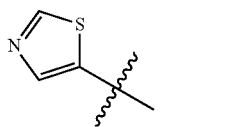 [SMILES: *c1cncs1] | OCH$_2$ | 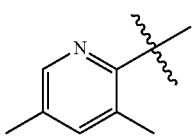 | — | H, H | — | — | — |

-continued
| Ex. # | HET | X | Y | Z | R1a, R1b | R2 | R3 | R4 | R7 |
|---|---|---|---|---|---|---|---|---|---|
| 233 | A29 | 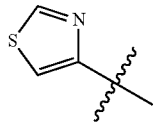 | OCH2 | 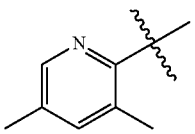 | — | H, H | — | — | — |
| 234 | A29 | 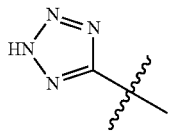 [SMILES: *c1nn[nH]n1] | OCH2 | 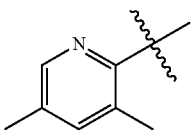 | — | H, H | — | — | — |
| 235 | A29 | 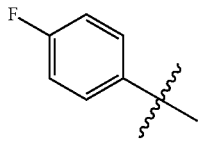 [SMILES: *c1ccc(F)cc1] | OCH2 | 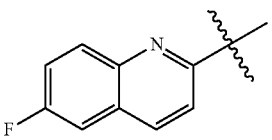 [SMILES: *c1ccc2cc(F)ccc2n1] | — | H, H | — | — | — |
| 236 | A29 | 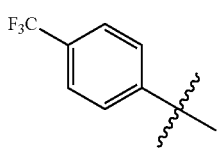 [SMILES: *c1ccc(C(F)(F)F)cc1] | OCH2 | 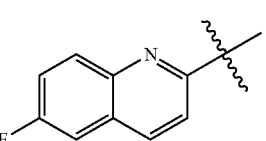 | — | H, H | — | — | — |
| 237 | A29 | 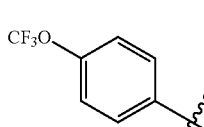 | OCH2 | 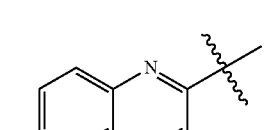 | — | H, H | — | — | — |
| 238 | A29 | 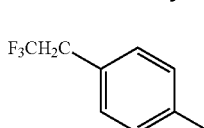 | OCH2 | 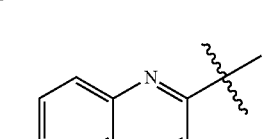 | — | H, H | — | — | — |
| 239 | A29 | 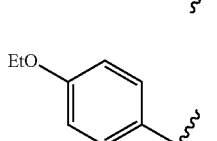 | OCH2 | 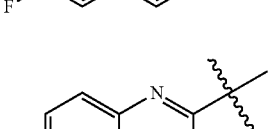 | — | H, H | — | — | — |
| 240 | A29 | 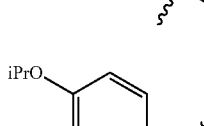 | OCH2 | 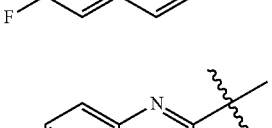 | — | H, H | — | — | — |
| 241 | A29 | 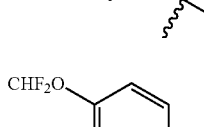 | OCH2 | 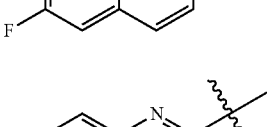 | — | H, H | — | — | — |
| 242 | A29 | 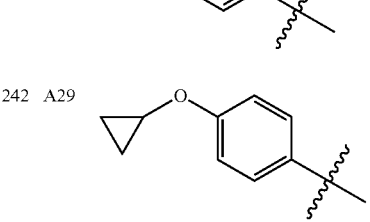 | OCH2 | 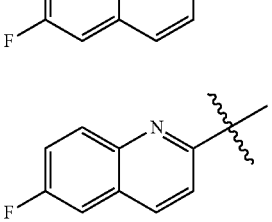 | — | H, H | — | — | — |

-continued

| Ex. # | HET | X | Y Z | | $R_{1a}, R_{1b}$ | $R_2$ | $R_3$ | $R_4$ | $R_7$ |
|---|---|---|---|---|---|---|---|---|---|
| 243 | A29 | cyclopropylmethoxy-phenyl | OCH$_2$ | 6-fluoroquinolin-2-yl | — | H, H | — | — | — |
| 244 | A29 | 2,2,2-trifluoroethoxy-phenyl | OCH$_2$ | 6-fluoroquinolin-2-yl | — | H, H | — | — | — |
| 245 | A29 | 4-bromophenyl | OCH$_2$ | 6-fluoroquinolin-2-yl | — | H, H | — | — | — |
| 246 | A29 | 4-nitrophenyl | OCH$_2$ | 6-fluoroquinolin-2-yl | — | H, H | — | — | — |
| 247 | A29 | 4-(difluoromethyl)phenyl | OCH$_2$ | 6-fluoroquinolin-2-yl | — | H, H | — | — | — |
| 248 | A29 | benzo[c][1,2,5]oxadiazol-5-yl | OCH$_2$ | 6-fluoroquinolin-2-yl | — | H, H | — | — | — |
| 249 | A29 | benzo[c][1,2,5]thiadiazol-5-yl | OCH$_2$ | 6-fluoroquinolin-2-yl | — | H, H | — | — | — |
| 250 | A29 | 3-chloro-4-(difluoromethoxy)phenyl | OCH$_2$ | 6-fluoroquinolin-2-yl | — | H, H | — | — | — |
| 251 | A29 | 3-cyano-4-(difluoromethoxy)phenyl | OCH$_2$ | 6-fluoroquinolin-2-yl | — | H, H | — | — | — |

-continued

| Ex. # | HET | X | Y | Z | R$_{1a}$, R$_{1b}$ | R$_2$ | R$_3$ | R$_4$ | R$_7$ |
|---|---|---|---|---|---|---|---|---|---|
| 252 | A29 | 1-tetrazolyl | | OCH$_2$ | 6-fluoroquinolin-2-yl | — | H, H | — | — | — |
| 253 | A29 | oxazol-5-yl | | OCH$_2$ | 6-fluoroquinolin-2-yl | — | H, H | — | — | — |
| 254 | A29 | oxazol-4-yl | | OCH$_2$ | 6-fluoroquinolin-2-yl | — | H, H | — | — | — |
| 255 | A29 | thiazol-5-yl | | OCH$_2$ | 6-fluoroquinolin-2-yl | — | H, H | — | — | — |
| 256 | A29 | thiazol-4-yl | | OCH$_2$ | 6-fluoroquinolin-2-yl | — | H, H | — | — | — |
| 257 | A29 | 5-(1H-tetrazolyl) | | OCH$_2$ | 6-fluoroquinolin-2-yl | — | H, H | — | — | — |
| 258 | A30 | pyrimidin-4-yl | | OCH$_2$ | 2-quinoline | — | H, H | — | — | H |
| 259 | A30 | 1,3,5-triazin-2-yl | | OCH$_2$ | 2-quinoline | — | H, H | — | — | H |
| 260 | A30 | pyridazin-4-yl | | OCH$_2$ | 2-quinoline | — | H, H | — | — | H |
| 261 | A30 | 2-hydroxypyridin-4-yl | | OCH$_2$ | 2-quinoline | — | H, H | — | — | H |

-continued

| Ex. # | HET | X | Y | Z | R1a, R1b | R2 | R3 | R4 | R7 |
|---|---|---|---|---|---|---|---|---|---|
| 262 | A30 | 2-MeO-pyridin-4-yl | OCH2 | 2-quinoline | — | H, H | — | — | H |
| 263 | A30 | 2-HO-pyridin-5-yl | OCH2 | 2-quinoline | — | H, H | — | — | H |
| 264 | A30 | 2-MeO-pyridin-5-yl | OCH2 | 2-quinoline | — | H, H | — | — | H |
| 265 | A30 | 4-MeO-3-F-phenyl | OCH2 | 2-quinoline | — | H, H | — | — | H |
| 266 | A30 | 4-MeO-3-Cl-phenyl | OCH2 | 2-quinoline | — | H, H | — | — | H |
| 267 | A30 | 4-MeO-3-Br-phenyl | OCH2 | 2-quinoline | — | H, H | — | — | H |
| 268 | A30 | 4-MeO-3-CN-phenyl | OCH2 | 2-quinoline | — | H, H | — | — | H |
| 269 | A30 | 4-MeO-phenyl | OCH2 | 2-quinoline | — | H, H | — | — | H |
| 270 | A30 | 4-NC-phenyl | OCH2 | 2-quinoline | — | H, H | — | — | H |

-continued

| Ex. # | HET | X | Y | Z | $R_{1a}, R_{1b}$ | $R_2$ | $R_3$ | $R_4$ | $R_7$ |
|---|---|---|---|---|---|---|---|---|---|
| 271 | A30 | 4-CN-3-F-phenyl | OCH₂ | 2-quinoline | — | H, H | — | — | H |
| 272 | A30 | 4-CN-3-Cl-phenyl | OCH₂ | 2-quinoline | — | H, H | — | — | H |
| 273 | A30 | 4-CN-3-Br-phenyl | OCH₂ | 2-quinoline | — | H, H | — | — | H |
| 274 | A30 | 4-CN-3-OMe-phenyl | OCH₂ | 2-quinoline | — | H, H | — | — | H |
| 275 | A30 | 3,4-di-CN-phenyl | OCH₂ | 2-quinoline | — | H, H | — | — | H |
| 276 | A30 | 4-Cl-phenyl | OCH₂ | 2-quinoline | — | H, H | — | — | H |
| 277 | A30 | 4-Cl-3-F-phenyl | OCH₂ | 2-quinoline | — | H, H | — | — | H |
| 278 | A30 | 3,4-di-Cl-phenyl | OCH₂ | 2-quinoline | — | H, H | — | — | H |

-continued

| Ex. # | HET | X | Y | Z | R₁ₐ, R₁ᵦ | R₂ | R₃ | R₄ | R₇ |
|---|---|---|---|---|---|---|---|---|---|
| 279 | A30 | 3-bromo-4-chlorophenyl | | OCH₂ 2-quinoline | — | H, H | — | — | H |
| 280 | A30 | 4-chloro-3-methoxyphenyl | | OCH₂ 2-quinoline | — | H, H | — | — | H |
| 281 | A30 | 4-chloro-3-cyanophenyl | | OCH₂ 2-quinoline | — | H, H | — | — | H |
| 282 | A30 | pyrimidin-4-yl | | OCH₂ 2-quinoline | — | H, H | — | — | Me |
| 283 | A30 | 1,3,5-triazin-2-yl | | OCH₂ 2-quinoline | — | H, H | — | — | Me |
| 284 | A30 | pyridazin-4-yl | | OCH₂ 2-quinoline | — | H, H | — | — | Me |
| 285 | A30 | 2-hydroxypyridin-4-yl | | OCH₂ 2-quinoline | — | H, H | — | — | Me |
| 286 | A30 | 2-methoxypyridin-4-yl | | OCH₂ 2-quinoline | — | H, H | — | — | Me |
| 287 | A30 | 2-hydroxypyridin-5-yl | | OCH₂ 2-quinoline | — | H, H | — | — | Me |

-continued
| Ex. # | HET | X | Y | Z | $R_{1a}, R_{1b}$ | $R_2$ | $R_3$ | $R_4$ | $R_7$ |
|---|---|---|---|---|---|---|---|---|---|
| 288 | A30 | 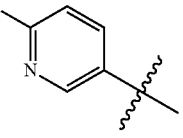 | $OCH_2$ | 2-quinoline | — | H, H | — | — | Me |
| 289 | A30 | 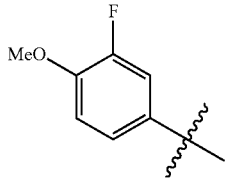 | $OCH_2$ | 2-quinoline | — | H, H | — | — | Me |
| 290 | A30 | 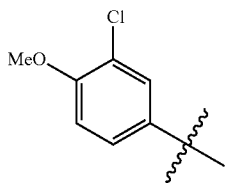 | $OCH_2$ | 2-quinoline | — | H, H | — | — | Me |
| 291 | A30 | 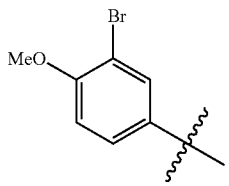 [SMILES: *c1ccc(OC)c(Br)c1] | $OCH_2$ | 2-quinoline | — | H, H | — | — | Me |
| 292 | A30 | 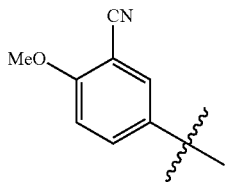 | $OCH_2$ | 2-quinoline | — | H, H | — | — | Me |
| 293 | A30 | 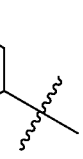 | $OCH_2$ | 2-quinoline | — | H, H | — | — | Me |
| 294 | A30 | 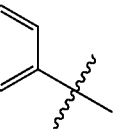 | $OCH_2$ | 2-quinoline | — | H, H | — | — | Me |
| 295 | A30 | 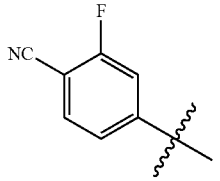 [SMILES: *c1ccc(C#N)c(F)c1] | $OCH_2$ | 2-quinoline | — | H, H | — | — | Me |
| 296 | A30 | 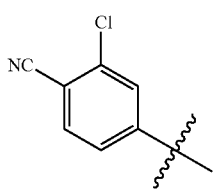 | $OCH_2$ | 2-quinoline | — | H, H | — | — | Me |

-continued

| Ex. # | HET | X | Y Z | $R_{1a}, R_{1b}$ | $R_2$ | $R_3$ | $R_4$ | $R_7$ |
|---|---|---|---|---|---|---|---|---|
| 297 | A30 | 2-Br, 4-(attach), NC (on ring) | OCH₂ 2-quinoline | — | H, H | — | — | Me |
| 298 | A30 | OMe, NC-phenyl | OCH₂ 2-quinoline | — | H, H | — | — | Me |
| 299 | A30 | CN, NC-phenyl | OCH₂ 2-quinoline | — | H, H | — | — | Me |
| 300 | A30 | Cl-phenyl | OCH₂ 2-quinoline | — | H, H | — | — | Me |
| 301 | A30 | F, Cl-phenyl | OCH₂ 2-quinoline | — | H, H | — | — | Me |
| 302 | A30 | Cl, Cl-phenyl | OCH₂ 2-quinoline | — | H, H | — | — | Me |
| 303 | A30 | Br, Cl-phenyl | OCH₂ 2-quinoline | — | H, H | — | — | Me |
| 304 | A30 | OMe, Cl-phenyl | OCH₂ 2-quinoline | — | H, H | — | — | Me |

-continued
| Ex. # | HET | X | Y | Z | R$_{1a}$, R$_{1b}$ | R$_2$ | R$_3$ | R$_4$ | R$_7$ |
|---|---|---|---|---|---|---|---|---|---|
| 305 | A30 | 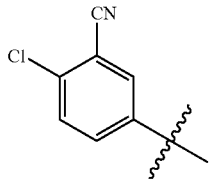 [SMILES: *c1ccc(Cl)c(C#N)c1] | OCH$_2$ | 2-quinoline | — | H, H | — | — | Me |
| 306 | A31 | 4-pyridinyl | OCH$_2$ | 2-quinoline | — | H, H | — | — | — |
| 307 | A31 | 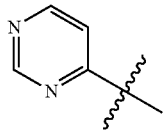 | OCH$_2$ | 2-quinoline | — | H, H | — | — | — |
| 308 | A31 | 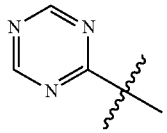 [SMILES: *c1ncncn1] | OCH$_2$ | 2-quinoline | — | H, H | — | — | — |
| 309 | A31 | 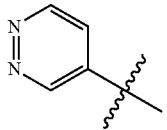 [SMILES: *c1ccnnc1] | OCH$_2$ | 2-quinoline | — | H, H | — | — | — |
| 310 | A31 | 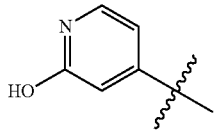 [SMILES: *c1ccnc(O)c1] | OCH$_2$ | 2-quinoline | — | H, H | — | — | — |
| 311 | A31 | 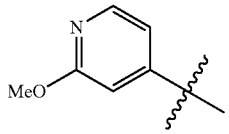 [SMILES: *c1ccnc(OC)c1] | OCH$_2$ | 2-quinoline | — | H, H | — | — | — |
| 312 | A31 | 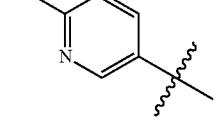 | OCH$_2$ | 2-quinoline | — | H, H | — | — | — |
| 313 | A31 | 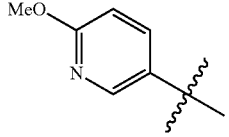 | OCH$_2$ | 2-quinoline | — | H, H | — | — | — |
| 314 | A31 | 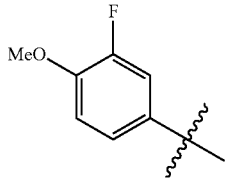 | OCH$_2$ | 2-quinoline | — | H, H | — | — | — |

| Ex. # | HET | X | Y Z | $R_{1a}, R_{1b}$ | $R_2$ | $R_3$ | $R_4$ | $R_7$ |
|---|---|---|---|---|---|---|---|---|
| 315 | A31 | 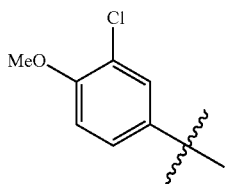 [SMILES: *c1ccc(OC)c(Cl)c1] | OCH$_2$ 2-quinoline | — | H, H | — | — | — |
| 316 | A31 | 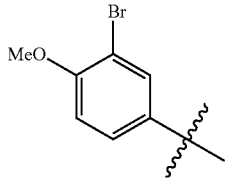 | OCH$_2$ 2-quinoline | — | H, H | — | — | — |
| 317 | A31 | 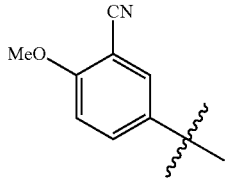 [SMILES: *c1ccc(OC)c(C#N)c1] | OCH$_2$ 2-quinoline | — | H, H | — | — | — |
| 318 | A31 | 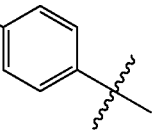 | OCH$_2$ 2-quinoline | — | H, H | — | — | — |
| 319 | A31 | 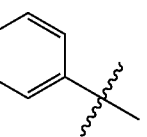 | OCH$_2$ 2-quinoline | — | H, H | — | — | — |
| 320 | A31 | 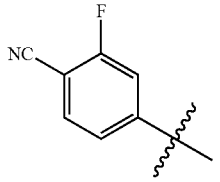 [SMILES: *c1ccc(C#N)c(F)c1] | OCH$_2$ 2-quinoline | — | H, H | — | — | — |
| 321 | A31 | 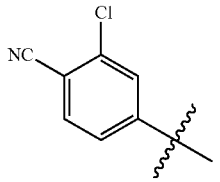 | OCH$_2$ 2-quinoline | — | H, H | — | — | — |
| 322 | A31 | 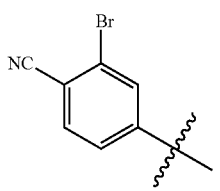 | OCH$_2$ 2-quinoline | — | H, H | — | — | — |

-continued

| Ex. # | HET | X | Y Z | R$_{1a}$, R$_{1b}$ | R$_2$ | R$_3$ | R$_4$ | R$_7$ |
|---|---|---|---|---|---|---|---|---|
| 323 | A31 | 4-CN-3-OMe-phenyl | OCH$_2$ 2-quinoline | — | H, H | — | — | — |
| 324 | A31 | 3-CN-4-CN-phenyl | OCH$_2$ 2-quinoline | — | H, H | — | — | — |
| 325 | A31 | 4-Cl-phenyl | OCH$_2$ 2-quinoline | — | H, H | — | — | — |
| 326 | A31 | 4-Cl-3-F-phenyl | OCH$_2$ 2-quinoline | — | H, H | — | — | — |
| 327 | A31 | 3,4-diCl-phenyl | OCH$_2$ 2-quinoline | — | H, H | — | — | — |
| 328 | A31 | 4-Cl-3-Br-phenyl | OCH$_2$ 2-quinoline | — | H, H | — | — | — |
| 329 | A31 | 4-Cl-3-OMe-phenyl | OCH$_2$ 2-quinoline | — | H, H | — | — | — |
| 330 | A31 | 4-Cl-3-CN-phenyl | OCH$_2$ 2-quinoline | — | H, H | — | — | — |

-continued

| Ex. # | HET | X | Y | Z | $R_{1a}, R_{1b}$ | $R_2$ | $R_3$ | $R_4$ | $R_7$ |
|---|---|---|---|---|---|---|---|---|---|
| 331 | A31 | 4-F-C6H4- | OCH2 | 2-quinoline | — | H, H | — | — | — |
| 332 | A31 | 4-F3C-C6H4- | OCH2 | 2-quinoline | — | H, H | — | — | — |
| 333 | A31 | 4-CF3O-C6H4- | OCH2 | 2-quinoline | — | H, H | — | — | — |
| 334 | A31 | 4-F3CH2C-C6H4- | OCH2 | 2-quinoline | — | H, H | — | — | — |
| 335 | A31 | 4-EtO-C6H4- | OCH2 | 2-quinoline | — | H, H | — | — | — |
| 336 | A31 | 4-iPrO-C6H4- | OCH2 | 2-quinoline | — | H, H | — | — | — |
| 337 | A31 | 4-F2CHO-C6H4- | OCH2 | 2-quinoline | — | H, H | — | — | — |
| 338 | A31 | 4-(cyclopropyl-O)-C6H4- | OCH2 | 2-quinoline | — | H, H | — | — | — |
| 339 | A31 | 4-(cyclopropyl-CH2O)-C6H4- | OCH2 | 2-quinoline | — | H, H | — | — | — |
| 340 | A31 | 4-(CF3CH2O)-C6H4- | OCH2 | 2-quinoline | — | H, H | — | — | — |

-continued

| Ex. # | HET | X | Y Z | R$_{1a}$, R$_{1b}$ | R$_2$ | R$_3$ | R$_4$ | R$_7$ |
|---|---|---|---|---|---|---|---|---|
| 341 | A31 | 4-Br-phenyl | OCH$_2$ 2-quinoline | — | H, H | — | — | — |
| 342 | A31 | 4-O$_2$N-phenyl | OCH$_2$ 2-quinoline | — | H, H | — | — | — |
| 343 | A31 | 4-(CHF$_2$)-phenyl | OCH$_2$ 2-quinoline | — | H, H | — | — | — |
| 344 | A31 | benzo[1,2,5]oxadiazolyl | OCH$_2$ 2-quinoline | — | H, H | — | — | — |
| 345 | A31 | benzo[1,2,5]thiadiazolyl | OCH$_2$ 2-quinoline | — | H, H | — | — | — |
| 346 | A31 | 2-(OCHF$_2$)-3-Cl-phenyl | OCH$_2$ 2-quinoline | — | H, H | — | — | — |
| 347 | A31 | 2-(OCHF$_2$)-5-CN-phenyl | OCH$_2$ 2-quinoline | — | H, H | — | — | — |
| 348 | A31 | tetrazol-1-yl | OCH$_2$ 2-quinoline | — | H, H | — | — | — |
| 349 | A31 | oxazol-5-yl | OCH$_2$ 2-quinoline | — | H, H | — | — | — |

-continued
| Ex. # | HET | X | Y | Z | R1a, R1b | R2 | R3 | R4 | R7 |
|---|---|---|---|---|---|---|---|---|---|
| 350 | A31 | 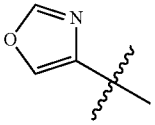 [SMILES: *c1cocn1] | OCH2 | 2-quinoline | — | H, H | — | — | — |
| 351 | A31 | 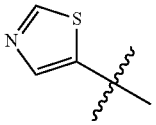 [SMILES: *c1cncs1] | OCH2 | 2-quinoline | — | H, H | — | — | — |
| 352 | A31 | 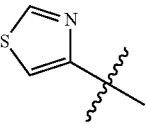 | OCH2 | 2-quinoline | — | H, H | — | — | — |
| 353 | A31 | 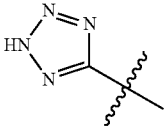 [SMILES: *c1nn[nH]n1] | OCH2 | 2-quinoline | — | H, H | — | — | — |
| 354 | A31 | 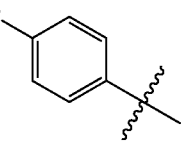 | OCH2 | 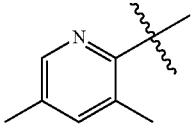 | — | H, H | — | — | — |
| 355 | A31 | 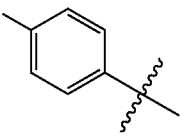 | OCH2 | 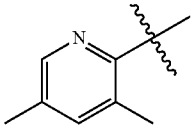 | — | H, H | — | — | — |
| 356 | A31 | 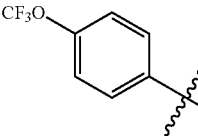 | OCH2 | 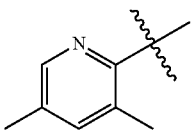 | — | H, H | — | — | — |
| 357 | A31 | 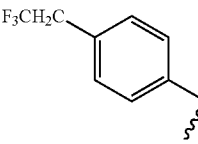 | OCH2 | 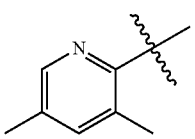 | — | H, H | — | — | — |
| 358 | A31 | 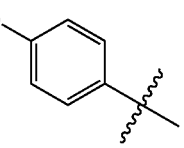 | OCH2 | 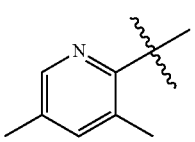 | — | H, H | — | — | — |
| 359 | A31 | 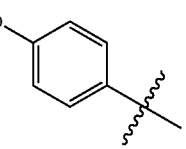 | OCH2 | 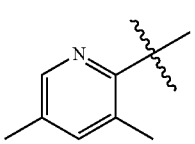 | — | H, H | — | — | — |

-continued

| Ex. # | HET | X | Y | Z | R₁ₐ, R₁ᵦ | R₂ | R₃ | R₄ | R₇ |
|---|---|---|---|---|---|---|---|---|---|
| 360 | A31 | 4-(CHF₂O)-phenyl | | OCH₂ | 3,5-dimethylpyridin-2-yl | — | H, H | — | — | — |
| 361 | A31 | 4-(cyclopropyl-O)-phenyl | | OCH₂ | 3,5-dimethylpyridin-2-yl | — | H, H | — | — | — |
| 362 | A31 | 4-(cyclopropyl-CH₂-O)-phenyl | | OCH₂ | 3,5-dimethylpyridin-2-yl | — | H, H | — | — | — |
| 363 | A31 | 4-(CF₃CH₂O)-phenyl | | OCH₂ | 3,5-dimethylpyridin-2-yl | — | H, H | — | — | — |
| 364 | A31 | 4-Br-phenyl | | OCH₂ | 3,5-dimethylpyridin-2-yl | — | H, H | — | — | — |
| 365 | A31 | 4-O₂N-phenyl | | OCH₂ | 3,5-dimethylpyridin-2-yl | — | H, H | — | — | — |
| 366 | A31 | 4-(CHF₂)-phenyl | | OCH₂ | 3,5-dimethylpyridin-2-yl | — | H, H | — | — | — |
| 367 | A31 | benzo[1,2,5]oxadiazol-5-yl | | OCH₂ | 3,5-dimethylpyridin-2-yl | — | H, H | — | — | — |
| 368 | A31 | benzo[1,2,5]thiadiazol-5-yl | | OCH₂ | 3,5-dimethylpyridin-2-yl | — | H, H | — | — | — |

-continued
| Ex. # | HET | X | Y | Z | R1a, R1b | R2 | R3 | R4 | R7 |
|---|---|---|---|---|---|---|---|---|---|
| 369 | A31 | 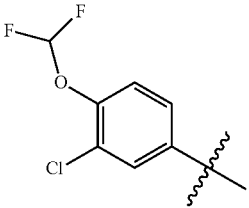 [SMILES: *c1ccc(OC(F)F)c(Cl)c1] | OCH2 | 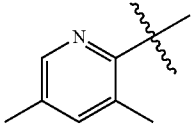 | — | H, H | — | — | — |
| 370 | A31 | 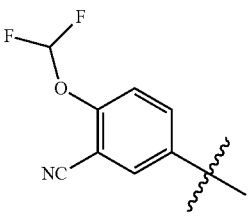 [SMILES: *c1ccc(OC(F)F)c(C#N)c1] | OCH2 | 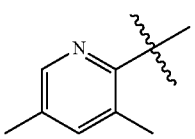 | — | H, H | — | — | — |
| 371 | A31 | 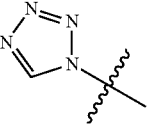 [SMILES: *n1cnnn1] | OCH2 | 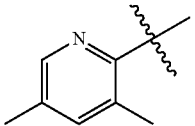 | — | H, H | — | — | — |
| 372 | A31 | 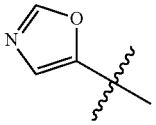 [SMILES: *c1cnco1] | OCH2 | 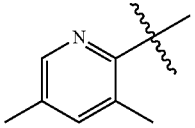 | — | H, H | — | — | — |
| 373 | A31 | 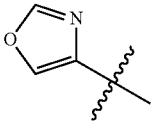 [SMILES: *c1cocn1] | OCH2 | 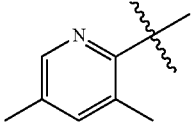 | — | H, H | — | — | — |
| 374 | A31 | 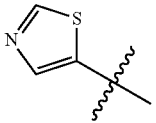 [SMILES: *c1cncs1] | OCH2 | 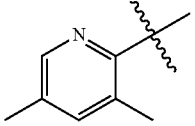 | — | H, H | — | — | — |
| 375 | A31 | 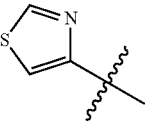 [SMILES: *c1cscn1] | OCH2 | 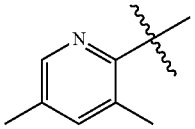 | — | H, H | — | — | — |
| 376 | A31 | 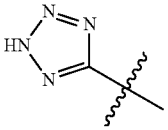 | OCH2 | 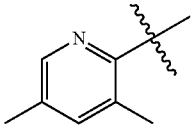 | — | H, H | — | — | — |
| 377 | A31 | 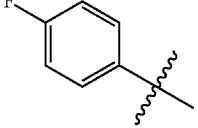 | OCH2 | 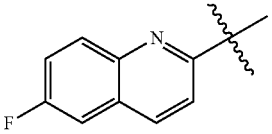 [SMILES: *c1ccc2cc(F)ccc2n1] | — | H, H | — | — | — |

-continued

| Ex. # | HET | X | Y | Z | R1a, R1b | R2 | R3 | R4 | R7 |
|---|---|---|---|---|---|---|---|---|---|
| 378 | A31 | F3C-C6H4- | | OCH2 | 6-F-quinolin-2-yl | — | H, H | — | — | — |
| 379 | A31 | CF3O-C6H4- | | OCH2 | 6-F-quinolin-2-yl | — | H, H | — | — | — |
| 380 | A31 | F3CH2C-C6H4- | | OCH2 | 6-F-quinolin-2-yl | — | H, H | — | — | — |
| 381 | A31 | EtO-C6H4- | | OCH2 | 6-F-quinolin-2-yl | — | H, H | — | — | — |
| 382 | A31 | iPrO-C6H4- | | OCH2 | 6-F-quinolin-2-yl | — | H, H | — | — | — |
| 383 | A31 | CHF2O-C6H4- | | OCH2 | 6-F-quinolin-2-yl | — | H, H | — | — | — |
| 384 | A31 | cyclopropyl-O-C6H4- | | OCH2 | 6-F-quinolin-2-yl | — | H, H | — | — | — |
| 385 | A31 | cyclopropyl-CH2-O-C6H4- | | OCH2 | 6-F-quinolin-2-yl | — | H, H | — | — | — |
| 386 | A31 | CF3CH2-O-C6H4- | | OCH2 | 6-F-quinolin-2-yl | — | H, H | — | — | — |
| 387 | A31 | Br-C6H4- | | OCH2 | 6-F-quinolin-2-yl | — | H, H | — | — | — |

| Ex. # | HET | X | Y | Z | R1a, R1b | R2 | R3 | R4 | R7 |
|---|---|---|---|---|---|---|---|---|---|
| 388 | A31 | 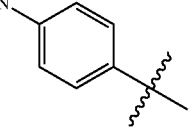 | | OCH₂ 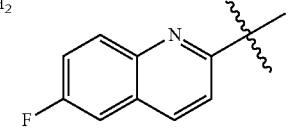 | — | H, H | — | — | — |
| 389 | A31 | 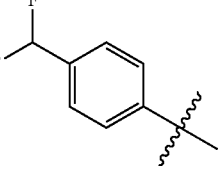 | | OCH₂ 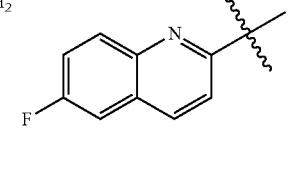 | — | H, H | — | — | — |
| 390 | A31 | 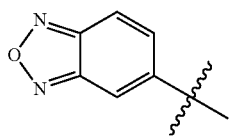 [SMILES: *c1ccc2nonc2c1] | | OCH₂ 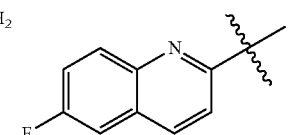 | — | H, H | — | — | — |
| 391 | A31 | 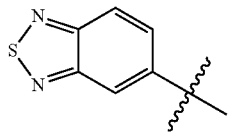 [SMILES: *c1ccc2nsnc2c1] | | OCH₂ 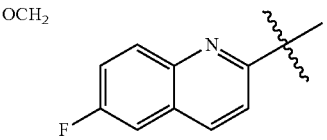 | — | H, H | — | — | — |
| 392 | A31 | 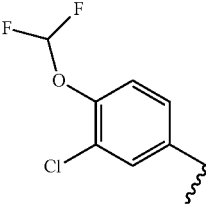 | | OCH₂ 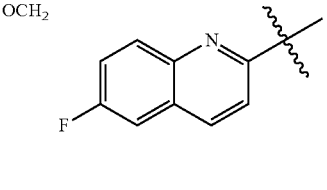 | — | H, H | — | — | — |
| 393 | A31 | 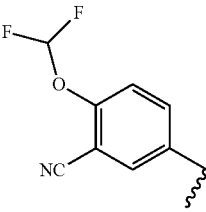 | | OCH₂ 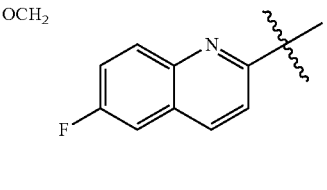 | — | H, H | — | — | — |
| 394 | A31 | 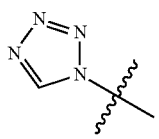 | | OCH₂ 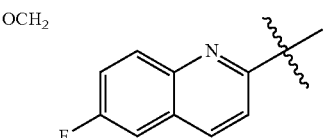 | — | H, H | — | — | — |
| 395 | A31 | 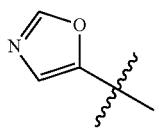 [SMILES: *c1cnco1] | | OCH₂ 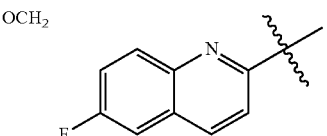 | — | H, H | — | — | — |
| 396 | A31 | 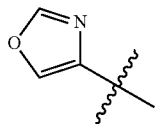 [SMILES: *c1cocn1] | | OCH₂ 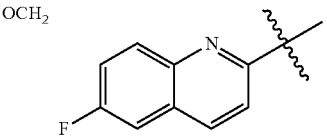 | — | H, H | — | — | — |

-continued
| Ex. # | HET | X | Y | Z | $R_{1a}, R_{1b}$ | $R_2$ | $R_3$ | $R_4$ | $R_7$ |
|---|---|---|---|---|---|---|---|---|---|
| 397 | A31 | 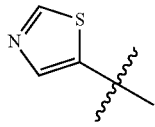 | OCH$_2$ | 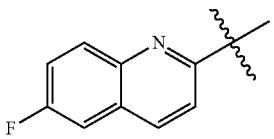 | — | H, H | — | — | — |
| 398 | A31 | 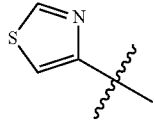 [SMILES: *c1cscn1] | OCH$_2$ | 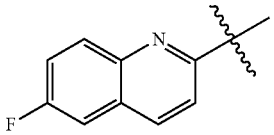 [SMILES: *c1ccc2cc(F)ccc2n1] | — | H, H | — | — | — |
| 399 | A31 | 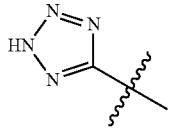 | OCH$_2$ | 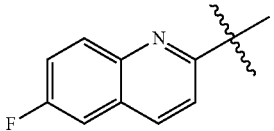 [SMILES: *c1ccc2cc(F)ccc2n1] | — | H, H | — | — | — |
| 400 | A31 | 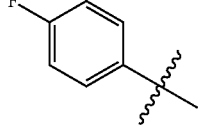 | OCH$_2$ | 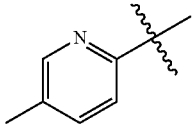 [SMILES: *c1ccc(C)cn1] | — | H, H | — | — | — |
| 401 | A31 | 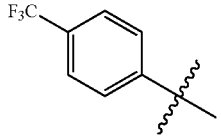 | OCH$_2$ | 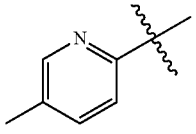 [SMILES: *c1ccc(C)cn1] | — | H, H | — | — | — |
| 402 | A31 | 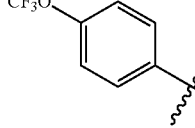 | OCH$_2$ | 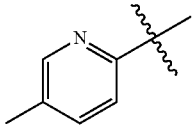 [SMILES: *c1ccc(C)cn1] | — | H, H | — | — | — |
| 403 | A31 | 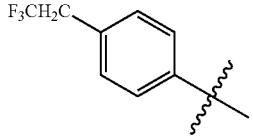 | OCH$_2$ | 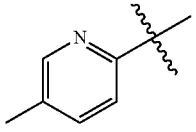 [SMILES: *c1ccc(C)cn1] | — | H, H | — | — | — |
| 404 | A31 | 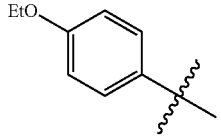 [SMILES: *c1ccc(OCC)cc1] | OCH$_2$ | 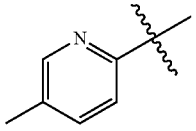 [SMILES: *c1ccc(C)cn1] | — | H, H | — | — | — |
| 405 | A31 | 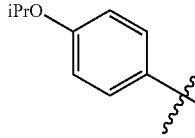 | OCH$_2$ | 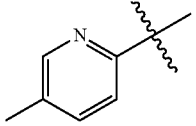 [SMILES: *c1ccc(C)cn1] | — | H, H | — | — | — |
| 406 | A31 | 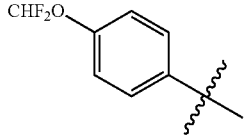 | OCH$_2$ | 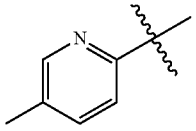 [SMILES: *c1ccc(C)cn1] | — | H, H | — | — | — |

-continued

| Ex. # | HET | X | Y | Z | $R_{1a}, R_{1b}$ | $R_2$ | $R_3$ | $R_4$ | $R_7$ |
|---|---|---|---|---|---|---|---|---|---|
| 407 | A31 | cyclopropyl-O-phenyl | OCH$_2$ | 5-methylpyridin-2-yl | — | H, H | — | — | — |
| 408 | A31 | cyclopropyl-CH$_2$-O-phenyl | OCH$_2$ | 5-methylpyridin-2-yl | — | H, H | — | — | — |
| 409 | A31 | CF$_2$H-CF$_2$-O-phenyl (2,2,2-trifluoroethoxyphenyl) | OCH$_2$ | 5-methylpyridin-2-yl | — | H, H | — | — | — |
| 410 | A31 | 4-bromophenyl | OCH$_2$ | 5-methylpyridin-2-yl | — | H, H | — | — | — |
| 411 | A31 | 4-nitrophenyl | OCH$_2$ | 5-methylpyridin-2-yl | — | H, H | — | — | — |
| 412 | A31 | 4-(difluoromethyl)phenyl | OCH$_2$ | 5-methylpyridin-2-yl | — | H, H | — | — | — |
| 413 | A31 | benzofurazan-5-yl | OCH$_2$ | 5-methylpyridin-2-yl | — | H, H | — | — | — |
| 414 | A31 | 2,1,3-benzothiadiazol-5-yl | OCH$_2$ | 5-methylpyridin-2-yl | — | H, H | — | — | — |
| 415 | A31 | 3-chloro-4-(difluoromethoxy)phenyl | OCH$_2$ | 5-methylpyridin-2-yl | — | H, H | — | — | — |

-continued
| Ex. # | HET | X | Y | Z | R$_{1a}$, R$_{1b}$ | R$_2$ | R$_3$ | R$_4$ | R$_7$ |
|---|---|---|---|---|---|---|---|---|---|
| 416 | A31 | 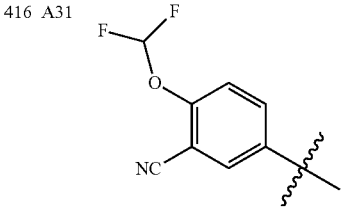 | OCH$_2$ | 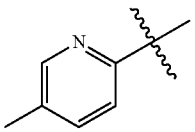 [SMILES: *c1ccc(C)cn1] | — | H, H | — | — | — |
| 417 | A31 | 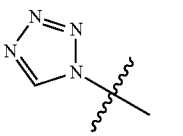 [SMILES: *n1cnnn1] | OCH$_2$ | 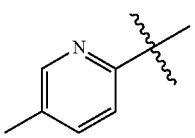 [SMILES: *c1ccc(C)cn1] | — | H, H | — | — | — |
| 418 | A31 | 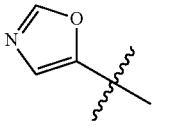 [SMILES: *c1cnco1] | OCH$_2$ | 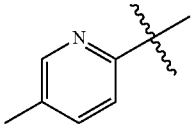 [SMILES: *c1ccc(C)cn1] | — | H, H | — | — | — |
| 419 | A31 | 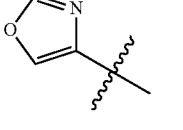 | OCH$_2$ | 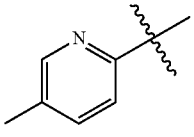 [SMILES: *c1ccc(C)cn1] | — | H, H | — | — | — |
| 420 | A31 | 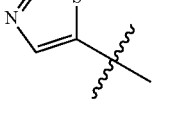 | OCH$_2$ | 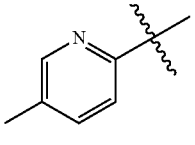 [SMILES: *c1ccc(C)cn1] | — | H, H | — | — | — |
| 421 | A31 | 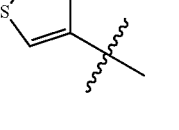 | OCH$_2$ | 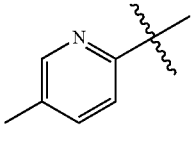 [SMILES: *c1ccc(C)cn1] | — | H, H | — | — | — |
| 422 | A31 | 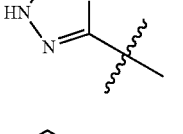 | OCH$_2$ | 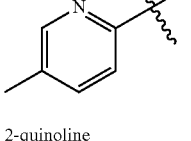 | — | H, H | — | — | — |
| 1085 | A7 | 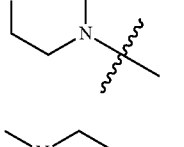 | OCH$_2$ | 2-quinoline | — | — | H | H | — |
| 1086 | A7 | 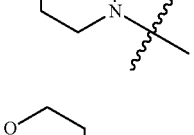 | OCH$_2$ | 2-quinoline | — | — | H | H | — |
| 1087 | A7 | 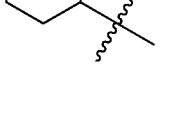 | OCH$_2$ | 2-quinoline | — | — | H | H | — |

-continued
| Ex. # | HET | X | Y | Z | $R_{1a}, R_{1b}$ | $R_2$ | $R_3$ | $R_4$ | $R_7$ |
|---|---|---|---|---|---|---|---|---|---|
| 1088 | A8 | 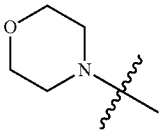 | OCH$_2$ | 2-quinoline | — | — | H | H | H |
| 1089 | A8 | 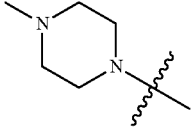 [SMILES: *N1CCN(C)CC1] | OCH$_2$ | 2-quinoline | — | — | H | H | H |
| 1090 | A8 | 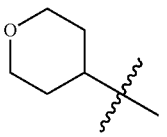 | OCH$_2$ | 2-quinoline | — | — | H | H | H |
| 1091 | A8 | 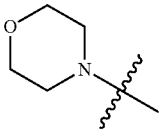 [SMILES: *N1CCOCC1] | OCH$_2$ | 2-quinoline | — | — | H | H | Me |
| 1092 | A8 | 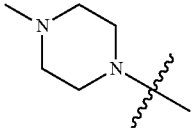 [SMILES: *N1CCN(C)CC1] | OCH$_2$ | 2-quinoline | — | — | H | H | Me |
| 1093 | A8 | 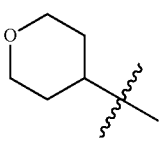 [SMILES: *C1CCOCC1] | OCH$_2$ | 2-quinoline | — | — | H | H | Me |
| 1094 | A16 | 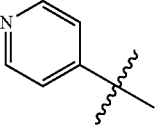 | OCH$_2$ | 2-quinoline | H | — | — | — | — |
| 1095 | A1 | 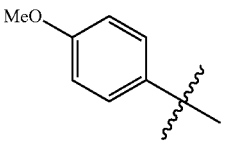 | OCH$_2$ | 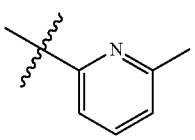 [SMILES: *c1cccc(C)n1] | — | — | H | H | — |
| 1096 | A18 | 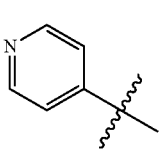 | OCH$_2$ | 2-quinoline | H, H | — | — | — | — |
| 1097 | A18 | 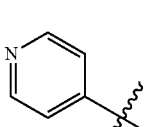 | OCH$_2$ | 2-quinoline | Me, H | — | — | — | — |

-continued

| Ex. # | HET | X | Y | Z | $R_{1a}, R_{1b}$ | $R_2$ | $R_3$ | $R_4$ | $R_7$ |
|---|---|---|---|---|---|---|---|---|---|
| 1098 | A7 | 3-pyridinyl | OCH$_2$ | 2-quinoline | — | — | H | H | — |
| 1100 | A13 | 4-pyridinyl | OCH$_2$ | 2-quinoline | Me, H | — | — | — | — |
| 1101 | A14 | 4-pyridinyl | OCH$_2$ | 2-quinoline | Me, H | — | — | — | — |

In a further aspect the compounds of the disclosure are embodied in with distinct examples listed in the table below taken from Formula (II):

| Ex. # | HET | W | X | Y | Z | $R_{1a}, R_{1b}$ | $R_2$ | $R_3$ | $R_4$ | $R_7$ |
|---|---|---|---|---|---|---|---|---|---|---|
| 423 | A1 | Cl | 4-pyridinyl | OCH$_2$ | 2-quinoline | — | — | H | H | — |
| 424 | A1 | Cl | 4-OMe-phenyl | OCH$_2$ | 2-quinoline | — | — | H | H | — |
| 425 | A1 | Cl | 4-pyrazolyl | OCH$_2$ | 2-quinoline | — | — | H | H | — |
| 426 | A1 | Cl | 3-(1-methyl-1H-pyrazolyl) | OCH$_2$ | 2-quinoline | — | — | H | H | — |
| 427 | A1 | Cl | 4-(1-methyl-1H-pyrazolyl) | OCH$_2$ | 2-quinoline | — | — | H | H | — |
| 428 | A1 | Cl | 4-pyrimidinyl | OCH$_2$ | 2-quinoline | — | — | H | H | — |
| 429 | A1 | Cl | 4-cyanophenyl | OCH$_2$ | 2-quinoline | — | — | H | H | — |
| 430 | A1 | Cl | 2-OMe-4-pyridinyl | OCH$_2$ | 2-quinoline | — | — | H | H | — |
| 431 | A1 | Cl | 6-OMe-3-pyridinyl | OCH$_2$ | 2-quinoline | — | — | H | H | — |
| 432 | A1 | Cl | 6-OH-3-pyridinyl | OCH$_2$ | 2-quinoline | — | — | H | H | — |
| 433 | A1 | Cl | 1,3,5-triazinyl | OCH$_2$ | 2-quinoline | — | — | H | H | — |

-continued

| Ex. # | HET | W | X | Y | Z | R₁ₐ, R₁ᵦ | R₂ | R₃ | R₄ | R₇ |
|---|---|---|---|---|---|---|---|---|---|---|
| 434 | A1 | Cl | 3-CN-4-OMe-phenyl | OCH₂ | 2-quinoline | — | — | H | H | — |
| 435 | A1 | Cl | 3-Cl-4-phenyl | OCH₂ | 2-quinoline | — | — | H | H | — |
| 436 | A2 | Cl | 4-pyridinyl | OCH₂ | 2-quinoline | — | — | H | H | H |
| 437 | A2 | Cl | 4-pyridinyl | OCH₂ | 2-quinoline | — | — | H | H | Me |
| 439 | A2 | Cl | 4-OMe-phenyl | OCH₂ | 2-quinoline | — | — | H | H | H |
| 440 | A2 | Cl | 4-OMe-phenyl | OCH₂ | 2-quinoline | — | — | H | H | Me |
| 442 | A2 | Cl | 4-pyrazolyl | OCH₂ | 2-quinoline | — | — | H | H | H |
| 443 | A2 | Cl | 4-pyrazolyl | OCH₂ | 2-quinoline | — | — | H | H | Me |
| 445 | A2 | Cl | 3-(1-methyl-1H-pyrazolyl) | OCH₂ | 2-quinoline | — | — | H | H | H |
| 446 | A2 | Cl | 3-(1-methyl-1H-pyrazolyl) | OCH₂ | 2-quinoline | — | — | H | H | Me |
| 448 | A2 | Cl | 4-(1-methyl-1H-pyrazolyl) | OCH₂ | 2-quinoline | — | — | H | H | H |
| 449 | A2 | Cl | 4-(1-methyl-1H-pyrazolyl) | OCH₂ | 2-quinoline | — | — | H | H | Me |
| 450 | A2 | Cl | 4-(1-methyl-1H-pyrazolyl) | OCH₂ | 2-quinoline | — | — | Me | Me | H |
| 451 | A2 | Cl | 4-pyrimidinyl | OCH₂ | 2-quinoline | — | — | H | H | H |
| 452 | A2 | Cl | 4-pyrimidinyl | OCH₂ | 2-quinoline | — | — | H | H | Me |
| 454 | A2 | Cl | 4-CN-phenyl | OCH₂ | 2-quinoline | — | — | H | H | H |
| 455 | A2 | Cl | 4-CN-phenyl | OCH₂ | 2-quinoline | — | — | H | H | Me |
| 457 | A2 | Cl | 2-OMe-4-pyridinyl | OCH₂ | 2-quinoline | — | — | H | H | H |
| 458 | A2 | Cl | 2-OMe-4-pyridinyl | OCH₂ | 2-quinoline | — | — | H | H | Me |

-continued
| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 460 | A2 | Cl | 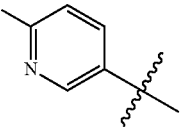 | OCH$_2$ | 2-quinoline | — | — | H | H | H |
| 461 | A2 | Cl | 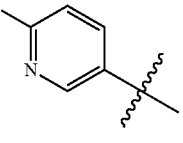 | OCH$_2$ | 2-quinoline | — | — | H | H | Me |
| 463 | A2 | Cl | 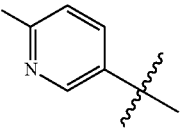 | OCH$_2$ | 2-quinoline | — | — | H | H | H |
| 464 | A2 | Cl | 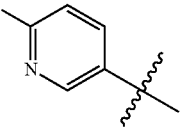 | OCH$_2$ | 2-quinoline | — | — | H | H | Me |
| 466 | A2 | Cl | 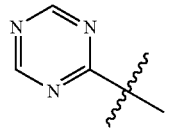 | OCH$_2$ | 2-quinoline | — | — | H | H | H |
| 467 | A2 | Cl | 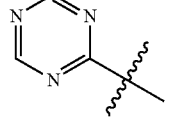 | OCH$_2$ | 2-quinoline | — | — | H | H | Me |
| 469 | A2 | Cl | 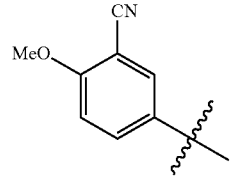 [SMILES: *c1ccc(OC)c(C#N)c1] | OCH$_2$ | 2-quinoline | — | — | H | H | H |
| 470 | A2 | Cl | 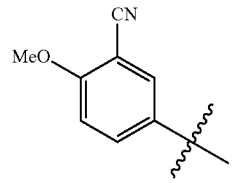 [SMILES: *c1ccc(OC)c(C#N)c1] | OCH$_2$ | 2-quinoline | — | — | H | H | Me |
| 472 | A2 | Cl | 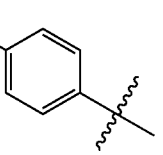 | OCH$_2$ | 2-quinoline | — | — | H | H | H |
| 473 | A2 | Cl | 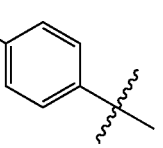 | OCH$_2$ | 2-quinoline | — | — | H | H | Me |

-continued

| Ex. # | HET | W | X | Y | Z | $R_{1a}, R_{1b}$ | $R_2$ | $R_3$ | $R_4$ | $R_7$ |
|---|---|---|---|---|---|---|---|---|---|---|
| 475 | A6 | Cl | 4-pyridinyl | OCH$_2$ | 2-quinoline | H, — | — | — | — | H |
| 476 | A6 | Cl | 4-OMe-phenyl | OCH$_2$ | 2-quinoline | H, — | — | — | — | H |
| 477 | A6 | Cl | 4-pyrazolyl | OCH$_2$ | 2-quinoline | H, — | — | — | — | H |
| 478 | A6 | Cl | 3-(1-methyl-1H-pyrazolyl) | OCH$_2$ | 2-quinoline | H, — | — | — | — | H |
| 479 | A6 | Cl | 4-(1-methyl-1H-pyrazolyl) | OCH$_2$ | 2-quinoline | H, — | — | — | — | H |
| 480 | A6 | Cl | 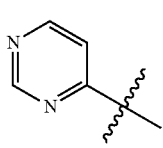 | OCH$_2$ | 2-quinoline | H, — | — | — | — | H |
| 481 | A6 | Cl | 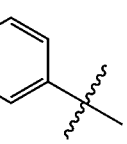 | OCH$_2$ | 2-quinoline | H, — | — | — | — | H |
| 482 | A6 | Cl | 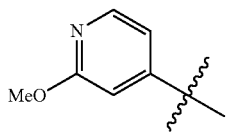 | OCH$_2$ | 2-quinoline | H, — | — | — | — | H |
| 483 | A6 | Cl | 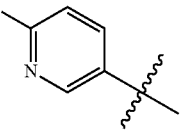 | OCH$_2$ | 2-quinoline | H, — | — | — | — | H |
| 484 | A6 | Cl | 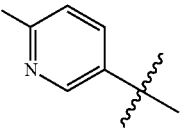 | OCH$_2$ | 2-quinoline | H, — | — | — | — | H |
| 485 | A6 | Cl | 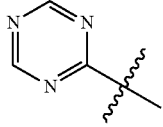 [SMILES: *c1ncncn1] | OCH$_2$ | 2-quinoline | H, — | — | — | — | H |
| 486 | A6 | Cl | 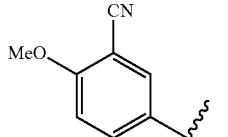 | OCH$_2$ | 2-quinoline | H, — | — | — | — | H |
| 487 | A6 | Cl | 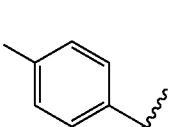 | OCH$_2$ | 2-quinoline | H, — | — | — | — | H |
| 488 | A11 | Cl | 4-pyridinyl | OCH$_2$ | 2-quinoline | H, — | — | — | — | — |
| 489 | A11 | Cl | 4-OMe-phenyl | OCH$_2$ | 2-quinoline | H, — | — | — | — | — |
| 490 | A11 | Cl | 4-pyrazolyl | OCH$_2$ | 2-quinoline | H, — | — | — | — | — |
| 491 | A11 | Cl | 3-(1-methyl-1H-pyrazolyl) | OCH$_2$ | 2-quinoline | H, — | — | — | — | — |
| 492 | A11 | Cl | 4-(1-methyl-1H-pyrazolyl) | OCH$_2$ | 2-quinoline | H, — | — | — | — | — |

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 493 | A11 | Cl | 4-pyrimidinyl | OCH$_2$ | 2-quinoline | H, — | — | — | — | — |
| 494 | A11 | Cl | 4-NC-phenyl | OCH$_2$ | 2-quinoline | H, — | — | — | — | — |
| 495 | A11 | Cl | 2-MeO-4-pyridinyl | OCH$_2$ | 2-quinoline | H, — | — | — | — | — |
| 496 | A11 | Cl | 6-MeO-3-pyridinyl | OCH$_2$ | 2-quinoline | H, — | — | — | — | — |
| 497 | A11 | Cl | 6-HO-3-pyridinyl | OCH$_2$ | 2-quinoline | H, — | — | — | — | — |
| 498 | A11 | Cl | 1,3,5-triazin-2-yl | OCH$_2$ | 2-quinoline | H, — | — | — | — | — |
| 499 | A11 | Cl | 4-MeO-3-CN-phenyl | OCH$_2$ | 2-quinoline | H, — | — | — | — | — |
| 500 | A11 | Cl | 4-Cl-phenyl | OCH$_2$ | 2-quinoline | H, — | — | — | — | — |
| 501 | A12 | Cl | 4-pyridinyl | OCH$_2$ | 2-quinoline | H, — | — | — | — | — |
| 502 | A12 | Cl | 4-OMe-phenyl | OCH$_2$ | 2-quinoline | H, — | — | — | — | — |
| 503 | A12 | Cl | 4-pyrazolyl | OCH$_2$ | 2-quinoline | H, — | — | — | — | — |
| 504 | A12 | Cl | 3-(1-methyl-1H-pyrazolyl) | OCH$_2$ | 2-quinoline | H, — | — | — | — | — |
| 505 | A12 | Cl | 4-(1-methyl-1H-pyrazolyl) | OCH$_2$ | 2-quinoline | H, — | — | — | — | — |
| 506 | A12 | Cl | 4-pyrimidinyl | OCH$_2$ | 2-quinoline | H, — | — | — | — | — |

-continued

| Ex. # | HET | W | X | Y | Z | $R_{1a}, R_{1b}$ | $R_2$ | $R_3$ | $R_4$ | $R_7$ |
|---|---|---|---|---|---|---|---|---|---|---|
| 507 | A12 | Cl | 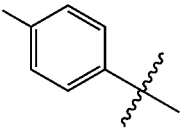 | $OCH_2$ | 2-quinoline | H, — | — | — | — | — |
| 508 | A12 | Cl | 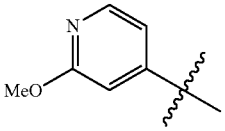 | $OCH_2$ | 2-quinoline | H, — | — | — | — | — |
| 509 | A12 | Cl | 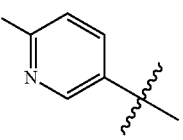 | $OCH_2$ | 2-quinoline | H, — | — | — | — | — |
| 510 | A12 | Cl | 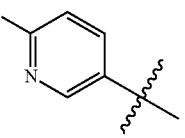 | $OCH_2$ | 2-quinoline | H, — | — | — | — | — |
| 511 | A12 | Cl | 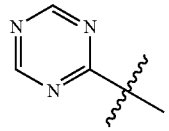 | $OCH_2$ | 2-quinoline | H, — | — | — | — | — |
| 512 | A12 | Cl | 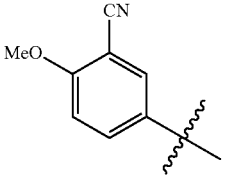 [SMILES: *c1ccc(OC)c(C#N)c1] | $OCH_2$ | 2-quinoline | H, — | — | — | — | — |
| 513 | A12 | Cl | 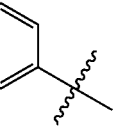 | $OCH_2$ | 2-quinoline | H, — | — | — | — | — |
| 514 | A13 | Cl | 4-pyridinyl | $OCH_2$ | 2-quinoline | H, H | — | — | — | — |
| 515 | A13 | Cl | 4-OMe-phenyl | $OCH_2$ | 2-quinoline | H, H | — | — | — | — |
| 516 | A13 | Cl | 4-pyrazolyl | $OCH_2$ | 2-quinoline | H, H | — | — | — | — |
| 517 | A13 | Cl | 3-(1-methyl-1H-pyrazolyl) | $OCH_2$ | 2-quinoline | H, H | — | — | — | — |
| 518 | A13 | Cl | 4-(1-methyl-1H-pyrazolyl) | $OCH_2$ | 2-quinoline | H, H | — | — | — | — |
| 519 | A13 | Cl | 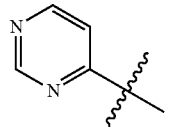 | $OCH_2$ | 2-quinoline | H, H | — | — | — | — |
| 520 | A13 | Cl | 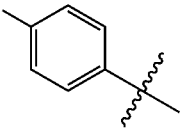 | $OCH_2$ | 2-quinoline | H, H | — | — | — | — |

-continued

| Ex. # | HET | W | X | Y | Z | $R_{1a}, R_{1b}$ | $R_2$ | $R_3$ | $R_4$ | $R_7$ |
|---|---|---|---|---|---|---|---|---|---|---|
| 521 | A13 | Cl | 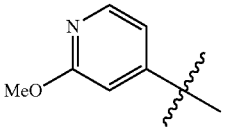 [SMILES: *c1ccnc(OC)c1] | OCH$_2$ | 2-quinoline | H, H | — | — | — | — |
| 522 | A13 | Cl | 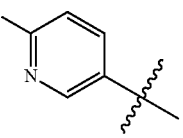 | OCH$_2$ | 2-quinoline | H, H | — | — | — | — |
| 523 | A13 | Cl | 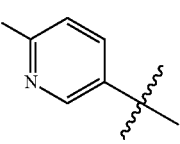 | OCH$_2$ | 2-quinoline | H, H | — | — | — | — |
| 524 | A13 | Cl | 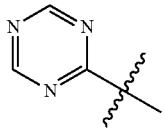 | OCH$_2$ | 2-quinoline | H, H | — | — | — | — |
| 525 | A13 | Cl | 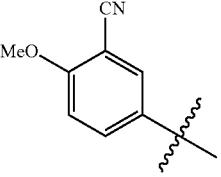 [SMILES: *c1ccc(OC)c(C#N)c1] | OCH$_2$ | 2-quinoline | H, H | — | — | — | — |
| 526 | A13 | Cl | 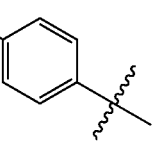 | OCH$_2$ | 2-quinoline | H, H | — | — | — | — |
| 527 | A14 | Cl | 4-pyridinyl | OCH$_2$ | 2-quinoline | H, H | — | — | — | — |
| 528 | A14 | Cl | 4-OMe-phenyl | OCH$_2$ | 2-quinoline | H, H | — | — | — | — |
| 529 | A14 | Cl | 4-pyrazolyl | OCH$_2$ | 2-quinoline | H, H | — | — | — | — |
| 530 | A14 | Cl | 3-(1-methyl-1H-pyrazolyl) | OCH$_2$ | 2-quinoline | H, H | — | — | — | — |
| 531 | A14 | Cl | 4-(1-methyl-1H-pyrazolyl) | OCH$_2$ | 2-quinoline | H, H | — | — | — | — |
| 532 | A14 | Cl | 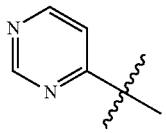 | OCH$_2$ | 2-quinoline | H, H | — | — | — | — |
| 533 | A14 | Cl | 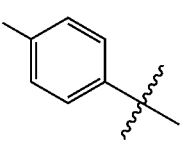 | OCH$_2$ | 2-quinoline | H, H | — | — | — | — |
| 534 | A14 | Cl | 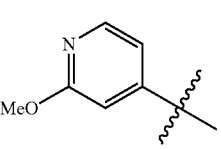 [SMILES: *c1ccnc(OC)c1] | OCH$_2$ | 2-quinoline | H, H | — | — | — | — |

-continued

| Ex. # | HET | W | X | Y | Z | R1a, R1b | R2 | R3 | R4 | R7 |
|---|---|---|---|---|---|---|---|---|---|---|
| 535 | A14 | Cl | 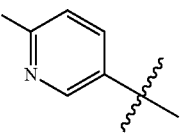 | OCH2 | 2-quinoline | H, H | — | — | — | — |
| 536 | A14 | Cl | 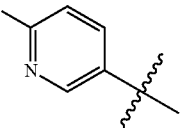 | OCH2 | 2-quinoline | H, H | — | — | — | — |
| 537 | A14 | Cl | 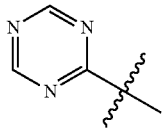 [SMILES: *c1ncncn1] | OCH2 | 2-quinoline | H, H | — | — | — | — |
| 538 | A14 | Cl | 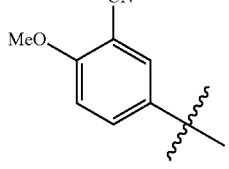 | OCH2 | 2-quinoline | H, H | — | — | — | — |
| 539 | A14 | Cl | 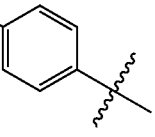 | OCH2 | 2-quinoline | H, H | — | — | — | — |
| 540 | A15 | Cl | 4-pyridinyl | OCH2 | 2-quinoline | H, H | — | — | — | — |
| 541 | A15 | Cl | 4-OMe-phenyl | OCH2 | 2-quinoline | H, H | — | — | — | — |
| 542 | A15 | Cl | 4-pyrazolyl | OCH2 | 2-quinoline | H, H | — | — | — | — |
| 543 | A15 | Cl | 3-(1-methyl-1H-pyrazolyl) | OCH2 | 2-quinoline | H, H | — | — | — | — |
| 544 | A15 | Cl | 4-(1-methyl-1H-pyrazolyl) | OCH2 | 2-quinoline | H, H | — | — | — | — |
| 545 | A15 | Cl | 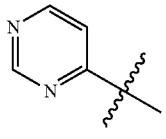 | OCH2 | 2-quinoline | H, H | — | — | — | — |
| 546 | A15 | Cl | 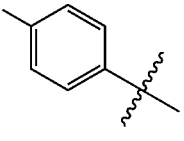 | OCH2 | 2-quinoline | H, H | — | — | — | — |
| 547 | A15 | Cl | 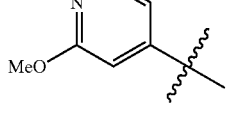 | OCH2 | 2-quinoline | H, H | — | — | — | — |
| 548 | A15 | Cl | 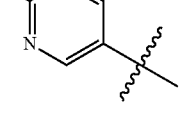 | OCH2 | 2-quinoline | H, H | — | — | — | — |

-continued

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 549 | A15 | Cl | 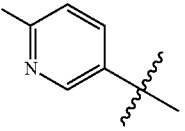 | OCH$_2$ | 2-quinoline | H, H | — | — | — | — |
| 550 | A15 | Cl | 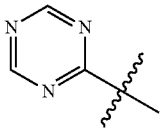 | OCH$_2$ | 2-quinoline | H, H | — | — | — | — |
| 551 | A15 | Cl | 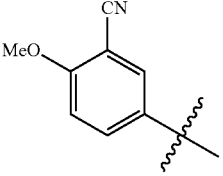 [SMILES: *c1ccc(OC)c(C#N)c1] | OCH$_2$ | 2-quinoline | H, H | — | — | — | — |
| 552 | A15 | Cl | 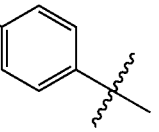 | OCH$_2$ | 2-quinoline | H, H | — | — | — | — |
| 553 | A19 | Cl | 4-pyridinyl | OCH$_2$ | 2-quinoline | H, — | — | — | — | — |
| 554 | A19 | Cl | 4-OMe-phenyl | OCH$_2$ | 2-quinoline | H, — | — | — | — | — |
| 555 | A19 | Cl | 4-pyrazolyl | OCH$_2$ | 2-quinoline | H, — | — | — | — | — |
| 556 | A19 | Cl | 3-(1-methyl-1H-pyrazolyl) | OCH$_2$ | 2-quinoline | H, — | — | — | — | — |
| 557 | A19 | Cl | 4-(1-methyl-1H-pyrazolyl) | OCH$_2$ | 2-quinoline | H, — | — | — | — | — |
| 558 | A19 | Cl | 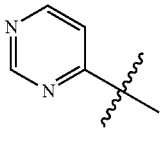 | OCH$_2$ | 2-quinoline | H, — | — | — | — | — |
| 559 | A19 | Cl | 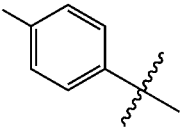 | OCH$_2$ | 2-quinoline | H, — | — | — | — | — |
| 560 | A19 | Cl | 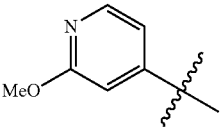 [SMILES: *c1ccnc(OC)c1] | OCH$_2$ | 2-quinoline | H, — | — | — | — | — |
| 561 | A19 | Cl | 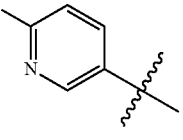 | OCH$_2$ | 2-quinoline | H, — | — | — | — | — |
| 562 | A19 | Cl | 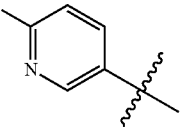 | OCH$_2$ | 2-quinoline | H, — | — | — | — | — |

-continued

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 563 | A19 | Cl | 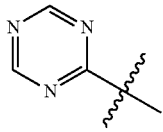 | OCH$_2$ | 2-quinoline | H, — | — | — | — | — |
| 564 | A19 | Cl | 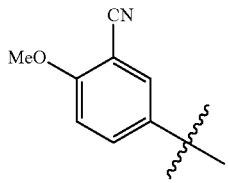 [SMILES: *c1ccc(OC)c(C#N)c1] | OCH$_2$ | 2-quinoline | H, — | — | — | — | — |
| 565 | A19 | Cl | 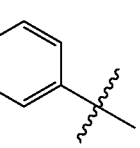 | OCH$_2$ | 2-quinoline | H, — | — | — | — | — |
| 566 | A20 | Cl | 4-pyridinyl | OCH$_2$ | 2-quinoline | H, H | — | — | — | — |
| 567 | A20 | Cl | 4-OMe-phenyl | OCH$_2$ | 2-quinoline | H, H | — | — | — | — |
| 568 | A20 | Cl | 4-pyrazolyl | OCH$_2$ | 2-quinoline | H, H | — | — | — | — |
| 569 | A20 | Cl | 3-(1-methyl-1H-pyrazolyl) | OCH$_2$ | 2-quinoline | H, H | — | — | — | — |
| 570 | A20 | Cl | 4-(1-methyl-1H-pyrazolyl) | OCH$_2$ | 2-quinoline | H, H | — | — | — | — |
| 571 | A20 | Cl | 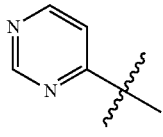 | OCH$_2$ | 2-quinoline | H, H | — | — | — | — |
| 572 | A20 | Cl | 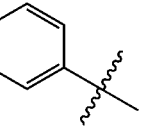 | OCH$_2$ | 2-quinoline | H, H | — | — | — | — |
| 573 | A20 | Cl | 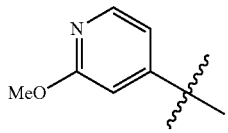 | OCH$_2$ | 2-quinoline | H, H | — | — | — | — |
| 574 | A20 | Cl | 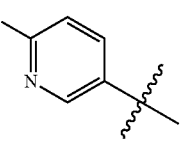 | OCH$_2$ | 2-quinoline | H, H | — | — | — | — |
| 575 | A20 | Cl | 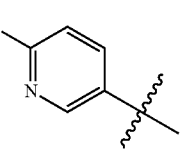 | OCH$_2$ | 2-quinoline | H, H | — | — | — | — |
| 576 | A20 | Cl | 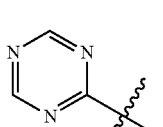 | OCH$_2$ | 2-quinoline | H, H | — | — | — | — |

-continued

| Ex. # | HET | W | X | Y | Z | R_{1a}, R_{1b} | R_2 | R_3 | R_4 | R_7 |
|---|---|---|---|---|---|---|---|---|---|---|
| 577 | A20 | Cl | 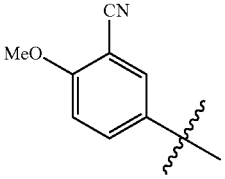 [SMILES: *c1ccc(OC)c(C#N)c1] | OCH_2 | 2-quinoline | H, H | — | — | — | — |
| 578 | A20 | Cl | 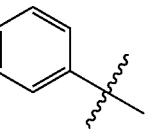 | OCH_2 | 2-quinoline | H, H | — | — | — | — |
| 579 | A32 | Cl | 4-pyridinyl | OCH_2 | 2-quinoline | — | H, H | — | — | H |
| 580 | A32 | Cl | 4-OMe-phenyl | OCH_2 | 2-quinoline | — | H, H | — | — | H |
| 581 | A32 | Cl | 4-pyrazolyl | OCH_2 | 2-quinoline | — | H, H | — | — | H |
| 582 | A32 | Cl | 3-(1-methyl-1H-pyrazolyl) | OCH_2 | 2-quinoline | — | H, H | — | — | H |
| 583 | A32 | Cl | 4-(1-methyl-1H-pyrazolyl) | OCH_2 | 2-quinoline | — | H, H | — | — | H |
| 584 | A32 | Cl | 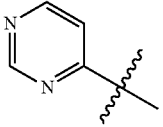 | OCH_2 | 2-quinoline | — | H, H | — | — | H |
| 585 | A1 | CN | 4-pyridinyl | OCH_2 | 2-quinoline | — | — | H | H | — |
| 586 | A1 | CN | 4-OMe-phenyl | OCH_2 | 2-quinoline | — | — | H | H | — |
| 587 | A1 | CN | 4-pyrazolyl | OCH_2 | 2-quinoline | — | — | H | H | — |
| 588 | A1 | CN | 3-(1-methyl-1H-pyrazolyl) | OCH_2 | 2-quinoline | — | — | H | H | — |
| 589 | A1 | CN | 4-(1-methyl-1H-pyrazolyl) | OCH_2 | 2-quinoline | — | — | H | H | — |
| 590 | A1 | CN | 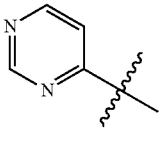 | OCH_2 | 2-quinoline | — | — | H | H | — |
| 591 | A1 | CN | 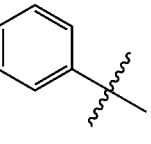 | OCH_2 | 2-quinoline | — | — | H | H | — |
| 592 | A1 | CN | 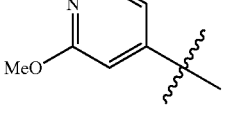 | OCH_2 | 2-quinoline | — | — | H | H | — |
| 593 | A1 | CN | 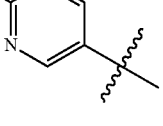 | OCH_2 | 2-quinoline | — | — | H | H | — |
| 594 | A1 | CN | 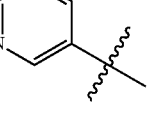 | OCH_2 | 2-quinoline | — | — | H | H | — |

-continued

| Ex. # | HET | W | X | Y | Z | R1a, R1b | R2 | R3 | R4 | R7 |
|---|---|---|---|---|---|---|---|---|---|---|
| 595 | A1 | CN | 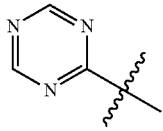 | OCH2 | 2-quinoline | — | — | H | H | — |
| 596 | A1 | CN | 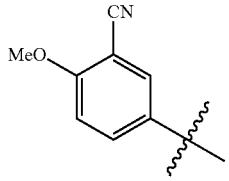 [SMILES: *c1ccc(OC)c(C#N)c1] | OCH2 | 2-quinoline | — | — | H | H | — |
| 597 | A1 | CN | 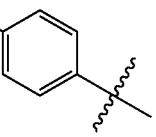 | OCH2 | 2-quinoline | — | — | H | H | — |
| 598 | A2 | CN | 4-pyridinyl | OCH2 | 2-quinoline | — | — | H | H | H |
| 599 | A2 | CN | 4-pyridinyl | OCH2 | 2-quinoline | — | — | H | H | Me |
| 601 | A2 | CN | 4-OMe-phenyl | OCH2 | 2-quinoline | — | — | H | H | H |
| 602 | A2 | CN | 4-OMe-phenyl | OCH2 | 2-quinoline | — | — | H | H | Me |
| 604 | A2 | CN | 4-pyrazolyl | OCH2 | 2-quinoline | — | — | H | H | H |
| 605 | A2 | CN | 4-pyrazolyl | OCH2 | 2-quinoline | — | — | H | H | Me |
| 607 | A2 | CN | 3-(1-methyl-1H-pyrazolyl) | OCH2 | 2-quinoline | — | — | H | H | H |
| 608 | A2 | CN | 3-(1-methyl-1H-pyrazolyl) | OCH2 | 2-quinoline | — | — | H | H | Me |
| 610 | A2 | CN | 4-(1-methyl-1H-pyrazolyl) | OCH2 | 2-quinoline | — | — | H | H | H |
| 611 | A2 | CN | 4-(1-methyl-1H-pyrazolyl) | OCH2 | 2-quinoline | — | — | H | H | Me |
| 613 | A2 | CN | 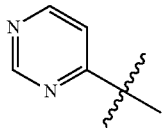 | OCH2 | 2-quinoline | — | — | H | H | H |
| 614 | A2 | CN | 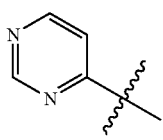 | OCH2 | 2-quinoline | — | — | H | H | Me |
| 616 | A2 | CN | 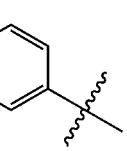 | OCH2 | 2-quinoline | — | — | H | H | H |
| 617 | A2 | CN | 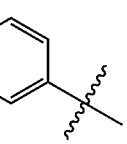 | OCH2 | 2-quinoline | — | — | H | H | Me |
| 619 | A2 | CN | 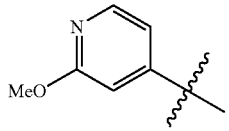 [SMILES: *c1ccnc(OC)c1] | OCH2 | 2-quinoline | — | — | H | H | H |
| 620 | A2 | CN | 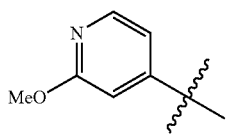 [SMILES: *c1ccnc(OC)c1] | OCH2 | 2-quinoline | — | — | H | H | Me |

-continued
| Ex. # | HET | W | X | Y | Z | $R_{1a}, R_{1b}$ | $R_2$ | $R_3$ | $R_4$ | $R_7$ |
|---|---|---|---|---|---|---|---|---|---|---|
| 622 | A2 | CN | 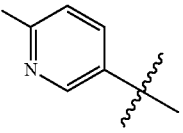 | OCH$_2$ | 2-quinoline | — | — | H | H | H |
| 623 | A2 | CN | 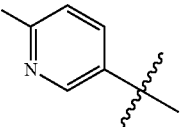 | OCH$_2$ | 2-quinoline | — | — | H | H | Me |
| 625 | A2 | CN | 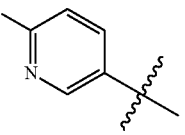 | OCH$_2$ | 2-quinoline | — | — | H | H | H |
| 626 | A2 | CN | 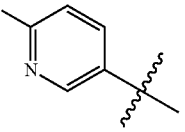 | OCH$_2$ | 2-quinoline | — | — | H | H | Me |
| 628 | A2 | CN | 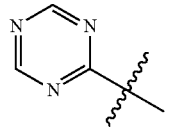 [SMILES: *c1ncncn1] | OCH$_2$ | 2-quinoline | — | — | H | H | H |
| 629 | A2 | CN | 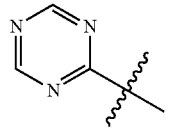 [SMILES: *c1ncncn1] | OCH$_2$ | 2-quinoline | — | — | H | H | Me |
| 631 | A2 | CN | 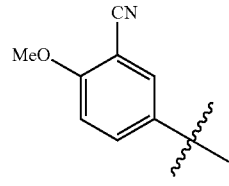 [SMILES: *c1ccc(OC)c(C#N)c1] | OCH$_2$ | 2-quinoline | — | — | H | H | H |
| 632 | A2 | CN | 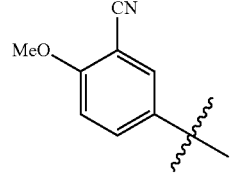 [SMILES: *c1ccc(OC)c(C#N)c1] | OCH$_2$ | 2-quinoline | — | — | H | H | Me |
| 634 | A2 | CN | 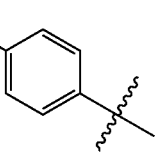 | OCH$_2$ | 2-quinoline | — | — | H | H | H |
| 635 | A2 | CN | 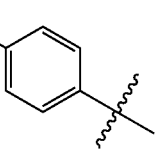 | OCH$_2$ | 2-quinoline | — | — | H | H | Me |

-continued

| Ex. # | HET | W | X | Y | Z | $R_{1a}, R_{1b}$ | $R_2$ | $R_3$ | $R_4$ | $R_7$ |
|---|---|---|---|---|---|---|---|---|---|---|
| 637 | A6 | CN | 4-pyridinyl | OCH$_2$ | 2-quinoline | H, — | — | — | — | H |
| 638 | A6 | CN | 4-OMe-phenyl | OCH$_2$ | 2-quinoline | H, — | — | — | — | H |
| 639 | A6 | CN | 4-pyrazolyl | OCH$_2$ | 2-quinoline | H, — | — | — | — | H |
| 640 | A6 | CN | 3-(1-methyl-1H-pyrazolyl) | OCH$_2$ | 2-quinoline | H, — | — | — | — | H |
| 641 | A6 | CN | 4-(1-methyl-1H-pyrazolyl) | OCH$_2$ | 2-quinoline | H, — | — | — | — | H |
| 642 | A6 | CN | 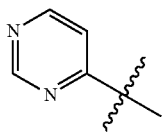 | OCH$_2$ | 2-quinoline | H, — | — | — | — | H |
| 643 | A6 | CN | 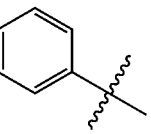 | OCH$_2$ | 2-quinoline | H, — | — | — | — | H |
| 644 | A6 | CN | 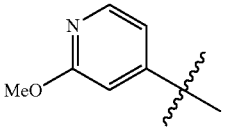 | OCH$_2$ | 2-quinoline | H, — | — | — | — | H |
| 645 | A6 | CN | 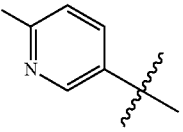 | OCH$_2$ | 2-quinoline | H, — | — | — | — | H |
| 646 | A6 | CN | 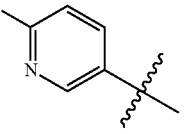 | OCH$_2$ | 2-quinoline | H, — | — | — | — | H |
| 647 | A6 | CN | 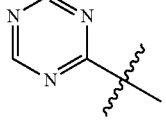 | OCH$_2$ | 2-quinoline | H, — | — | — | — | H |
| 648 | A6 | CN | 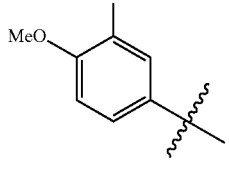 | OCH$_2$ | 2-quinoline | H, — | — | — | — | H |
| 649 | A6 | CN | 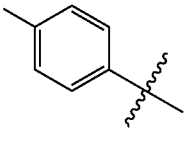 | OCH$_2$ | 2-quinoline | H, — | — | — | — | H |
| 650 | A11 | CN | 4-pyridinyl | OCH$_2$ | 2-quinoline | H, — | — | — | — | — |
| 651 | A11 | CN | 4-OMe-phenyl | OCH$_2$ | 2-quinoline | H, — | — | — | — | — |
| 652 | A11 | CN | 4-pyrazolyl | OCH$_2$ | 2-quinoline | H, — | — | — | — | — |
| 653 | A11 | CN | 3-(1-methyl-1H-pyrazolyl) | OCH$_2$ | 2-quinoline | H, — | — | — | — | — |
| 654 | A11 | CN | 4-(1-methyl-1H-pyrazolyl) | OCH$_2$ | 2-quinoline | H, — | — | — | — | — |

| Ex. # | HET | W | X | Y | Z | R1a, R1b | R2 | R3 | R4 | R7 |
|---|---|---|---|---|---|---|---|---|---|---|
| 655 | A11 | CN | 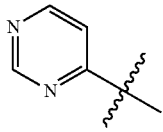 | OCH2 | 2-quinoline | H, — | — | — | — | — |
| 656 | A11 | CN | 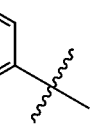 | OCH2 | 2-quinoline | H, — | — | — | — | — |
| 657 | A11 | CN | 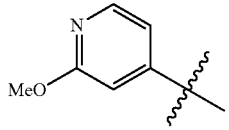 [SMILES: *c1ccnc(OC)c1] | OCH2 | 2-quinoline | H, — | — | — | — | — |
| 658 | A11 | CN | 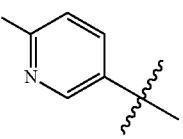 | OCH2 | 2-quinoline | H, — | — | — | — | — |
| 659 | A11 | CN | 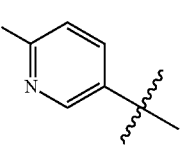 | OCH2 | 2-quinoline | H, — | — | — | — | — |
| 660 | A11 | CN | 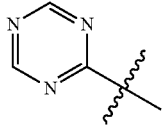 | OCH2 | 2-quinoline | H, — | — | — | — | — |
| 661 | A11 | CN | 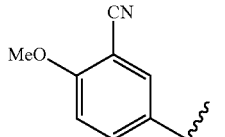 | OCH2 | 2-quinoline | H, — | — | — | — | — |
| 662 | A11 | CN | 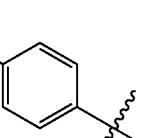 | OCH2 | 2-quinoline | H, — | — | — | — | — |
| 663 | A12 | CN | 4-pyridinyl | OCH2 | 2-quinoline | H, — | — | — | — | — |
| 664 | A12 | CN | 4-OMe-phenyl | OCH2 | 2-quinoline | H, — | — | — | — | — |
| 665 | A12 | CN | 4-pyrazolyl | OCH2 | 2-quinoline | H, — | — | — | — | — |
| 666 | A12 | CN | 3-(1-methyl-1H-pyrazolyl) | OCH2 | 2-quinoline | H, — | — | — | — | — |
| 667 | A12 | CN | 4-(1-methyl-1H-pyrazolyl) | OCH2 | 2-quinoline | H, — | — | — | — | — |
| 668 | A12 | CN | 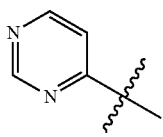 | OCH2 | 2-quinoline | H, — | — | — | — | — |

-continued

| Ex. # | HET | W | X | Y | Z | $R_{1a}, R_{1b}$ | $R_2$ | $R_3$ | $R_4$ | $R_7$ |
|---|---|---|---|---|---|---|---|---|---|---|
| 669 | A12 | CN | 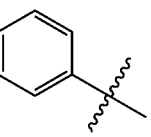 | $OCH_2$ | 2-quinoline | H, — | — | — | — | — |
| 670 | A12 | CN | 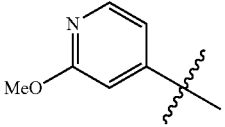 | $OCH_2$ | 2-quinoline | H, — | — | — | — | — |
| 671 | A12 | CN | 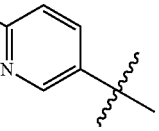 | $OCH_2$ | 2-quinoline | H, — | — | — | — | — |
| 672 | A12 | CN | 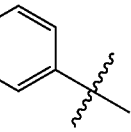 | $OCH_2$ | 2-quinoline | H, — | — | — | — | — |
| 673 | A12 | CN | 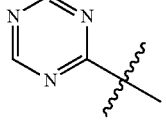 | $OCH_2$ | 2-quinoline | H, — | — | — | — | — |
| 674 | A12 | CN | 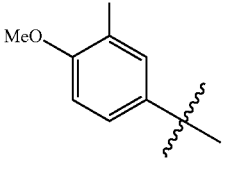 | $OCH_2$ | 2-quinoline | H, — | — | — | — | — |
| 675 | A12 | CN | 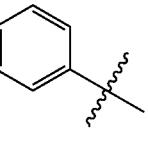 | $OCH_2$ | 2-quinoline | H, — | — | — | — | — |
| 676 | A13 | CN | 4-pyridinyl | $OCH_2$ | 2-quinoline | H, H | — | — | — | — |
| 677 | A13 | CN | 4-OMe-phenyl | $OCH_2$ | 2-quinoline | H, H | — | — | — | — |
| 678 | A13 | CN | 4-pyrazolyl | $OCH_2$ | 2-quinoline | H, H | — | — | — | — |
| 679 | A13 | CN | 3-(1-methyl-1H-pyrazolyl) | $OCH_2$ | 2-quinoline | H, H | — | — | — | — |
| 680 | A13 | CN | 4-(1-methyl-1H-pyrazolyl) | $OCH_2$ | 2-quinoline | H, H | — | — | — | — |
| 681 | A13 | CN | 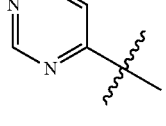 | $OCH_2$ | 2-quinoline | H, H | — | — | — | — |
| 682 | A13 | CN | 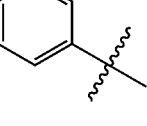 | $OCH_2$ | 2-quinoline | H, H | — | — | — | — |

-continued

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 683 | A13 | CN | 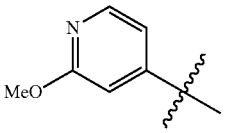 | OCH$_2$ | 2-quinoline | H, H | — | — | — | — |
| 684 | A13 | CN | 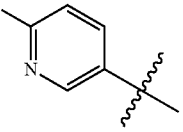 | OCH$_2$ | 2-quinoline | H, H | — | — | — | — |
| 685 | A13 | CN | 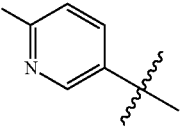 | OCH$_2$ | 2-quinoline | H, H | — | — | — | — |
| 686 | A13 | CN | 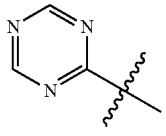 | OCH$_2$ | 2-quinoline | H, H | — | — | — | — |
| 687 | A13 | CN | 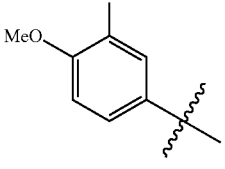 | OCH$_2$ | 2-quinoline | H, H | — | — | — | — |
| 688 | A13 | CN | 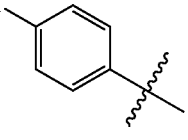 | OCH$_2$ | 2-quinoline | H, H | — | — | — | — |
| 689 | A14 | CN | 4-pyridinyl | OCH$_2$ | 2-quinoline | H, H | — | — | — | — |
| 690 | A14 | CN | 4-OMe-phenyl | OCH$_2$ | 2-quinoline | H, H | — | — | — | — |
| 691 | A14 | CN | 4-pyrazolyl | OCH$_2$ | 2-quinoline | H, H | — | — | — | — |
| 692 | A14 | CN | 3-(1-methyl-1H-pyrazolyl) | OCH$_2$ | 2-quinoline | H, H | — | — | — | — |
| 693 | A14 | CN | 4-(1-methyl-1H-pyrazolyl) | OCH$_2$ | 2-quinoline | H, H | — | — | — | — |
| 694 | A14 | CN | 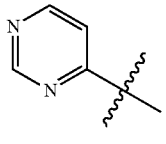 | OCH$_2$ | 2-quinoline | H, H | — | — | — | — |
| 695 | A14 | CN | 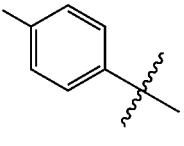 | OCH$_2$ | 2-quinoline | H, H | — | — | — | — |
| 696 | A14 | CN | 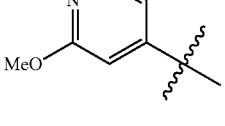 | OCH$_2$ | 2-quinoline | H, H | — | — | — | — |

-continued

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 697 | A14 | CN | 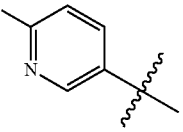 2-MeO-pyridin-5-yl | OCH$_2$ | 2-quinoline | H, H | — | — | — | — |
| 698 | A14 | CN | 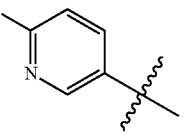 2-HO-pyridin-5-yl | OCH$_2$ | 2-quinoline | H, H | — | — | — | — |
| 699 | A14 | CN | 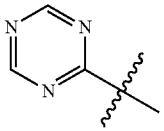 1,3,5-triazin-2-yl | OCH$_2$ | 2-quinoline | H, H | — | — | — | — |
| 700 | A14 | CN | 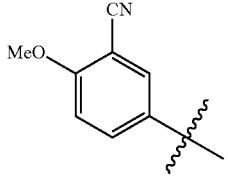 [SMILES: *c1ccc(OC)c(C#N)c1] 3-CN-4-MeO-phenyl | OCH$_2$ | 2-quinoline | H, H | — | — | — | — |
| 701 | A14 | CN | 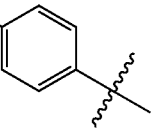 4-Cl-phenyl | OCH$_2$ | 2-quinoline | H, H | — | — | — | — |
| 702 | A15 | CN | 4-pyridinyl | OCH$_2$ | 2-quinoline | H, — | — | — | — | — |
| 703 | A15 | CN | 4-OMe-phenyl | OCH$_2$ | 2-quinoline | H, — | — | — | — | — |
| 704 | A15 | CN | 4-pyrazolyl | OCH$_2$ | 2-quinoline | H, — | — | — | — | — |
| 705 | A15 | CN | 3-(1-methyl-1H-pyrazolyl) | OCH$_2$ | 2-quinoline | H, — | — | — | — | — |
| 706 | A15 | CN | 4-(1-methyl-1H-pyrazolyl) | OCH$_2$ | 2-quinoline | H, — | — | — | — | — |
| 707 | A15 | CN | 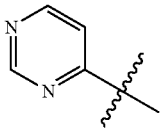 pyrimidin-4-yl | OCH$_2$ | 2-quinoline | H, — | — | — | — | — |
| 708 | A15 | CN | 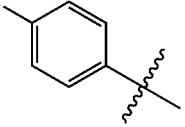 4-CN-phenyl | OCH$_2$ | 2-quinoline | H, — | — | — | — | — |
| 709 | A15 | CN | 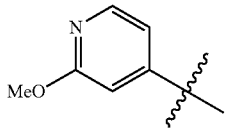 2-MeO-pyridin-4-yl | OCH$_2$ | 2-quinoline | H, — | — | — | — | — |
| 710 | A15 | CN | 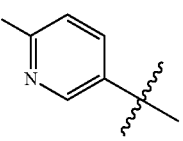 2-MeO-pyridin-5-yl | OCH$_2$ | 2-quinoline | H, — | — | — | — | — |

-continued

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 711 | A15 | CN | 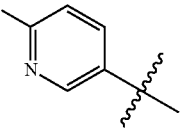 | OCH$_2$ | 2-quinoline | H, — | — | — | — | — |
| 712 | A15 | CN | 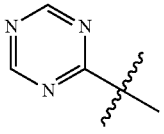 [SMILES: *c1ncncn1] | OCH$_2$ | 2-quinoline | H, — | — | — | — | — |
| 713 | A15 | CN | 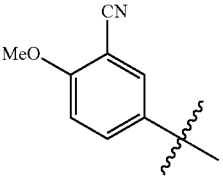 [SMILES: *c1ccc(OC)c(C#N)c1] | OCH$_2$ | 2-quinoline | H, — | — | — | — | — |
| 714 | A15 | CN | 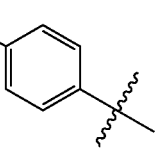 | OCH$_2$ | 2-quinoline | H, — | — | — | — | — |
| 715 | A19 | CN | 4-pyridinyl | OCH$_2$ | 2-quinoline | H, — | — | — | — | — |
| 716 | A19 | CN | 4-OMe-phenyl | OCH$_2$ | 2-quinoline | H, — | — | — | — | — |
| 717 | A19 | CN | 4-pyrazolyl | OCH$_2$ | 2-quinoline | H, — | — | — | — | — |
| 718 | A19 | CN | 3-(1-methyl-1H-pyrazolyl) | OCH$_2$ | 2-quinoline | H, — | — | — | — | — |
| 719 | A19 | CN | 4-(1-methyl-1H-pyrazolyl) | OCH$_2$ | 2-quinoline | H, — | — | — | — | — |
| 720 | A19 | CN | 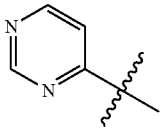 | OCH$_2$ | 2-quinoline | H, — | — | — | — | — |
| 721 | A19 | CN | 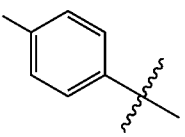 | OCH$_2$ | 2-quinoline | H, — | — | — | — | — |
| 722 | A19 | CN | 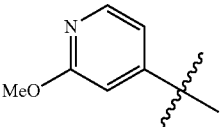 [SMILES: *c1ccnc(OC)c1] | OCH$_2$ | 2-quinoline | H, — | — | — | — | — |
| 723 | A19 | CN | 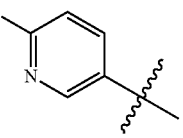 | OCH$_2$ | 2-quinoline | H, — | — | — | — | — |
| 724 | A19 | CN | 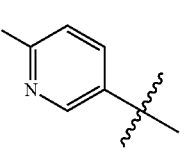 | OCH$_2$ | 2-quinoline | H, — | — | — | — | — |

-continued

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 725 | A19 | CN | (1,3,5-triazin-2-yl) | OCH$_2$ | 2-quinoline | H, — | — | — | — | — |
| 726 | A19 | CN | 2-MeO-5-CN-phenyl | OCH$_2$ | 2-quinoline | H, — | — | — | — | — |
| 727 | A19 | CN | 4-Cl-phenyl | OCH$_2$ | 2-quinoline | H, — | — | — | — | — |
| 728 | A20 | CN | 4-pyridinyl | OCH$_2$ | 2-quinoline | H, H | — | — | — | — |
| 729 | A20 | CN | 4-OMe-phenyl | OCH$_2$ | 2-quinoline | H, H | — | — | — | — |
| 730 | A20 | CN | 4-pyrazolyl | OCH$_2$ | 2-quinoline | H, H | — | — | — | — |
| 731 | A20 | CN | 3-(1-methyl-1H-pyrazolyl) | OCH$_2$ | 2-quinoline | H, H | — | — | — | — |
| 732 | A20 | CN | 4-(1-methyl-1H-pyrazolyl) | OCH$_2$ | 2-quinoline | H, H | — | — | — | — |
| 733 | A20 | CN | pyrimidin-4-yl | OCH$_2$ | 2-quinoline | H, H | — | — | — | — |
| 734 | A20 | CN | 4-CN-phenyl | OCH$_2$ | 2-quinoline | H, H | — | — | — | — |
| 735 | A20 | CN | 2-MeO-pyridin-4-yl | OCH$_2$ | 2-quinoline | H, H | — | — | — | — |
| 736 | A20 | CN | 6-MeO-pyridin-3-yl | OCH$_2$ | 2-quinoline | H, H | — | — | — | — |
| 737 | A20 | CN | 6-HO-pyridin-3-yl | OCH$_2$ | 2-quinoline | H, H | — | — | — | — |
| 738 | A20 | CN | (1,3,5-triazin-2-yl) | OCH$_2$ | 2-quinoline | H, H | — | — | — | — |

-continued

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 739 | A20 | CN | 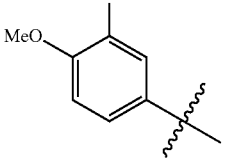 | OCH$_2$ | 2-quinoline | H, H | — | — | — | — |
| 740 | A20 | CN | 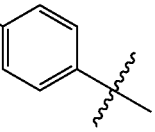 | OCH$_2$ | 2-quinoline | H, H | — | — | — | — |
| 741 | A32 | CN | 4-pyridinyl | OCH$_2$ | 2-quinoline | — | H, H | — | — | H |
| 742 | A32 | CN | 4-OMe-phenyl | OCH$_2$ | 2-quinoline | — | H, H | — | — | H |
| 743 | A32 | CN | 4-pyrazolyl | OCH$_2$ | 2-quinoline | — | H, H | — | — | H |
| 744 | A32 | CN | 3-(1-methyl-1H-pyrazolyl) | OCH$_2$ | 2-quinoline | — | H, H | — | — | H |
| 745 | A32 | CN | 4-(1-methyl-1H-pyrazolyl) | OCH$_2$ | 2-quinoline | — | H, H | — | — | H |
| 746 | A32 | CN | 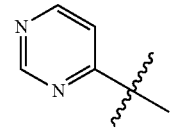 | OCH$_2$ | 2-quinoline | — | H, H | — | — | H |
| 747 | A32 | CN | 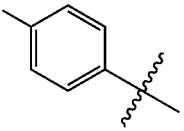 | OCH$_2$ | 2-quinoline | — | H, H | — | — | |
| 748 | A32 | CN | 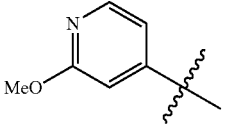 | OCH$_2$ | 2-quinoline | — | H, H | — | — | H |
| 749 | A32 | CN | 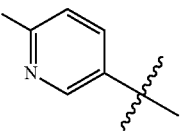 | OCH$_2$ | 2-quinoline | — | H, H | — | — | H |
| 750 | A32 | CN | 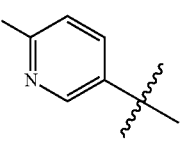 | OCH$_2$ | 2-quinoline | — | H, H | — | — | H |
| 751 | A32 | CN | 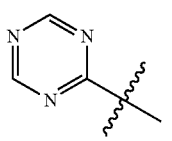 | OCH$_2$ | 2-quinoline | — | H, H | — | — | H |
| 752 | A32 | CN | 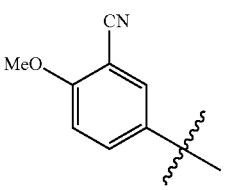 [SMILES: *c1ccc(OC)c(C#N)c1] | OCH$_2$ | 2-quinoline | — | H, H | — | — | H |

-continued

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 753 | A32 | CN | 4-chlorophenyl | OCH$_2$ | 2-quinoline | — | H, H | — | — | H |
| 1102 | A13 | Cl | 4-pyrazolyl | OCH$_2$ | 2-quinoline | Me, H | — | — | — | — |
| 1103 | A13 | Cl | 3-(1-methyl-1H-pyrazolyl) | OCH$_2$ | 2-quinoline | Me, H | — | — | — | — |
| 1104 | A13 | Cl | 4-(1-methyl-1H-pyrazolyl) | OCH$_2$ | 2-quinoline | Me, H | — | — | — | — |
| 1105 | A13 | Cl | 4-pyrimidinyl | OCH$_2$ | 2-quinoline | Me, H | — | — | — | — |
| 1106 | A13 | Cl | 4-cyanophenyl | OCH$_2$ | 2-quinoline | Me, H | — | — | — | — |
| 1107 | A13 | Cl | 2-methoxy-4-pyridyl | OCH$_2$ | 2-quinoline | Me, H | — | — | — | — |
| 1108 | A13 | Cl | 6-methoxy-3-pyridyl | OCH$_2$ | 2-quinoline | Me, H | — | — | — | — |
| 1109 | A13 | Cl | 6-hydroxy-3-pyridyl | OCH$_2$ | 2-quinoline | Me, H | — | — | — | — |
| 1110 | A13 | Cl | 2-(1,3,5-triazinyl) | OCH$_2$ | 2-quinoline | Me, H | — | — | — | — |
| 1111 | A13 | Cl | 3-cyano-4-methoxyphenyl | OCH$_2$ | 2-quinoline | Me, H | — | — | — | — |

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 1112 | A13 | Cl | 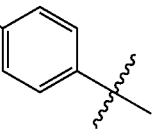 | OCH$_2$ | 2-quinoline | Me, H | — | — | — | — |

In a further aspect the compounds of the disclosure are embodied in with distinct examples listed in the table below taken from Formula (III):

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 754 | A1 | Cl | 4-pyridinyl | OCH$_2$ | 2-quinoline | — | — | H | H | — |
| 755 | A1 | Cl | 4-OMe-phenyl | OCH$_2$ | 2-quinoline | — | — | H | H | — |
| 756 | A1 | Cl | 4-pyrazolyl | OCH$_2$ | 2-quinoline | — | — | H | H | — |
| 757 | A1 | Cl | 3-(1-methyl-1H-pyrazolyl) | OCH$_2$ | 2-quinoline | — | — | H | H | — |
| 758 | A1 | Cl | 4-(1-methyl-1H-pyrazolyl) | OCH$_2$ | 2-quinoline | — | — | H | H | — |
| 759 | A1 | Cl | 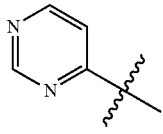 [SMILES: *c1ccncn1] | OCH$_2$ | 2-quinoline | — | — | H | H | — |
| 760 | A1 | Cl | 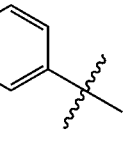 | OCH$_2$ | 2-quinoline | — | — | H | H | — |
| 761 | A1 | Cl | 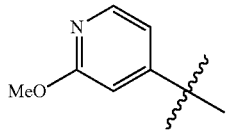 [SMILES: *c1ccnc(OC)c1] | OCH$_2$ | 2-quinoline | — | — | H | H | — |
| 762 | A1 | Cl | 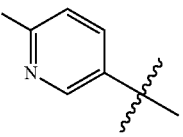 | OCH$_2$ | 2-quinoline | — | — | H | H | — |
| 763 | A1 | Cl | 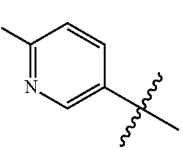 | OCH$_2$ | 2-quinoline | — | — | H | H | — |
| 764 | A1 | Cl | 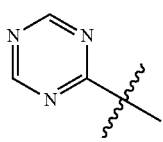 [SMILES: *c1ncncn1] | OCH$_2$ | 2-quinoline | — | — | H | H | — |
| 765 | A1 | Cl | 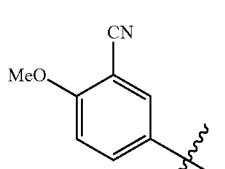 | OCH$_2$ | 2-quinoline | — | — | H | H | — |

-continued

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 766 | A1 | Cl | 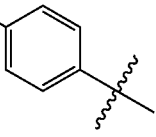 | OCH$_2$ | 2-quinoline | — | — | H | H | — |
| 767 | A2 | Cl | 4-pyridinyl | OCH$_2$ | 2-quinoline | — | — | H | H | H |
| 768 | A2 | Cl | 4-pyridinyl | OCH$_2$ | 2-quinoline | — | — | H | H | Me |
| 770 | A2 | Cl | 4-OMe-phenyl | OCH$_2$ | 2-quinoline | — | — | H | H | H |
| 771 | A2 | Cl | 4-OMe-phenyl | OCH$_2$ | 2-quinoline | — | — | H | H | Me |
| 773 | A2 | Cl | 4-pyrazolyl | OCH$_2$ | 2-quinoline | — | — | H | H | H |
| 774 | A2 | Cl | 4-pyrazolyl | OCH$_2$ | 2-quinoline | — | — | H | H | Me |
| 776 | A2 | Cl | 3-(1-methyl-1H-pyrazolyl) | OCH$_2$ | 2-quinoline | — | — | H | H | H |
| 777 | A2 | Cl | 3-(1-methyl-1H-pyrazolyl) | OCH$_2$ | 2-quinoline | — | — | H | H | Me |
| 779 | A2 | Cl | 4-(1-methyl-1H-pyrazolyl) | OCH$_2$ | 2-quinoline | — | — | H | H | H |
| 780 | A2 | Cl | 4-(1-methyl-1H-pyrazolyl) | OCH$_2$ | 2-quinoline | — | — | H | H | Me |
| 782 | A2 | Cl | 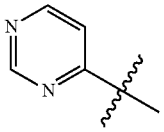 | OCH$_2$ | 2-quinoline | — | — | H | H | H |
| 783 | A2 | Cl | 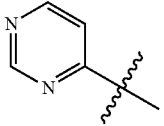 | OCH$_2$ | 2-quinoline | — | — | H | H | Me |
| 785 | A2 | Cl | 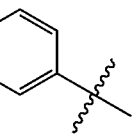 | OCH$_2$ | 2-quinoline | — | — | H | H | H |
| 786 | A2 | Cl | 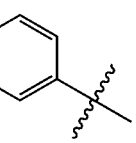 | OCH$_2$ | 2-quinoline | — | — | H | H | Me |
| 788 | A2 | Cl | 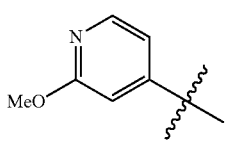 | OCH$_2$ | 2-quinoline | — | — | H | H | H |
| 789 | A2 | Cl | 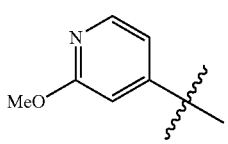 | OCH$_2$ | 2-quinoline | — | — | H | H | Me |
| 791 | A2 | Cl | 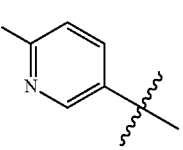 | OCH$_2$ | 2-quinoline | — | — | H | H | H |
| 792 | A2 | Cl | 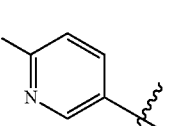 | OCH$_2$ | 2-quinoline | — | — | H | H | Me |

-continued

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 794 | A2 | Cl | 5-(2-hydroxypyridinyl) | OCH$_2$ | 2-quinoline | — | — | H | H | H |
| 795 | A2 | Cl | 5-(2-hydroxypyridinyl) | OCH$_2$ | 2-quinoline | — | — | H | H | Me |
| 797 | A2 | Cl | 2-(1,3,5-triazinyl) | OCH$_2$ | 2-quinoline | — | — | H | H | H |
| 798 | A2 | Cl | 2-(1,3,5-triazinyl) | OCH$_2$ | 2-quinoline | — | — | H | H | Me |
| 800 | A2 | Cl | 3-cyano-4-methoxyphenyl | OCH$_2$ | 2-quinoline | — | — | H | H | H |
| 801 | A2 | Cl | 3-cyano-4-methoxyphenyl | OCH$_2$ | 2-quinoline | — | — | H | H | Me |
| 803 | A2 | Cl | 4-chlorophenyl | OCH$_2$ | 2-quinoline | — | — | H | H | H |
| 804 | A2 | Cl | 4-chlorophenyl | OCH$_2$ | 2-quinoline | — | — | H | H | Me |
| 806 | A6 | Cl | 4-pyridinyl | OCH$_2$ | 2-quinoline | H, — | — | — | — | H |
| 807 | A6 | Cl | 4-OMe-phenyl | OCH$_2$ | 2-quinoline | H, — | — | — | — | H |
| 808 | A6 | Cl | 4-pyrazolyl | OCH$_2$ | 2-quinoline | H, — | — | — | — | H |
| 809 | A6 | Cl | 3-(1-methyl-1H-pyrazolyl) | OCH$_2$ | 2-quinoline | H, — | — | — | — | H |
| 810 | A6 | Cl | 4-(1-methyl-1H-pyrazolyl) | OCH$_2$ | 2-quinoline | H, — | — | — | — | H |
| 811 | A6 | Cl | 4-pyrimidinyl | OCH$_2$ | 2-quinoline | H, — | — | — | — | H |

-continued

| Ex. # | HET | W | X | Y | Z | R1a, R1b | R2 | R3 | R4 | R7 |
|---|---|---|---|---|---|---|---|---|---|---|
| 812 | A6 | Cl | 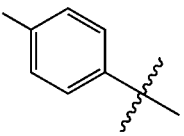 4-CN-phenyl | OCH2 | 2-quinoline | H, — | — | — | — | H |
| 813 | A6 | Cl | 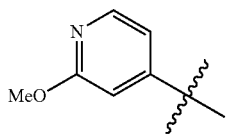 [SMILES: *c1ccnc(OC)c1] 2-MeO-pyridin-4-yl | OCH2 | 2-quinoline | H, — | — | — | — | H |
| 814 | A6 | Cl | 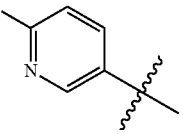 6-MeO-pyridin-3-yl | OCH2 | 2-quinoline | H, — | — | — | — | H |
| 815 | A6 | Cl | 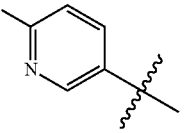 6-HO-pyridin-3-yl | OCH2 | 2-quinoline | H, — | — | — | — | H |
| 816 | A6 | Cl | 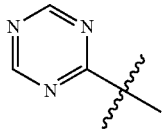 [SMILES: *c1ncncn1] 1,3,5-triazin-2-yl | OCH2 | 2-quinoline | H, — | — | — | — | H |
| 817 | A6 | Cl | 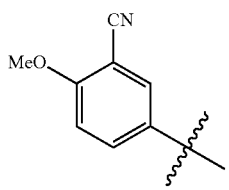 2-MeO-5-CN-phenyl | OCH2 | 2-quinoline | H, — | — | — | — | H |
| 818 | A6 | Cl | 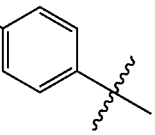 4-Cl-phenyl | OCH2 | 2-quinoline | H, — | — | — | — | H |
| 819 | A11 | Cl | 4-pyridinyl | OCH2 | 2-quinoline | H, — | — | — | — | — |
| 820 | A11 | Cl | 4-OMe-phenyl | OCH2 | 2-quinoline | H, — | — | — | — | — |
| 821 | A11 | Cl | 4-pyrazolyl | OCH2 | 2-quinoline | H, — | — | — | — | — |
| 822 | A11 | Cl | 3-(1-methyl-1H-pyrazolyl) | OCH2 | 2-quinoline | H, — | — | — | — | — |
| 823 | A11 | Cl | 4-(1-methyl-1H-pyrazolyl) | OCH2 | 2-quinoline | H, — | — | — | — | — |
| 824 | A11 | Cl | 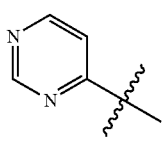 [SMILES: *c1ccncn1] pyrimidin-4-yl | OCH2 | 2-quinoline | H, — | — | — | — | — |
| 825 | A11 | Cl | 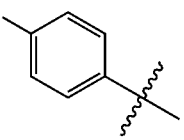 4-CN-phenyl | OCH2 | 2-quinoline | H, — | — | — | — | — |

-continued

| Ex. # | HET | W | X | Y | Z | R₁ₐ, R₁ᵦ | R₂ | R₃ | R₄ | R₇ |
|---|---|---|---|---|---|---|---|---|---|---|
| 826 | A11 | Cl | 2-MeO-pyridin-4-yl | OCH₂ | 2-quinoline | H, — | — | — | — | — |
| 827 | A11 | Cl | 2-MeO-pyridin-5-yl | OCH₂ | 2-quinoline | H, — | — | — | — | — |
| 828 | A11 | Cl | 2-HO-pyridin-5-yl | OCH₂ | 2-quinoline | H, — | — | — | — | — |
| 829 | A11 | Cl | 1,3,5-triazin-2-yl | OCH₂ | 2-quinoline | H, — | — | — | — | — |
| 830 | A11 | Cl | 2-MeO-5-CN-phenyl | OCH₂ | 2-quinoline | H, — | — | — | — | — |
| 831 | A11 | Cl | 4-Cl-phenyl | OCH₂ | 2-quinoline | H, — | — | — | — | — |
| 832 | A12 | Cl | 4-pyridinyl | OCH₂ | 2-quinoline | H, — | — | — | — | — |
| 833 | A12 | Cl | 4-OMe-phenyl | OCH₂ | 2-quinoline | H, — | — | — | — | — |
| 834 | A12 | Cl | 4-pyrazolyl | OCH₂ | 2-quinoline | H, — | — | — | — | — |
| 835 | A12 | Cl | 3-(1-methyl-1H-pyrazolyl) | OCH₂ | 2-quinoline | H, — | — | — | — | — |
| 836 | A12 | Cl | 4-(1-methyl-1H-pyrazolyl) | OCH₂ | 2-quinoline | H, — | — | — | — | — |
| 837 | A12 | Cl | pyrimidin-4-yl | OCH₂ | 2-quinoline | H, — | — | — | — | — |
| 838 | A12 | Cl | 4-CN-phenyl | OCH₂ | 2-quinoline | H, — | — | — | — | — |
| 839 | A12 | Cl | 2-MeO-pyridin-4-yl | OCH₂ | 2-quinoline | H, — | — | — | — | — |

-continued

| Ex. # | HET | W | X | Y | Z | $R_{1a}, R_{1b}$ | $R_2$ | $R_3$ | $R_4$ | $R_7$ |
|---|---|---|---|---|---|---|---|---|---|---|
| 840 | A12 | Cl | MeO-pyridin-5-yl (2-OMe) | $OCH_2$ | 2-quinoline | H, — | — | — | — | — |
| 841 | A12 | Cl | HO-pyridin-5-yl (2-OH) | $OCH_2$ | 2-quinoline | H, — | — | — | — | — |
| 842 | A12 | Cl | 1,3,5-triazin-2-yl | $OCH_2$ | 2-quinoline | H, — | — | — | — | — |
| 843 | A12 | Cl | 2-MeO-5-CN-phenyl | $OCH_2$ | 2-quinoline | H, — | — | — | — | — |
| 844 | A12 | Cl | 4-Cl-phenyl | $OCH_2$ | 2-quinoline | H, — | — | — | — | — |
| 845 | A13 | Cl | 4-pyridinyl | $OCH_2$ | 2-quinoline | H, H | — | — | — | — |
| 846 | A13 | Cl | 4-OMe-phenyl | $OCH_2$ | 2-quinoline | H, H | — | — | — | — |
| 847 | A13 | Cl | 4-pyrazolyl | $OCH_2$ | 2-quinoline | H | — | — | — | — |
| 848 | A13 | Cl | 3-(1-methyl-1H-pyrazolyl) | $OCH_2$ | 2-quinoline | H, H | — | — | — | — |
| 849 | A13 | Cl | 4-(1-methyl-1H-pyrazolyl) | $OCH_2$ | 2-quinoline | H, H | — | — | — | — |
| 850 | A13 | Cl | pyrimidin-4-yl | $OCH_2$ | 2-quinoline | H, H | — | — | — | — |
| 851 | A13 | Cl | 4-CN-phenyl | $OCH_2$ | 2-quinoline | H, H | — | — | — | — |
| 852 | A13 | Cl | 2-MeO-pyridin-4-yl | $OCH_2$ | 2-quinoline | H, H | — | — | — | — |
| 853 | A13 | Cl | 2-MeO-pyridin-5-yl | $OCH_2$ | 2-quinoline | H, H | — | — | — | — |

-continued

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 854 | A13 | Cl | 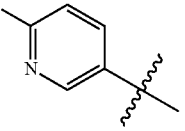 | OCH$_2$ | 2-quinoline | H, H | — | — | — | — |
| 855 | A13 | Cl | 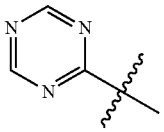 | OCH$_2$ | 2-quinoline | H, H | — | — | — | — |
| 856 | A13 | Cl | 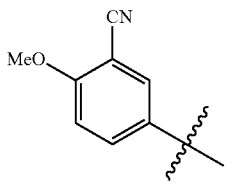 [SMILES: *c1ccc(OC)c(C#N)c1] | OCH$_2$ | 2-quinoline | H, H | — | — | — | — |
| 857 | A13 | Cl | 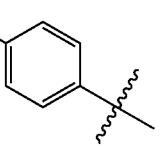 | OCH$_2$ | 2-quinoline | H, H | — | — | — | — |
| 858 | A14 | Cl | 4-pyridinyl | OCH$_2$ | 2-quinoline | H, H | — | — | — | — |
| 859 | A14 | Cl | 4-OMe-phenyl | OCH$_2$ | 2-quinoline | H, H | — | — | — | — |
| 860 | A14 | Cl | 4-pyrazolyl | OCH$_2$ | 2-quinoline | H, H | — | — | — | — |
| 861 | A14 | Cl | 3-(1-methyl-1H-pyrazolyl) | OCH$_2$ | 2-quinoline | H, H | — | — | — | — |
| 862 | A14 | Cl | 4-(1-methyl-1H-pyrazolyl) | OCH$_2$ | 2-quinoline | H, H | — | — | — | — |
| 863 | A14 | Cl | 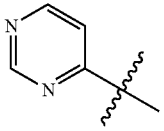 | OCH$_2$ | 2-quinoline | H, H | — | — | — | — |
| 864 | A14 | Cl | 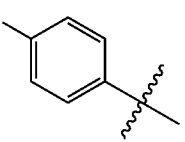 | OCH$_2$ | 2-quinoline | H, H | — | — | — | — |
| 865 | A14 | Cl | 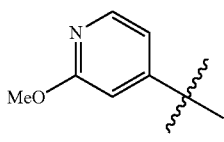 [SMILES: *c1ccnc(OC)c1] | OCH$_2$ | 2-quinoline | H, H | — | — | — | — |
| 866 | A14 | Cl | 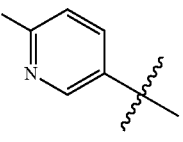 | OCH$_2$ | 2-quinoline | H, H | — | — | — | — |
| 867 | A14 | Cl | 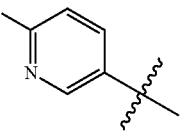 | OCH$_2$ | 2-quinoline | H, H | — | — | — | — |

-continued

| Ex. # | HET | W | X | Y | Z | R1a, R1b | R2 | R3 | R4 | R7 |
|---|---|---|---|---|---|---|---|---|---|---|
| 868 | A14 | Cl | 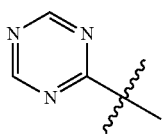 | OCH2 | 2-quinoline | H, H | — | — | — | — |
| 869 | A14 | Cl | 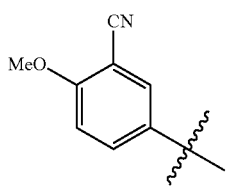 [SMILES: *c1ccc(OC)c(C#N)c1] | OCH2 | 2-quinoline | H, H | — | — | — | — |
| 870 | A14 | Cl | 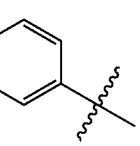 | OCH2 | 2-quinoline | H, H | — | — | — | — |
| 871 | A15 | Cl | 4-pyridinyl | OCH2 | 2-quinoline | H, — | — | — | — | — |
| 872 | A15 | Cl | 4-OMe-phenyl | OCH2 | 2-quinoline | H, — | — | — | — | — |
| 873 | A15 | Cl | 4-pyrazolyl | OCH2 | 2-quinoline | H, — | — | — | — | — |
| 874 | A15 | Cl | 3-(1-methyl-1H-pyrazolyl) | OCH2 | 2-quinoline | H, — | — | — | — | — |
| 875 | A15 | Cl | 4-(1-methyl-1H-pyrazolyl) | OCH2 | 2-quinoline | H, — | — | — | — | — |
| 876 | A15 | Cl | 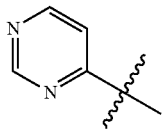 [SMILES: *c1ccncn1] | OCH2 | 2-quinoline | H, — | — | — | — | — |
| 877 | A15 | Cl | 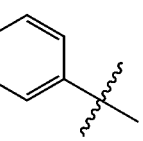 | OCH2 | 2-quinoline | H, — | — | — | — | — |
| 878 | A15 | Cl | 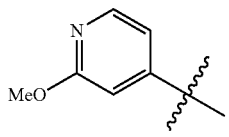 [SMILES: *c1ccnc(OC)c1] | OCH2 | 2-quinoline | H, — | — | — | — | — |
| 879 | A15 | Cl | 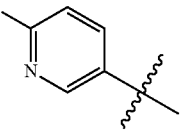 | OCH2 | 2-quinoline | H, — | — | — | — | — |
| 880 | A15 | Cl | 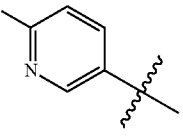 | OCH2 | 2-quinoline | H, — | — | — | — | — |
| 881 | A15 | Cl | 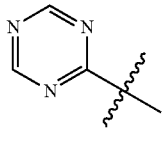 | OCH2 | 2-quinoline | H, — | — | — | — | — |

-continued

| Ex. # | HET | W | X | Y | Z | R_{1a}, R_{1b} | R_2 | R_3 | R_4 | R_7 |
|---|---|---|---|---|---|---|---|---|---|---|
| 882 | A15 | Cl | 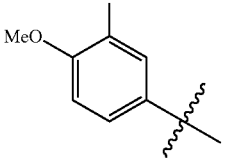 | OCH_2 | 2-quinoline | H, — | — | — | — | — |
| 883 | A15 | Cl | 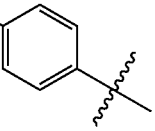 | OCH_2 | 2-quinoline | H, — | — | — | — | — |
| 884 | A19 | Cl | 4-pyridinyl | OCH_2 | 2-quinoline | H, — | — | — | — | — |
| 885 | A19 | Cl | 4-OMe-phenyl | OCH_2 | 2-quinoline | H, — | — | — | — | — |
| 886 | A19 | Cl | 4-pyrazolyl | OCH_2 | 2-quinoline | H, — | — | — | — | — |
| 887 | A19 | Cl | 3-(1-methyl-1H-pyrazolyl) | OCH_2 | 2-quinoline | H, — | — | — | — | — |
| 888 | A19 | Cl | 4-(1-methyl-1H-pyrazolyl) | OCH_2 | 2-quinoline | H, — | — | — | — | — |
| 889 | A19 | Cl | 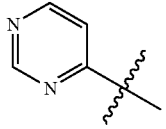 [SMILES: *c1ccncn1] | OCH_2 | 2-quinoline | H, — | — | — | — | — |
| 890 | A19 | Cl | 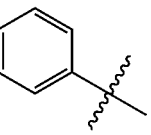 | OCH_2 | 2-quinoline | H, — | — | — | — | — |
| 891 | A19 | Cl | 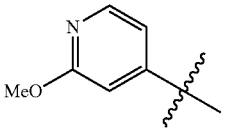 | OCH_2 | 2-quinoline | H, — | — | — | — | — |
| 892 | A19 | Cl | 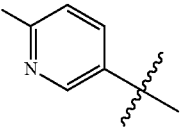 | OCH_2 | 2-quinoline | H, — | — | — | — | — |
| 893 | A19 | Cl | 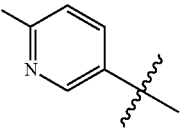 | OCH_2 | 2-quinoline | H, — | — | — | — | — |
| 894 | A19 | Cl | 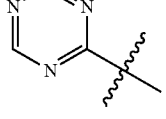 | OCH_2 | 2-quinoline | H, — | — | — | — | — |
| 895 | A19 | Cl | 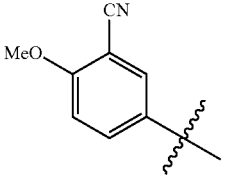 [SMILES: *c1ccc(OC)c(C#N)c1] | OCH_2 | 2-quinoline | H, — | — | — | — | — |

-continued

| Ex. # | HET | W | X | Y | Z | $R_{1a}, R_{1b}$ | $R_2$ | $R_3$ | $R_4$ | $R_7$ |
|---|---|---|---|---|---|---|---|---|---|---|
| 896 | A19 | Cl | 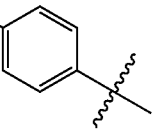 4-Cl-phenyl | $OCH_2$ | 2-quinoline | H, — | — | — | — | — |
| 897 | A20 | Cl | 4-pyridinyl | $OCH_2$ | 2-quinoline | H, H | — | — | — | — |
| 898 | A20 | Cl | 4-OMe-phenyl | $OCH_2$ | 2-quinoline | H, H | — | — | — | — |
| 899 | A20 | Cl | 4-pyrazolyl | $OCH_2$ | 2-quinoline | H, H | — | — | — | — |
| 900 | A20 | Cl | 3-(1-methyl-1H-pyrazolyl) | $OCH_2$ | 2-quinoline | H, H | — | — | — | — |
| 901 | A20 | Cl | 4-(1-methyl-1H-pyrazolyl) | $OCH_2$ | 2-quinoline | H, H | — | — | — | — |
| 902 | A20 | Cl | 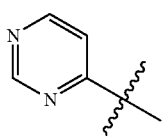 pyrimidinyl | $OCH_2$ | 2-quinoline | H, H | — | — | — | — |
| 903 | A20 | Cl | 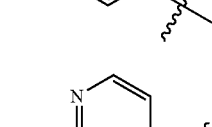 4-CN-phenyl | $OCH_2$ | 2-quinoline | H, H | — | — | — | — |
| 904 | A20 | Cl | 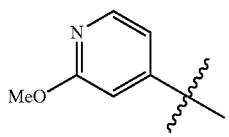 [SMILES: *c1ccnc(OC)c1] 2-MeO-pyridinyl | $OCH_2$ | 2-quinoline | H, H | — | — | — | — |
| 905 | A20 | Cl | 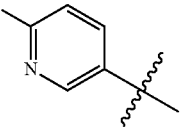 6-MeO-pyridinyl | $OCH_2$ | 2-quinoline | H, H | — | — | — | — |
| 906 | A20 | Cl | 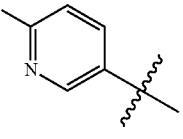 2-HO-pyridinyl | $OCH_2$ | 2-quinoline | H, H | — | — | — | — |
| 907 | A20 | Cl | 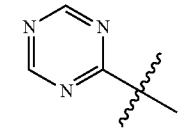 triazinyl | $OCH_2$ | 2-quinoline | H, H | — | — | — | — |
| 908 | A20 | Cl | 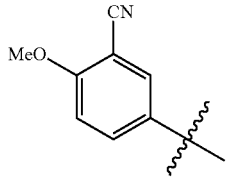 [SMILES: *c1ccc(OC)c(C#N)c1] 2-MeO-5-CN-phenyl | $OCH_2$ | 2-quinoline | H, H | — | — | — | — |
| 909 | A20 | Cl | 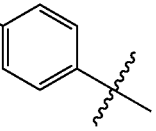 4-Cl-phenyl | $OCH_2$ | 2-quinoline | H, H | — | — | — | — |
| 910 | A32 | Cl | 4-pyridinyl | $OCH_2$ | 2-quinoline | — | H, H | — | — | H |
| 911 | A32 | Cl | 4-OMe-phenyl | $OCH_2$ | 2-quinoline | — | H, H | — | — | H |
| 912 | A32 | Cl | 4-pyrazolyl | $OCH_2$ | 2-quinoline | — | H, H | — | — | H |

-continued

| Ex. # | HET | W | X | Y | Z | R₁ₐ, R₁ᵦ | R₂ | R₃ | R₄ | R₇ |
|---|---|---|---|---|---|---|---|---|---|---|
| 913 | A32 | Cl | 3-(1-methyl-1H-pyrazolyl) | OCH₂ | 2-quinoline | — | H, H | — | — | H |
| 914 | A32 | Cl | 4-(1-methyl-1H-pyrazolyl) | OCH₂ | 2-quinoline | — | H, H | — | — | H |
| 915 | A32 | Cl | 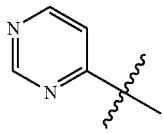 [SMILES: *c1ccncn1] | OCH₂ | 2-quinoline | — | H, H | — | — | H |
| 916 | A1 | CN | 4-pyridinyl | OCH₂ | 2-quinoline | — | — | H | H | — |
| 917 | A1 | CN | 4-OMe-phenyl | OCH₂ | 2-quinoline | — | — | H | H | — |
| 918 | A1 | CN | 4-pyrazolyl | OCH₂ | 2-quinoline | — | — | H | H | — |
| 919 | A1 | CN | 3-(1-methyl-1H-pyrazolyl) | OCH₂ | 2-quinoline | — | — | H | H | — |
| 920 | A1 | CN | 4-(1-methyl-1H-pyrazolyl) | OCH₂ | 2-quinoline | — | — | H | H | — |
| 921 | A1 | CN | 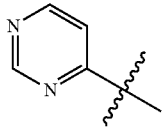 | OCH₂ | 2-quinoline | — | — | H | H | — |
| 922 | A1 | CN | 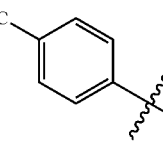 | OCH₂ | 2-quinoline | — | — | H | H | — |
| 923 | A1 | CN | 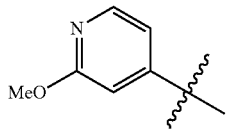 [SMILES: *c1ccnc(OC)c1] | OCH₂ | 2-quinoline | — | — | H | H | — |
| 924 | A1 | CN | 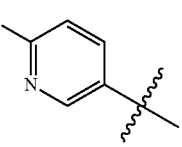 | OCH₂ | 2-quinoline | — | — | H | H | — |
| 925 | A1 | CN | 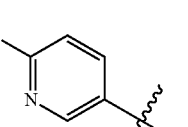 | OCH₂ | 2-quinoline | — | — | H | H | — |
| 926 | A1 | CN | 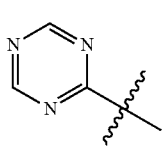 | OCH₂ | 2-quinoline | — | — | H | H | — |
| 927 | A1 | CN | 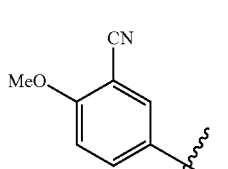 | OCH₂ | 2-quinoline | — | — | H | H | — |
| 928 | A1 | CN | 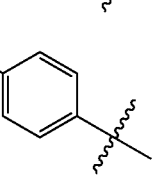 | OCH₂ | 2-quinoline | — | — | H | H | — |

-continued

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 929 | A2 | CN | 4-pyridinyl | OCH$_2$ | 2-quinoline | — | — | H | H | H |
| 930 | A2 | CN | 4-pyridinyl | OCH$_2$ | 2-quinoline | — | — | H | H | Me |
| 932 | A2 | CN | 4-OMe-phenyl | OCH$_2$ | 2-quinoline | — | — | H | H | H |
| 933 | A2 | CN | 4-OMe-phenyl | OCH$_2$ | 2-quinoline | — | — | H | H | Me |
| 935 | A2 | CN | 4-pyrazolyl | OCH$_2$ | 2-quinoline | — | — | H | H | H |
| 936 | A2 | CN | 4-pyrazolyl | OCH$_2$ | 2-quinoline | — | — | H | H | Me |
| 938 | A2 | CN | 3-(1-methyl-1H-pyrazolyl) | OCH$_2$ | 2-quinoline | — | — | H | H | H |
| 939 | A2 | CN | 3-(1-methyl-1H-pyrazolyl) | OCH$_2$ | 2-quinoline | — | — | H | H | Me |
| 941 | A2 | CN | 4-(1-methyl-1H-pyrazolyl) | OCH$_2$ | 2-quinoline | — | — | H | H | H |
| 942 | A2 | CN | 4-(1-methyl-1H-pyrazolyl) | OCH$_2$ | 2-quinoline | — | — | H | H | Me |
| 944 | A2 | CN | 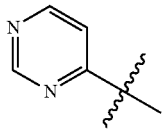 [SMILES: *c1ccncn1] | OCH$_2$ | 2-quinoline | — | — | H | H | H |
| 945 | A2 | CN | 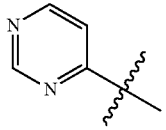 | OCH$_2$ | 2-quinoline | — | — | H | H | Me |
| 947 | A2 | CN | 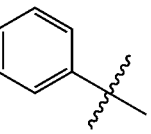 | OCH$_2$ | 2-quinoline | — | — | H | H | H |
| 948 | A2 | CN | 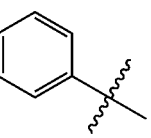 | OCH$_2$ | 2-quinoline | — | — | H | H | Me |
| 950 | A2 | CN | 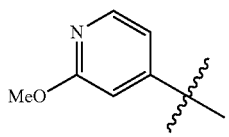 | OCH$_2$ | 2-quinoline | — | — | H | H | H |
| 951 | A2 | CN | 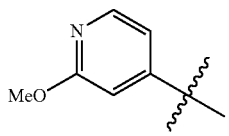 | OCH$_2$ | 2-quinoline | — | — | H | H | Me |
| 953 | A2 | CN | 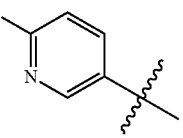 | OCH$_2$ | 2-quinoline | — | — | H | H | H |
| 954 | A2 | CN | 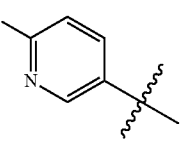 | OCH$_2$ | 2-quinoline | — | — | H | H | Me |
| 956 | A2 | CN | 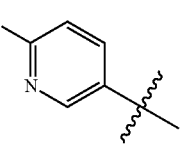 | OCH$_2$ | 2-quinoline | — | — | H | H | H |

-continued

| Ex. # | HET | W | X | Y | Z | $R_{1a}, R_{1b}$ | $R_2$ | $R_3$ | $R_4$ | $R_7$ |
|---|---|---|---|---|---|---|---|---|---|---|
| 957 | A2 | CN | 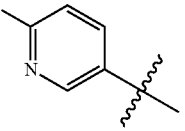 | OCH$_2$ | 2-quinoline | — | — | H | H | Me |
| 959 | A2 | CN | 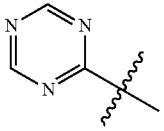 | OCH$_2$ | 2-quinoline | — | — | H | H | H |
| 960 | A2 | CN | 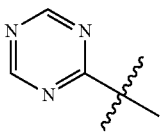 | OCH$_2$ | 2-quinoline | — | — | H | H | Me |
| 962 | A2 | CN | 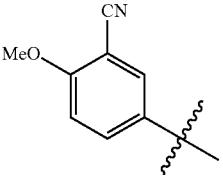 [SMILES: *c1ccc(OC)c(C#N)c1] | OCH$_2$ | 2-quinoline | — | — | H | H | H |
| 963 | A2 | CN | 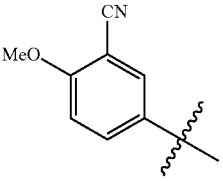 [SMILES: *c1ccc(OC)c(C#N)c1] | OCH$_2$ | 2-quinoline | — | — | H | H | Me |
| 965 | A2 | CN | 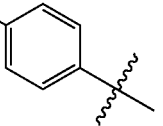 | OCH$_2$ | 2-quinoline | — | — | H | H | H |
| 966 | A2 | CN | 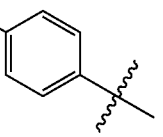 | OCH$_2$ | 2-quinoline | — | — | H | H | Me |
| 968 | A6 | CN | 4-pyridinyl | OCH$_2$ | 2-quinoline | H, — | — | — | — | H |
| 969 | A6 | CN | 4-OMe-phenyl | OCH$_2$ | 2-quinoline | H, — | — | — | — | H |
| 970 | A6 | CN | 4-pyrazolyl | OCH$_2$ | 2-quinoline | H, — | — | — | — | H |
| 971 | A6 | CN | 3-(1-methyl-1H-pyrazolyl) | OCH$_2$ | 2-quinoline | H, — | — | — | — | H |
| 972 | A6 | CN | 4-(1-methyl-1H-pyrazolyl) | OCH$_2$ | 2-quinoline | H, — | — | — | — | H |
| 973 | A6 | CN | 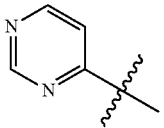 | OCH$_2$ | 2-quinoline | H, — | — | — | — | H |
| 974 | A6 | CN | 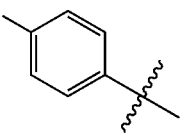 | OCH$_2$ | 2-quinoline | H, — | — | — | — | H |

-continued

| Ex. # | HET | W | X | Y | Z | R₁ₐ, R₁ᵦ | R₂ | R₃ | R₄ | R₇ |
|---|---|---|---|---|---|---|---|---|---|---|
| 975 | A6 | CN | 2-MeO-pyridin-4-yl | OCH₂ | 2-quinoline | H, — | — | — | — | H |
| 976 | A6 | CN | 2-MeO-pyridin-5-yl | OCH₂ | 2-quinoline | H, — | — | — | — | H |
| 977 | A6 | CN | 2-HO-pyridin-5-yl | OCH₂ | 2-quinoline | H, — | — | — | — | H |
| 978 | A6 | CN | 1,3,5-triazin-2-yl | OCH₂ | 2-quinoline | H, — | — | — | — | H |
| 979 | A6 | CN | 3-CN-4-MeO-phenyl | OCH₂ | 2-quinoline | H, — | — | — | — | H |
| 980 | A6 | CN | 4-Cl-phenyl | OCH₂ | 2-quinoline | H, — | — | — | — | H |
| 981 | A11 | CN | 4-pyridinyl | OCH₂ | 2-quinoline | H, — | — | — | — | — |
| 982 | A11 | CN | 4-OMe-phenyl | OCH₂ | 2-quinoline | H, — | — | — | — | — |
| 983 | A11 | CN | 4-pyrazolyl | OCH₂ | 2-quinoline | H, — | — | — | — | — |
| 984 | A11 | CN | 3-(1-methyl-1H-pyrazolyl) | OCH₂ | 2-quinoline | H, — | — | — | — | — |
| 985 | A11 | CN | 4-(1-methyl-1H-pyrazolyl) | OCH₂ | 2-quinoline | H, — | — | — | — | — |
| 986 | A11 | CN | pyrimidin-4-yl | OCH₂ | 2-quinoline | H, — | — | — | — | — |
| 987 | A11 | CN | 4-CN-phenyl | OCH₂ | 2-quinoline | H, — | — | — | — | — |
| 988 | A11 | CN | 2-MeO-pyridin-4-yl | OCH₂ | 2-quinoline | H, — | — | — | — | — |

-continued

| Ex. # | HET | W | X | Y | Z | R₁ₐ, R₁ᵦ | R₂ | R₃ | R₄ | R₇ |
|---|---|---|---|---|---|---|---|---|---|---|
| 989 | A11 | CN | 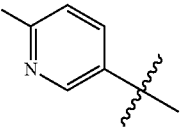 | OCH₂ | 2-quinoline | H, — | — | — | — | — |
| 990 | A11 | CN | 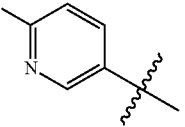 | OCH₂ | 2-quinoline | H, — | — | — | — | — |
| 991 | A11 | CN | 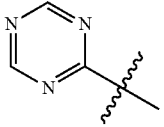 | OCH₂ | 2-quinoline | H, — | — | — | — | — |
| 992 | A11 | CN | 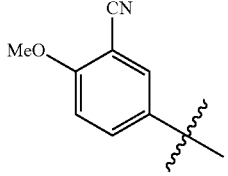 [SMILES: *c1ccc(OC)c(C#N)c1] | OCH₂ | 2-quinoline | H, — | — | — | — | — |
| 993 | A11 | CN | 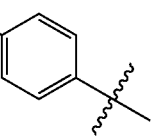 | OCH₂ | 2-quinoline | H, — | — | — | — | — |
| 994 | A12 | CN | 4-pyridinyl | OCH₂ | 2-quinoline | H, — | — | — | — | — |
| 995 | A12 | CN | 4-OMe-phenyl | OCH₂ | 2-quinoline | H, — | — | — | — | — |
| 996 | A12 | CN | 4-pyrazolyl | OCH₂ | 2-quinoline | H, — | — | — | — | — |
| 997 | A12 | CN | 3-(1-methyl-1H-pyrazolyl) | OCH₂ | 2-quinoline | H, — | — | — | — | — |
| 998 | A12 | CN | 4-(1-methyl-1H-pyrazolyl) | OCH₂ | 2-quinoline | H, — | — | — | — | — |
| 999 | A12 | CN | 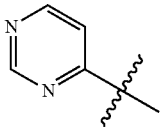 | OCH₂ | 2-quinoline | H, — | — | — | — | — |
| 1000 | A12 | CN | 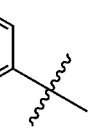 | OCH₂ | 2-quinoline | H, — | — | — | — | — |
| 1001 | A12 | CN | 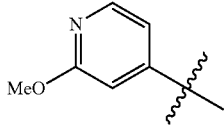 | OCH₂ | 2-quinoline | H, — | — | — | — | — |
| 1002 | A12 | CN | 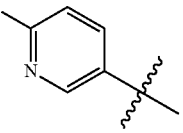 | OCH₂ | 2-quinoline | H, — | — | — | — | — |

-continued

| Ex. # | HET | W | X | Y | Z | R1a, R1b | R2 | R3 | R4 | R7 |
|---|---|---|---|---|---|---|---|---|---|---|
| 1003 | A12 | CN | 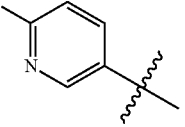 | OCH2 | 2-quinoline | H, — | — | — | — | — |
| 1004 | A12 | CN | 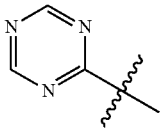 | OCH2 | 2-quinoline | H, — | — | — | — | — |
| 1005 | A12 | CN | 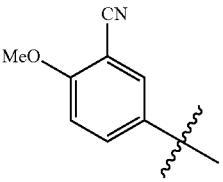 [SMILES: *c1ccc(OC)c(C#N)c1] | OCH2 | 2-quinoline | H, — | — | — | — | — |
| 1006 | A12 | CN | 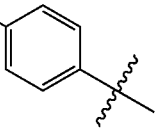 | OCH2 | 2-quinoline | H, — | — | — | — | — |
| 1007 | A13 | CN | 4-pyridinyl | OCH2 | 2-quinoline | H, H | — | — | — | — |
| 1008 | A13 | CN | 4-OMe-phenyl | OCH2 | 2-quinoline | H, H | — | — | — | — |
| 1009 | A13 | CN | 4-pyrazolyl | OCH2 | 2-quinoline | H, H | — | — | — | — |
| 1010 | A13 | CN | 3-(1-methyl-1H-pyrazolyl) | OCH2 | 2-quinoline | H, H | — | — | — | — |
| 1011 | A13 | CN | 4-(1-methyl-1H-pyrazolyl) | OCH2 | 2-quinoline | H, H | — | — | — | — |
| 1012 | A13 | CN | 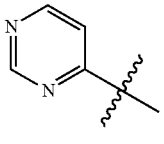 [SMILES: *c1ccncn1] | OCH2 | 2-quinoline | H, H | — | — | — | — |
| 1013 | A13 | CN | 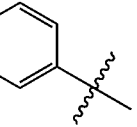 | OCH2 | 2-quinoline | H, H | — | — | — | — |
| 1014 | A13 | CN | 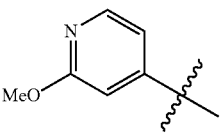 | OCH2 | 2-quinoline | H, H | — | — | — | — |
| 1015 | A13 | CN | 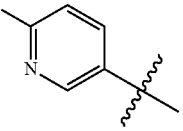 | OCH2 | 2-quinoline | H, H | — | — | — | — |
| 1016 | A13 | CN | 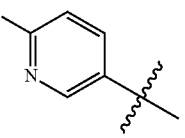 | OCH2 | 2-quinoline | H, H | — | — | — | — |

-continued

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 1017 | A13 | CN | 2-(1,3,5-triazinyl) | OCH$_2$ | 2-quinoline | H, H | — | — | — | — |
| 1018 | A13 | CN | 3-CN-4-OMe-phenyl | OCH$_2$ | 2-quinoline | H, H | — | — | — | — |
| 1019 | A13 | CN | 4-Cl-phenyl | OCH$_2$ | 2-quinoline | H, H | — | — | — | — |
| 1020 | A14 | CN | 4-pyridinyl | OCH$_2$ | 2-quinoline | H, H | — | — | — | — |
| 1021 | A14 | CN | 4-OMe-phenyl | OCH$_2$ | 2-quinoline | H, H | — | — | — | — |
| 1022 | A14 | CN | 4-pyrazolyl | OCH$_2$ | 2-quinoline | H, H | — | — | — | — |
| 1023 | A14 | CN | 3-(1-methyl-1H-pyrazolyl) | OCH$_2$ | 2-quinoline | H, H | — | — | — | — |
| 1024 | A14 | CN | 4-(1-methyl-1H-pyrazolyl) | OCH$_2$ | 2-quinoline | H, H | — | — | — | — |
| 1025 | A14 | CN | 4-pyrimidinyl | OCH$_2$ | 2-quinoline | H, H | — | — | — | — |
| 1026 | A14 | CN | 4-CN-phenyl | OCH$_2$ | 2-quinoline | H, H | — | — | — | — |
| 1027 | A14 | CN | 2-OMe-pyridin-4-yl | OCH$_2$ | 2-quinoline | H, H | — | — | — | — |
| 1028 | A14 | CN | 6-OMe-pyridin-3-yl | OCH$_2$ | 2-quinoline | H, H | — | — | — | — |
| 1029 | A14 | CN | 6-HO-pyridin-3-yl | OCH$_2$ | 2-quinoline | H, H | — | — | — | — |
| 1030 | A14 | CN | 2-(1,3,5-triazinyl) | OCH$_2$ | 2-quinoline | H, H | — | — | — | — |

-continued

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 1031 | A14 | CN | 3-CN-4-OMe-phenyl | OCH$_2$ | 2-quinoline | H, H | — | — | — | — |
| 1032 | A14 | CN | 4-Cl-phenyl | OCH$_2$ | 2-quinoline | H, H | — | — | — | — |
| 1033 | A15 | CN | 4-pyridinyl | OCH$_2$ | 2-quinoline | H, — | — | — | — | — |
| 1034 | A15 | CN | 4-OMe-phenyl | OCH$_2$ | 2-quinoline | H, — | — | — | — | — |
| 1035 | A15 | CN | 4-pyrazolyl | OCH$_2$ | 2-quinoline | H, — | — | — | — | — |
| 1036 | A15 | CN | 3-(1-methyl-1H-pyrazolyl) | OCH$_2$ | 2-quinoline | H, — | — | — | — | — |
| 1037 | A15 | CN | 4-(1-methyl-1H-pyrazolyl) | OCH$_2$ | 2-quinoline | H, — | — | — | — | — |
| 1038 | A15 | CN | 4-pyrimidinyl | OCH$_2$ | 2-quinoline | H, — | — | — | — | — |
| 1039 | A15 | CN | 4-CN-phenyl | OCH$_2$ | 2-quinoline | H, — | — | — | — | — |
| 1040 | A15 | CN | 2-OMe-pyridin-4-yl | OCH$_2$ | 2-quinoline | H, — | — | — | — | — |
| 1041 | A15 | CN | 6-OMe-pyridin-3-yl | OCH$_2$ | 2-quinoline | H, — | — | — | — | — |
| 1042 | A15 | CN | 6-OH-pyridin-3-yl | OCH$_2$ | 2-quinoline | H, — | — | — | — | — |
| 1043 | A15 | CN | 1,3,5-triazin-2-yl | OCH$_2$ | 2-quinoline | H, — | — | — | — | — |
| 1044 | A15 | CN | 3-CN-4-OMe-phenyl | OCH$_2$ | 2-quinoline | H, — | — | — | — | — |

-continued

| Ex. # | HET | W | X | Y | Z | R$_{1a}$, R$_{1b}$ | R$_2$ | R$_3$ | R$_4$ | R$_7$ |
|---|---|---|---|---|---|---|---|---|---|---|
| 1045 | A15 | CN | 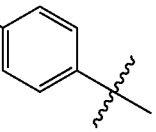 | OCH$_2$ | 2-quinoline | H, — | — | — | — | — |
| 1046 | A19 | CN | 4-pyridinyl | OCH$_2$ | 2-quinoline | H, — | — | — | — | — |
| 1047 | A19 | CN | 4-OMe-phenyl | OCH$_2$ | 2-quinoline | H, — | — | — | — | — |
| 1048 | A19 | CN | 4-pyrazolyl | OCH$_2$ | 2-quinoline | H, — | — | — | — | — |
| 1049 | A19 | CN | 3-(1-methyl-1H-pyrazolyl) | OCH$_2$ | 2-quinoline | H, — | — | — | — | — |
| 1050 | A19 | CN | 4-(1-methyl-1H-pyrazolyl) | OCH$_2$ | 2-quinoline | H, — | — | — | — | — |
| 1051 | A19 | CN | 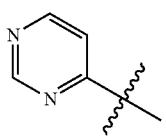 | OCH$_2$ | 2-quinoline | H, — | — | — | — | — |
| 1052 | A19 | CN | 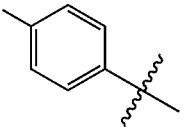 | OCH$_2$ | 2-quinoline | H, — | — | — | — | — |
| 1053 | A19 | CN | 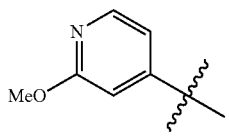 [SMILES: *c1ccnc(OC)c1] | OCH$_2$ | 2-quinoline | H, — | — | — | — | — |
| 1054 | A19 | CN | 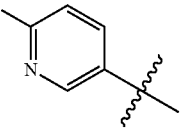 | OCH$_2$ | 2-quinoline | H, — | — | — | — | — |
| 1055 | A19 | CN | 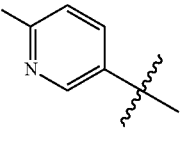 | OCH$_2$ | 2-quinoline | H, — | — | — | — | — |
| 1056 | A19 | CN | 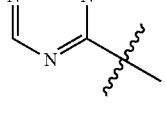 | OCH$_2$ | 2-quinoline | H, — | — | — | — | — |
| 1057 | A19 | CN | 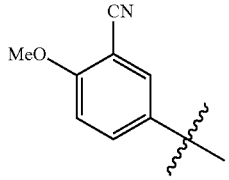 [SMILES: *c1ccc(OC)c(C#N)c1] | OCH$_2$ | 2-quinoline | H, — | — | — | — | — |
| 1058 | A19 | CN | 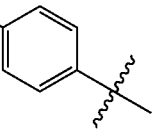 | OCH$_2$ | 2-quinoline | H, — | — | — | — | — |
| 1059 | A20 | CN | 4-pyridinyl | OCH$_2$ | 2-quinoline | H, H | — | — | — | — |
| 1060 | A20 | CN | 4-OMe-phenyl | OCH$_2$ | 2-quinoline | H, H | — | — | — | — |
| 1061 | A20 | CN | 4-pyrazolyl | OCH$_2$ | 2-quinoline | H, H | — | — | — | — |

-continued

| Ex. # | HET | W | X | Y | Z | R1a, R1b | R2 | R3 | R4 | R7 |
|---|---|---|---|---|---|---|---|---|---|---|
| 1062 | A20 | CN | 3-(1-methyl-1H-pyrazolyl) | OCH2 | 2-quinoline | H, H | — | — | — | — |
| 1063 | A20 | CN | 4-(1-methyl-1H-pyrazolyl) | OCH2 | 2-quinoline | H, H | — | — | — | — |
| 1064 | A20 | CN | 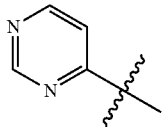 | OCH2 | 2-quinoline | H, H | — | — | — | — |
| 1065 | A20 | CN | 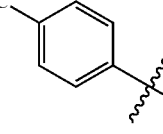 | OCH2 | 2-quinoline | H, H | — | — | — | — |
| 1066 | A20 | CN | 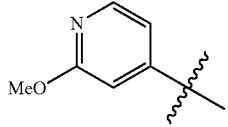 [SMILES: *c1ccnc(OC)c1] | OCH2 | 2-quinoline | H, H | — | — | — | — |
| 1067 | A20 | CN | 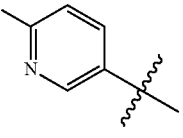 | OCH2 | 2-quinoline | H, H | — | — | — | — |
| 1068 | A20 | CN | 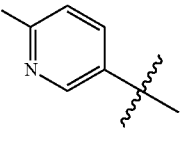 | OCH2 | 2-quinoline | H, H | — | — | — | — |
| 1069 | A20 | CN | 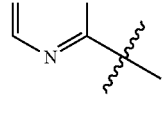 | OCH2 | 2-quinoline | H, H | — | — | — | — |
| 1070 | A20 | CN | 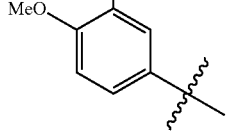 | OCH2 | 2-quinoline | H, H | — | — | — | — |
| 1071 | A20 | CN | 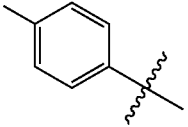 | OCH2 | 2-quinoline | H, H | — | — | — | — |
| 1072 | A32 | CN | 4-pyridinyl | OCH2 | 2-quinoline | — | H, H | — | — | H |
| 1073 | A32 | CN | 4-OMe-phenyl | OCH2 | 2-quinoline | — | H, H | — | — | H |
| 1074 | A32 | CN | 4-pyrazolyl | OCH2 | 2-quinoline | — | H, H | — | — | H |
| 1075 | A32 | CN | 3-(1-methyl-1H-pyrazolyl) | OCH2 | 2-quinoline | — | H, H | — | — | H |
| 1076 | A32 | CN | 4-(1-methyl-1H-pyrazolyl) | OCH2 | 2-quinoline | — | H, H | — | — | H |
| 1077 | A32 | CN | 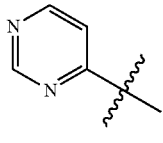 | OCH2 | 2-quinoline | — | H, H | — | — | H |

-continued

| Ex. # | HET | W | X | Y | Z | $R_{1a}, R_{1b}$ | $R_2$ | $R_3$ | $R_4$ | $R_7$ |
|---|---|---|---|---|---|---|---|---|---|---|
| 1078 | A32 | CN | NC-C6H4- | OCH$_2$ | 2-quinoline | — | H, H | — | — | H |
| 1079 | A32 | CN | 2-MeO-pyridin-4-yl | OCH$_2$ | 2-quinoline | — | H, H | — | — | H |
| 1080 | A32 | CN | 6-MeO-pyridin-3-yl | OCH$_2$ | 2-quinoline | — | H, H | — | — | H |
| 1081 | A32 | CN | 6-HO-pyridin-3-yl | OCH$_2$ | 2-quinoline | — | H, H | — | — | H |
| 1082 | A32 | CN | 1,3,5-triazin-2-yl | OCH$_2$ | 2-quinoline | — | H, H | — | — | H |
| 1083 | A32 | CN | 2-MeO-5-CN-phenyl | OCH$_2$ | 2-quinoline | — | H, H | — | — | H |
| 1084 | A32 | CN | Cl-C6H4- | OCH$_2$ | 2-quinoline | — | H, H | — | — | H |
| 1099 | A7 | Cl | pyridin-4-yl | OCH$_2$ | 2-quinoline | — | — | H | H | — |

Dosage and Administration

The present disclosure includes pharmaceutical composition for treating a subject having a neurological disorder comprising a therapeutically effective amount of a compound of Formulas (I), (II) and (III), a derivative or a pharmaceutically acceptable salt thereof, and a pharmaceutically acceptable excipient, carrier or diluent.

The pharmaceutical compositions can be administered in a variety of dosage forms including, but not limited to, a solid dosage form or in a liquid dosage form, an oral dosage form, a parenteral dosage form, an intranasal dosage form, a suppository, a lozenge, a troche, buccal, a controlled release dosage form, a pulsed release dosage form, an immediate release dosage form, an intravenous solution, a suspension or combinations thereof. The dosage can be an oral dosage form that is a controlled release dosage form. The oral dosage form can be a tablet or a caplet. The compounds can be administered, for example, by oral or parenteral routes, including intravenous, intramuscular, intraperitoneal, subcutaneous, transdermal, airway (aerosol), rectal, vaginal and topical (including buccal and sublingual) administration. In one embodiment, the compounds or pharmaceutical compositions comprising the compounds are delivered to a desired site, such as the brain, by continuous injection via a shunt.

In another embodiment, the compound can be administered parenterally, such as intravenous (IV) administration.

The formulations for administration will commonly comprise a solution of the compound of the Formulas (I), (II) and (III) dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of compound of Formulas (I), (II) and (III) in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In one embodiment, a compound of Formulas (I), (II) and (III) can be administered by introduction into the central nervous system of the subject, e.g., into the cerebrospinal fluid of the subject. The formulations for administration will commonly comprise a solution of the compound of Formulas (I), (II) and (III) dissolved in a pharmaceutically acceptable carrier. In certain aspects, the compound of Formulas (I), (II) and (III) is introduced intrathecally, e.g., into a cerebral ventricle, the lumbar area, or the cisterna magna. In another aspect, the compound of Formulas (I), (II) and (III) is introduced intraocularly, to thereby contact retinal ganglion cells.

The pharmaceutically acceptable formulations can easily be suspended in aqueous vehicles and introduced through conventional hypodermic needles or using infusion pumps. Prior to introduction, the formulations can be sterilized with, preferably, gamma radiation or electron beam sterilization.

In one embodiment, the pharmaceutical composition comprising a compound of Formulas (I), (II) and (III) is administered into a subject intrathecally. As used herein, the term "intrathecal administration" is intended to include delivering a pharmaceutical composition comprising a compound of Formulas (I), (II) and (III) directly into the cerebrospinal fluid of a subject, by techniques including lateral cerebroventricular injection through a burrhole or cisternal or lumbar puncture or the like (described in Lazorthes et al. Advances in Drug Delivery Systems and Applications in Neurosurgery, 143-192 and Omaya et al., Cancer Drug Delivery, 1: 169-179, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of a compound of Formulas (I), (II) and (III) to any of the above mentioned sites can be achieved by direct injection of the pharmaceutical composition comprising the compound of Formulas (I), (II) and (III) or by the use of infusion pumps. For injection, the pharmaceutical compositions can be formulated in liquid solutions, preferably in physiologically compatible buffers such as Hank's solution or Ringer's solution. In addition, the pharmaceutical compositions may be formulated in solid form and re-dissolved or suspended immediately prior to use. Lyophilized forms are also included. The injection can be, for example, in the form of a bolus injection or continuous infusion (e.g., using infusion pumps) of pharmaceutical composition.

In one embodiment, the pharmaceutical composition comprising a compound of Formulas (I), (II) and (III) is administered by lateral cerebro ventricular injection into the brain of a subject. The injection can be made, for example, through a burr hole made in the subject's skull. In another embodiment, the encapsulated therapeutic agent is administered through a surgically inserted shunt into the cerebral ventricle of a subject. For example, the injection can be made into the lateral ventricles, which are larger, even though injection into the third and fourth smaller ventricles can also be made.

In yet another embodiment, the pharmaceutical composition is administered by injection into the cisterna magna, or lumbar area of a subject.

For oral administration, the compounds will generally be provided in unit dosage forms of a tablet, pill, dragee, lozenge or capsule; as a powder or granules; or as an aqueous solution, suspension, liquid, gels, syrup, slurry, etc. suitable for ingestion by the patient. Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutical preparations for oral use can be obtained through combination of a compound of Formulas (I), (II) and (III) with a solid excipient, optionally grinding a resulting mixture, and processing the mixture of granules, after adding suitable additional compounds, if desired, to obtain tablets or dragee cores. Suitable solid excipients in addition to those previously mentioned are carbohydrate or protein fillers that include, but are not limited to, sugars, including lactose, sucrose, mannitol, or sorbitol; starch from corn, wheat, rice, potato, or other plants; cellulose such as methyl cellulose, hydroxypropylmethyl-cellulose or sodium carboxymethyl-cellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Capsules for oral use include hard gelatin capsules in which the active ingredient is mixed with a solid diluent, and soft gelatin capsules wherein the active ingredients is mixed with water or an oil such as peanut oil, liquid paraffin or olive oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

For transmucosal administration (e.g., buccal, rectal, nasal, ocular, etc.), penetrants appropriate to the barrier to be permeated are used in the formulation. Such penetrants are generally known in the art.

Formulations for rectal administration may be presented as a suppository with a suitable base comprising for example cocoa butter or a salicylate. Formulations suitable for vaginal administration may be presented as pessaries, tampons, creams, gels, pastes, foams or spray formulations containing in addition to the active ingredient such carriers as are known in the art to be appropriate. For intramuscular, intraperitoneal, subcutaneous and intravenous use, the compounds will generally be provided in sterile aqueous solutions or suspensions, buffered to an appropriate pH and isotonicity. Suitable aqueous vehicles include Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The suppositories for rectal administration of the drug can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The compounds can be delivered transdermally, by a topical route, formulated as applicator sticks, solutions, suspensions, emulsions, gels, creams, ointments, pastes, jellies, paints, powders, or aerosols.

The compounds may also be presented as aqueous or liposome formulations. Aqueous suspensions can contain a compound of Formulas (I), (II) and (III) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a compound of Formulas (I), (II) and (III) in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

For administration by inhalation, the compounds are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In general a suitable dose will be in the range of 0.01 to 100 mg per kilogram body weight of the recipient per day, preferably in the range of 0.1 to 10 mg per kilogram body weight per day. The desired dose is preferably presented once daily, but may be dosed as two, three, four, five, six or more subdoses administered at appropriate intervals throughout the day.

The compounds can be administered as the sole active agent, or in combination with other known therapeutics to be beneficial in the treatment of neurological disorders. In any event, the administering physician can provide a method of treatment that is prophylactic or therapeutic by adjusting the amount and timing of drug administration on the basis of observations of one or more symptoms (e.g., motor or cognitive function as measured by standard clinical scales or assessments) of the disorder being treated. Details on techniques for formulation and administration are well described in the scientific and patent literature, see, e.g., the latest edition of Remington's Pharmaceutical Sciences, Maack Publishing Co, Easton Pa. After a pharmaceutical composition has been formulated in an acceptable carrier, it can be placed in an appropriate container and labeled for treatment of an indicated condition. For administration of the compounds of Formulas (I), (II) and (III), such labeling would include, e.g., instructions concerning the amount, frequency and method of administration.

Biological Examples

In Vivo Methods

Subjects:

Male C57BL/6J mice (Charles River; 20-25 g) were used for all assays except prepulse inhibition (PPI) which used male DBA/2N mice (Charles River, 20-25 g). For all studies, animals were housed five/cage on a 12-h light/dark cycle with food and water available ad libitum.

Conditioned Avoidance Responding:

Testing was performed in commercially available avoidance boxes (Kinder Scientific, Poway Calif.). The boxes were divided into two compartments separated by an archway. Each side of the chamber has electronic grid flooring that is equipped to administer footshocks and an overhead light. Training consisted of repeated pairings of the light (conditioned stimulus) followed by a shock (unconditioned stimulus). For each trial the light was presented for 5 sec followed by a 0.5 mA shock that would terminate if the mouse crossed to the other chamber or after 10 seconds. The intertrial interval was set to 20 seconds. Each training and test session consisted a four min habituation period followed by 30 trials. The number of avoidances (mouse crossed to other side during presentation of the light,), escapes (mouse crossed to the other side during presentation of the shock) and failures (mouse did not cross during the entire trial period) were recorded by a computer. For study inclusion an animal had to reach a criterion of at least 80% avoidances for two consecutive test sessions.

PPI:

Mice were individually placed into the test chambers (StartleMonitor, Kinder Scientific, Poway Calif.). The animals were given a five min acclimation period to the test chambers with the background noise level set to 65 decibel (dB) which remained for the entire test session. Following acclimation, four successive trials 120 dB pulse for 40 msec were presented, however these trials were not included in data analysis. The mice were then subjected to five different types of trials in random order: pulse alone (120 dB for 40 msec), no stimulus and three different prepulse+pulse trials with the prepulse set at 67, 69 or 74 dB for 20 msec followed a 100 msec later by a 120 dB pulse for 40 msec. Each animal received 12 trials for each condition for a total of 60 trials with an average intertrial interval of 15 sec. Percent PPI was calculated according to the following formula: (1−(startle response to prepulse+pulse)/startle response to pulse alone))×100.

MK-801-Induced Hyperactivity:

After a 30 min acclimatation to the test room mice were individually placed into test cages for a 30 min habituation period. Following habituation to test cages, baseline activity was recorded for 60 min. Mice were then briefly removed and administered test compound and placed immediately back into the test cage. At 5 min prior to test time mice were again briefly removed from test cages and administered MK-801 (0.3 mg/kg, i.p. in 0.9% saline) and then immediately placed back into test cages and activity level recorded 1 hour. Activity level was measured as distance traveled in centimeters (Ethovision tracking software, Noldus Inc. Wageningen, Netherlands).

Catalepsy:

Mice were placed on a wire mesh screen set at a 60 degree angle with their heads facing upwards and the latency to move or break stance was recorded. Animals were given three trials per time point with a 30 sec cut-off per trial.

Data Analysis:

A one-way or two-way ANOVA was used to evaluate overall differences between treatments and a Tukey's post-hoc test or Student's t-test was used to evaluate differences between treatment groups for the one-way ANOVA and a Bonferroni test was used for the two-way ANOVA. The criterion for statistical significance was set to $p \leq 0.05$.

In Vitro Methods hPDE10A1 Enzyme Activity:

50 µl samples of serially diluted Human PDE10A1 enzyme were incubated with 50 µl of [$^3$H]-cAMP for 20 minutes (at 37° C.). Reactions were carried out in Greiner 96 deep well 1 ml master-block. The enzyme was diluted in 20 mM Tris HCl pH7.4 and [$^3$H]-cAMP was diluted in 10 mM MgCl$_2$, 40 mM Tris.HCl pH 7.4. The reaction was terminated by denaturing the PDE enzyme (at 70° C.) after which [$^3$H]-5'-AMP was converted to [$^3$H]-adenosine by adding 25 µl snake venom nucleotidase and incubating for 10 minutes (at 37° C.). Adenosine, being neutral, was separated from charged cAMP or AMP by the addition of 200 µl Dowex resin. Samples were shaken for 20 minutes then centrifuged for 3 minutes at 2,500 r.p.m. 50 µl of supernatant was removed and added to 200 µl of MicroScint-20 in white plates (Greiner 96-well Optiplate) and shaken for 30 minutes before reading on Perkin Elmer TopCount Scintillation Counter.

hPDE10A1 Enzyme Inhibition:

To check inhibition profile 11 µl of serially diluted inhibitor was added to 50 µl of [$^3$H]-cAMP and 50 µl of diluted Human PDE10A1 and assay was carried out as in the enzyme activity assay. Data was analysed using Prism software (GraphPad Inc). Representative compounds of this disclosure are shown in the table below. A compound with the value "A" had an $IC_{50}$ value less than or equal to 50 nM. A compound with the value "B" had an $IC_{50}$ value greater than 50 nM:

| Ex | Name | hPDE10A1 $IC_{50}$ Band |
|---|---|---|
| 37 | 4-(pyridin-4-yl)-3-(4-(quinolin-2-ylmethoxy)phenyl)furan-2(5H)-one | A |
| 53 | 4-(3-fluoro-4-methoxyphenyl)-3-(4-(quinolin-2-ylmethoxy)phenyl)furan-2(5H)-one | A |
| 54 | 4-(3-chloro-4-methoxyphenyl)-3-(4-(quinolin-2-ylmethoxy)phenyl)furan-2(5H)-one | A |
| 55 | 2-methoxy-5-(5-oxo-4-(4-(quinolin-2-ylmethoxy)phenyl)-2,5-dihydrofuran-3-yl)benzonitrile | A |
| 59 | 4-(4-methoxyphenyl)-3-(4-(quinolin-2-ylmethoxy)phenyl)furan-2(5H)-one | A |
| 94 | 1-methyl-4-(pyridin-4-yl)-3-(4-(quinolin-2-ylmethoxy)phenyl)-1H-pyrrol-2(5H)-one | A |
| 125 | 4-(4-methoxyphenyl)-1-methyl-3-(4-(quinolin-2-ylmethoxy)phenyl)-1H-pyrrol-2(5H)-one | A |
| 14 | 3-(4-methoxyphenyl)-4-(4-(quinolin-2-ylmethoxy)phenyl)furan-2(5H)-one | A |
| 424 | 4-(2-chloro-4-(quinolin-2-ylmethoxy)phenyl)-3-(4-methoxyphenyl)furan-2(5H)-one | B |
| 1085 | 4-morpholino-3-(4-(quinolin-2-ylmethoxy)phenyl)furan-2(5H)-one | B |
| 1094 | 3-(pyridin-4-yl)-4-(4-(quinolin-2-ylmethoxy)phenyl)isoxazol-5(2H)-one | A |
| 1095 | 3-(4-methoxyphenyl)-4-(4-((6-methylpyridin-2-yl)methoxy)phenyl)furan-2(5H)-one | B |
| 1096 | 5-(pyridin-4-yl)-4-(4-(quinolin-2-ylmethoxy)phenyl)-1H-pyrazol-3(2H)-one | B |
| 1097 | 2-methyl-5-(pyridin-4-yl)-4-(4-(quinolin-2-ylmethoxy)phenyl)-1H-pyrazol-3(2H)-one | B |
| 1098 | 4-(pyridin-3-yl)-3-(4-(quinolin-2-ylmethoxy)phenyl)furan-2(5H)-one | B |
| 1099 | 3-(3-chloro-4-(quinolin-2-ylmethoxy)phenyl)-4-(pyridin-4-yl)furan-2(5H)-one | B |

What is claimed is:
1. A compound of Formula (I)

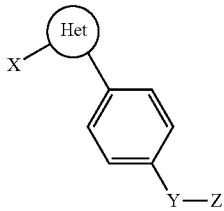

or pharmaceutically acceptable salt thereof,
wherein:
HET is a heterocyclic ring having formula A7, A8, A10, A16, A17, A29 or A30

A7
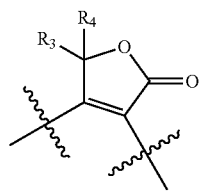

A8
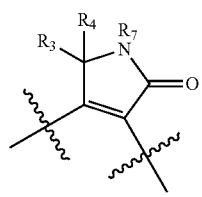

A10
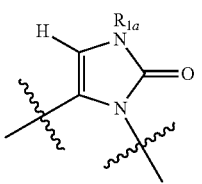

A16
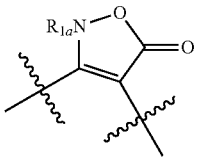

A17
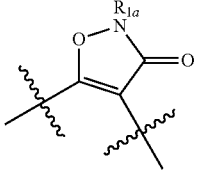

A29
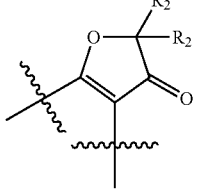

A30
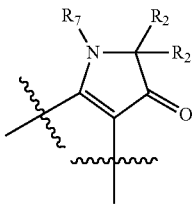

and the left most radical is connected to the X group;

X is optionally substituted heterocycloalkyl, optionally substituted aryl or optionally substituted heteroaryl;

Y is —$CH_2O$— or —$OCH_2$— with the rightmost radical of the Y group connected to the Z substituent;

Z is optionally substituted heteroaryl;

$R_{1a}$ is hydrogen;

each $R_2$ is independently hydrogen, optionally substituted alkyl, optionally substituted cycloalkyl, optionally substituted cycloalkylalkyl or optionally substituted alkoxyalkyl, with the proviso that at least one $R_2$ is hydrogen;

$R_3$ and $R_4$ are independently hydrogen, $C_1$-$C_4$ alkyl, —$CF_3$ or optionally substituted cycloalkyl, with the proviso that at least one $R_3$ or $R_4$ group must be hydrogen; and $R_7$ is hydrogen, optionally substituted alkyl, optionally substituted cycloalkyl, optionally substituted cycloalkylalkyl or optionally substituted alkoxyalkyl.

2. The compound claim 1, wherein Y is —$CH_2O$— with the right most radical connected to the Z substituent, or a pharmaceutically acceptable salt thereof.

3. The compound of claim 1, wherein Y is —$OCH_2$— with the right most radical connected to the Z substituent, or a pharmaceutically acceptable salt thereof.

4. The compound of claim 1, wherein Z is an optionally substituted heteroaryl having only 6 ring atoms or an optionally substituted heterobicyclic ring system, or a pharmaceutically acceptable salt thereof.

5. The compound of claim 1, wherein Z is an optionally substituted heteroaryl having only 6 ring atoms selected from C and N provided the total number of ring nitrogens is less than or equal to two; said ring is optionally substituted with up to 2 substituents independently selected from the group consisting of $C_1$-$C_4$ alkyl, $C_1$-$C_4$ alkoxy, $C_3$-$C_6$ cycloalkyl, $C_3$-$C_6$ cycloalkyloxy, $C_4$-$C_7$ cycloalkylalkyl, cycloalkylalkoxy, halogen, alkylsulfonyl, cyano and nitro, or a pharmaceutically acceptable salt thereof.

6. The compound of claim 1, wherein Z is benzimidazolyl, quinolinyl, tetrahydroquinolyl, imidazo[1,2-a]pyridin-2-yl, tetrahydroisoquinolyl, 5-methylpyridin-2-yl, 3,5-dimethylpyridin-2-yl, 6-fluoroquinolyl or isoquinolinyl substituted with up to 3 substituents independently selected from the group consisting of $C_1$-$C_4$ alkyl, $C_1$-$C_4$ alkoxy, $C_3$-$C_6$ cycloalkyl, $C_3$-$C_6$ cycloalkyloxy, $C_4$-$C_7$ cycloalkylalkyl, cycloalkylalkoxy, halogen, alkylsulfonyl, cyano and nitro, or a pharmaceutically acceptable salt thereof.

7. The compound of claim 1, wherein the Z substituent is unsubstituted, or a pharmaceutically acceptable salt thereof.

8. The compound of claim 1, wherein X is a heterocycloalkyl having Formula B1-B16

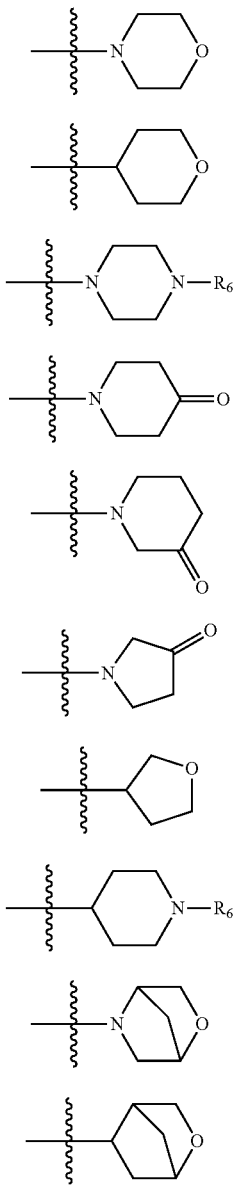

B1
B2
B3
B4
B5
B6
B7
B8
B9
B10

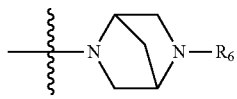 B11

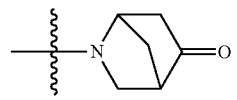 B12

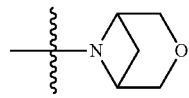 B13

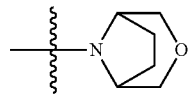 B14

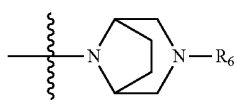 B15

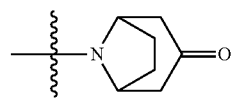 B16 wherein $R_6$ is hydrogen, $C_1$-$C_6$ alkyl, $C_3$-$C_6$ cycloalkyl or $C_4$-$C_7$ cycloalkylalkyl, or a pharmaceutically acceptable salt thereof.

9. The compound of claim 1, wherein X is an optionally substituted heteroaryl, or a pharmaceutically acceptable salt thereof.

10. The compound of claim 1, wherein X is phenyl, restricted phenyl or pyridinyl, or a pharmaceutically acceptable salt thereof.

11. The compound of claim 1, wherein X is benzo[d]oxazoyl, benzo[c][1,2,5]oxadiazyl, benzo[c][1,2,5]thiadiazolyl, benzo[d]isoxazolyl, 1H-benzo[d]imidazoyl, benzo[d]thiazoyl, benzo[c]isothiazolyl, benzo[d]isothiazolyl, benzo[c]isoxazolyl, imidazo[1,2-a]pyridinyl or imidazo[1,5-a]pyridinyl, or a pharmaceutically acceptable salt thereof.

12. A pharmaceutical composition comprising: (i) the compound of any of claims 1-11, or a pharmaceutically acceptable salt thereof; and (ii) a pharmaceutically acceptable carrier or excipient.

* * * * *